(12) United States Patent
Phillips et al.

(10) Patent No.: US 7,442,786 B2
(45) Date of Patent: Oct. 28, 2008

(54) VASCULAR-PREFERRED PROMOTERS

(75) Inventors: Jonathan Phillips, Auckland (NZ);
Sathish Puthigae, Auckland (NZ);
JiaLong Yao, Auckland (NZ); Barry Flinn, New Brunswick (CA); Richard S. Forster, Auckland (NZ); Clare Eagleton, Auckland (NZ)

(73) Assignee: Arborgen, LLC, Summerville, SC (US)

( * ) Notice: Subject to any disclaimer, the term of this patent is extended or adjusted under 35 U.S.C. 154(b) by 193 days.

(21) Appl. No.: 10/717,897

(22) Filed: Nov. 21, 2003

(65) Prior Publication Data

US 2004/0163146 A1 Aug. 19, 2004

Related U.S. Application Data

(60) Provisional application No. 60/428,287, filed on Nov. 22, 2002.

(51) Int. Cl.
*C12N 15/82* (2006.01)
*A01H 5/00* (2006.01)
*A01H 7/00* (2006.01)

(52) U.S. Cl. .................. 536/24.1; 435/320.1; 435/419; 800/298

(58) Field of Classification Search .................. 536/24.1
See application file for complete search history.

(56) References Cited

U.S. PATENT DOCUMENTS

| | | | |
|---|---|---|---|
| 4,458,066 | A | 7/1984 | Caruthers et al. |
| 5,451,514 | A | 9/1995 | Boudet et al. |
| 5,565,340 | A | 10/1996 | Chenchik et al. |
| 5,759,822 | A | 6/1998 | Chenchik et al. |
| 6,051,757 | A | 4/2000 | Barton et al. |
| 6,132,970 | A | 10/2000 | Stemmer |
| 6,187,994 | B1 | 2/2001 | Baszcynski et al. |
| 6,204,434 | B1 | 3/2001 | Bloksberg et al. |
| 6,506,559 | B1 | 1/2003 | Fire et al. |
| 6,518,485 | B1 | 2/2003 | Connett-Porceddu et al. |
| 6,596,925 | B1 | 7/2003 | Perera et al. |
| 2003/0101478 | A1 | 5/2003 | Perera et al. |
| 2004/0146904 | A1 | 7/2004 | Phillips |

FOREIGN PATENT DOCUMENTS

| | | |
|---|---|---|
| EP | 0 120 516 B1 | 10/1991 |
| EP | 0 154 204 B1 | 1/1994 |
| EP | 0 271 988 B1 | 8/1995 |
| WO | WO 92/04449 | 3/1992 |
| WO | WO 93/19189 | 9/1993 |
| WO | WO 94/23044 | 10/1994 |
| WO | WO 99/61631 | 12/1999 |
| WO | WO 01/98485 A1 | 12/2001 |
| WO | WO2004-048595 | 6/2004 |
| WO | WO 2004/108903 A2 | 12/2004 |

OTHER PUBLICATIONS

Bevan M. et al. Tissue- and cell-specific activity of a phenylalanine ammonia-lyase promoter in transgenic plants. EMBO J. Jul. 1989;8(7):1899-906.*

Polvere R.I. et al. GenBank Accession No. U88240, *Trichinella spiralis* hypothetical ORF 2.20 mRNA, partial cds, Mar. 4, 1997.*

Buzeli R.A. et al. Tissue-specific regulation of BiP genes: a cis-acting regulatory domain is required for BiP promoter activity in plant meristems. Plant Mol. Biol. Nov. 2002;50(4-5);757-71.*

Kim Y et al. A 20 nucleotide upstream element is essential for the nopaline synthase (nos) promoter activity. Plant Mol Biol. Jan. 1994; 24(1):105-17.*

Gillespie D. The magic and challenge of DNA probes as diagnostic reagents. Vet Microbiol. Sep. 1990;24(3-4):217-33. Review.*

Bevan et al., "Tissue- and cell-specific activity of a phenylalanine ammonia-lyase promoter in transgenic plans," *The EMBO Journal*, 1989, vol. 8, No. 7, pp. 1899-1906.

Datta et al., "Nucleotide sequence of a gene encoding soybean repetitive praline-rich protein 3," *Plant Molecular Biology*, 1990, pp. 285-286, vol. 14, Kluwer Academic Publishers, Belgium.

Golovkin et al., "Production of transgenic maize plants by direct DNA uptake into embryogenic protoplasts," *Plant Science*, 1993, pp. 41-52, vol. 90, Elsevier Scientific Publishers Ireland Ltd.

McCarthy et al., "The Rate of Change of DNA in Evolution," *In Evolution of Genetic Systems*, 1972, pp. 1-43, H.H. Smith (ed.), Brookhaven Symposium in Biology No. 23, Gordon and Breach, New York.

Rogers et al., "Improved Vectors for Plant Transformation: Expression Cassette Vectors and New Selectable Markers," *Methods in Enzymology*, 1987, pp. 252-277, vol. 153, Academic Press, Inc.

Schmidhauser et al., "Regions of Broad-Host-Range Plasmid RK2 Involved in Replication and Stable Maintenance in Nine Species of Gram-Negative Bacteria," *Journal of Bateriology*, Oct. 1985, pp. 446-455, vol. 164, No. 1, American Society for Microbiology.

Sibley et al., "The Phylogeny and Classification of the Passerine Birds, Based on Comparisons of the Genetic Material, DNA," *ACTA XVIII Congressus Internationalis Ornithologici*, Aug. 16-24, 1982, pp. 83-121, vol. 1.

(Continued)

*Primary Examiner*—Cynthia Collins
(74) *Attorney, Agent, or Firm*—Foley & Lardner LLP

(57) ABSTRACT

The present invention relates to the regulation of polynucleotide transcription and/or expression. In particular, this invention relates to polynucleotide regulatory sequences isolated from *Eucalyptus grandis* and *Pinus radiata* that are capable of conferring vascular-preferred polynucleotide transcription in plant cells. Constructs and methods for using the inventive regulatory sequences for modifying transcription of endogenous and/or heterologous polynucleotides also are included in the invention.

6 Claims, 4 Drawing Sheets

OTHER PUBLICATIONS

Ziv Shani et al., "Cellulose Binding Domain Increases Cellulose Synthase Activity in *Acetobacter xylinum*, and Biomass of Transgenic Plants", Plant Biotechnology and In Vitro Biology in the 21st Century, Proceedings of the IXth International Congress of the International Association of Plant Tissue Culture and Biotechnology Jerusalem, Isreal, Jun. 14-19, 1998, Kluwer Academic Publishers, 1999, pp. 213-218.

Michael J. Adang et al., "The Reconstruction and Expression of a *Bacillus thuringiensis cry IIIA* gene in protoplasts and potato plants", Plant Molecular Biology, Mar. 1993, vol. 21, No. 6, pp. 1131-1145.

Stephen F. Altschul et al., "Gapped BLAST and PSI-BLAST: A new generation of protein database search programs", Nucleic Acids Research, Oxford University Press, 1997, vol. 25, No. 17, pp. 3389-3402.

Stephen F. Altschul et al., " Basic Local Alignment Search Tool", J. Mol. Biol., Academic Press Limited, Oct. 5, 1990, vol. 215, No. 3, pp. 403-410.

"Crop Species", Handbook of Plant Cell Culture, 1990 UCLA Symposium on Molecular Strategies for Crop Improvements, 3 pages.

Shabbir B. Bambot et al., "Efficient Total Gene Synthesis of 1.35-kb Hybrid Alpha-Lytic Protease Gene Using the Polymerase Chain Reaction", PCR Methods and Applications, Cold Spring Harbor Laboratory, Feb. 1993, vol. 2, No. 3, pp. 266-271.

Marie Baucher et al., "Red Xylem and Higher Lignin Extractability by Down-Regulating a Cinnamyl Alcohol Dehydrogenase in Poplar", Plant Physioll, 1996, vol. 112, pp. 1479-1490.

S. L. Beaucage, et al., "Deoxynucleoside Phosphoramidites—A New Class of Key Intermediates for Deoxypolynucleotide Synthesis", Tetrahedron Letters, Pergamon Press Ltd., 1981, vol. 22, No. 20, pp. 1859-1862.

Michael Bevan, "Binary *Argrobacterium* Vectors for Plant Transformation", IRL Press Limited, 1984, vol. 12, No. 22, pp. 8711-8721.

E. T. Bolton et al., "A General Method for the Isolation of RNA Complementary to DNA", Biochemistry: Bolton and McCarthy, Proc. Natl. Acad. Sci., 1962, Vol. 48, pp. 1390-1397.

Tom I. Bonner et al., "Reduction in the Rate of DNA Reassociation by Sequence Divergence", Journal of Molecular Biology, Mar. 15, 1973, vol. 81, pp. 123-135.

Mark D. Burow et al., "High Frequency Generation of Transgenic Tobacco Plants after Modified Leaf Disk Cocultivation with *Agrobacterium tumefaciens*" Plant Molecular Biology Reporter, Transaction Periodicals Consortium, Rutgers University, May 1990, vol. 8, No. 2, pp. 124-139.

Chang et al., "A Simple and Efficient Method for Isolating RNA from Pine Trees", Plant Molecular Biology Reporter, Transaction Periodicals Consortium, Rutgers University, Jun. 1993, vol. 11, No. 2, pp. 113-116.

Alan H. Christensen et al., "Ubiquitin Promoter-based Vectors for High Level Expression of Selectable and/or Screenable Marker Genes in Monocotyledonous Plants", Transgenic Research, Chapman & Hall, May 1996, vol. 5, No. 3, pp. 213-218.

Heather Coleman et al., "Increased Growth and Yield by Altered Carbohydrate Allocation", Intl. Union of Forestry Research Organizations Biennial Conference in Umea, Sweden, Jun. 2003, 1 page.

Henry Daniell et al., "Containment of Herbicide Resistance Through Genetic Engineering of the Chloroplast Genome", Apr. 1998, Nature Biotechnology, vol. 16, pp. 345-348.

Kathleen D'Halluin et al., "Transgenic Maize Plants by Tissue Electroporation", The Plant Cell, 1992 Society of Plant Physiologists, Dec. 1992, vol. 4, 1495-1505.

D. Palitha Dharmawardhana et al., "cDNA Cloning and Heterologous Expression of Coniferin beta-glucosidase", Plant Molecular Biology, International Society for Plant Molecular Biology, Kluwer Academic Publishers, May 1999, vol. 40, No. 2, pp. 365-372.

Patrick Dillon et al., "Use of Polymerase Chain Reaction for the Rapid Construction of Synthetic Genes", PCR Protocols: Current Methods and Applications, Methods in Molecular Biology, 1993, Humana Press Inc., vol. 15, pp. 263-268.

Catherine Feuillet et al., "Tissue- and Cell-Specific Expression of a Cinnamyl Alcohol Dehydrogenase Promoter in Transgenic Poplar Plants", Plant Molecular Biology, International Society for Plant Molecular Biology, Kluwer Academic Publishers, Feb. 1995, vol. 27, No. 4, pp. 651-667.

Robert T. Fraley et al., "Expression of Bacterial Genes in Plant Cells", Proc. Natl. Acad. Sci. USA, Monsanto Company, Aug. 1983, Vol. 80, pp. 4803-4807.

C. Grand et al., "Inhibition of Cinnamyl-alcohol-dehydrogenase Activity and Lignin Synthesis in Poplar (*Populus X euramericana* Dode) Tissues by Two Organic Compounds", Planta, Springer-Verlag, 1985, vol. 163, No. 2, pp. 232-237.

Jacqueline Grima-Pettenati et al., "Lignin Genetic Engineering Revisited", Plant Science, Elsevier Science Ireland Ltd., 1999, vol. 145, pp. 51-65.

Diane Hatton et al., "Two Classes of CIS Sequences Contribute to Tissue-Specific Expression of a PAL2 Promoter in Transgenic Tobacco", The Plant Journal, 1995, vol. 7, No. 6, pp. 859-876.

Karl D. Hauffe et al., "Combinatorial Interactions Between Positive and Negative CIS-acting Elements Control Spatial Patterns of 4CL-1 Expression in Transgenic Tobacco", The Plant Journal, 1993, vol. 4, No. 2, pp. 235-253.

Akio Hayashimoto et al., "A polyethylene Glycol=Mediated Protoplast Transformation System for Production of Fertile Transgenic Rice Plants", Plant Physiology, The American Society of Plant Physiologists, Jul. 1990, vol. 93, No. 3, pp. 857-863.

Luis Herrara-Estrella et al., Expression of Chimaeric Genes Transferred into Plant Cells Using a Ti-plasmid-derived Vector, Nature, International Weekly Journal of Science, Macmillan Journals Ltd., May 19-25, 1983, vol. 303, No. 5914, pp. 209-213.

Maud A. W. Hinchee et al., "Production of Transgenic Soybean Plants Using Agrobacterium-Mediated DNA Transfer", Bio/Technology, The International Monthly for Industrial Biology, Aug. 1988, vol. 6, pp. 915-922.

Eugene W. Holowachuk et al., "Efficient Gene Synthesis by Klenow Assembly / Extension—Pfu Polymerase Amplification (KAPPA) of Overlapping Oligonucleotides", PCR Methods and Applications, Cold Spring Harbor Laboratory, vol. 4, pp. 299-302.

R. B. Horsch et al., Rapid Assay of Foreign Gene Expression in Leaf Discs Transformed by *Agrobacterium tumefaciens*: Role of T-DNA Borders in the Transfer Process, Proc. Natl. Acad. Sci. USA, Jun. 1986, vol. 83, pp. 4428-4432.

R. B. Horsch et al., "A Simple and General Method for Transferring Genes into Plants", Science 227, Mar. 1985, pp. 1229-1231.

Richard A. Jefferson et al., GUS Fusions: Beta-glucuronidase as a Sensitive and Versatile Gene Fusion Marker in Higher Plants, The Embo Journal, IRL Press Limited, Dec. 20, 1987, vol. 6, No. 13, pp. 3901-3907.

Richard A. Jefferson, "Assaying Chimeric Genes in Plants: The GUS Gene Fusion System", Plant Molecular Biology Reporter, Plant Breeding Institute, 1987, vol. 5, No. 4, pp. 387-405.

Beat Keller et al., "Vascular Expression of a Bean Cell Wall Glycine-rich Protein—beta—glucuronidase Gene Fusion in Transgenic Tobacco", The Embo Journal , IRL Press Limited, May 1989, vol. 8, No. 5, pp. 1309-1314.

Beat Keller et al., "Vascular expression of the *grp1.8* promoter in controlled by three specific regulatory elements and one unspecific activating sequence", Plant Molecular Biology, International Society for Plant Molecular Biology, Kluwer Academic Publishers, Oct. 1994, vol. 26, No. 2, pp. 747-756.

Harry J. Klee et al., "Vectors for Transformation of Higher Plants", Bio/Technology, Jul. 1985, vol. 3, pp. 637-642.

T. M. Klein et al., "Factors Influencing Gene Delivery into *Zea Mays* Cells by High-Velocity Microprojectiles, Bio/Technology,"BioActive Compounds From Algae May 1988, vol. 6, pp. 559-563.

Halina Kononowicz, Subdomains of the Octopine Synthase Upstream Activating Element Direct Cell-Specific Expression in Transgenic Tobacco Plants, The Plant Cell, 1992 American Society of Plant Physiologists, Jan. 1992, vol. 4, pp. 17-27.

Eric Lacombe et al., Characterization of *cis*-elements Required for Vascular Expression of the *Cinnamoyl CoA Reductase* Gene and for Protein DNA Complex Formation, The Plant Journal, 2000 Blackwell Science Ltd., vol. 23, No. 5, pp. 663-676.

Ilan Levy et al., Modification of Polysaccharides and Plant Cell Wall by endo-1,4-beta-glucanase and Cellulose Binding Domains, Biomolecular Engineering, 2002 Elsevier Science B. V., Vol. 19, pp. 17-30.

Antonio Leyva et al., "cis-Element Combinations Determine Phenylalanine Ammonia-Lyase Gene Tissue-Specific Expression Patterns", The Plant Cell, 1992 American Society of Plant Physiologists, Mar. 1992, vol. 4, pp. 263-271.

Carol A. Loopstra et al., "Xylem-Specific Gene Expression in Loblolly Pine", Plant Molecular Biology, International Society for Plant Molecular Biology, Kluwer Academic Publishers, Jan. 1995, vol. 27, No. 2, pp. 277-291.

Cathie Martin et al., "MYB Transcription Factors in Plants", Trends in Genetics, 1997 Elsevier Science Ltd., Feb. 1997, vol. 13, No. 2, pp. 67-73.

Narumi Matsuda et al., "Partial Male Sterility in Transgenic Tobacco Carrying Antisense and Sense PAL cDNA Under the Control of a Tapetum-Specific Promoter", Plant & Cell Physiology, The Japanese Society of Plant Physiologists, Mar. 1996, vol. 37, No. 2, pp. 215-222.

David McElroy et al., "Isolation of an Efficient Actin Promoter for Use in Rice Transformation", The Plant Cell, 1990 American Society of Plant Physiologists, Feb. 1990, vol. 2, 163-171.

S. G. Rogers et al., "Improved Vectors for Plant Transformation: Expression Cassette Vectors and New Selectable Markers", Methods in Enzymology, Recombinant DNA, Part D, Academic Press, 1987, Inc., vol. 153, pp. 253-277.

B. L. Miki et al., "Procedures for Introducing Foreign DNA into Plants", Methods in Plant Molecular Biology and Biotechnology, CRC Press, 1993, pp. 67-88.

David A. Neustaedter et al., "A Novel Parsley 4CL1 cis-element is Required for Developmentally Regulated Expression and Protein DNA Complex Formation", The Plant Journal, 1999, Blackwell Science Ltd., vol. 18, No. 1, pp. 77-88.

Eun-Gyu No et al., "Sequences Upstream and Downstream of Two Xylem-Specific Pine Genes Influence Their Expression", Plant Science, 2000 Elsevier Science, vol. 160, pp. 77-86.

Patrick Paddison et al., "Short Hairpin RNAs (shRNAs) Induce Sequence-Specific Silencing in Mammalian Cells", Genes & Development, Cold Spring Laboratory Press, 2002, vol. 16, pp. 948-958.

Ingo Potrykus et al., "Direct Gene Transfer to Cells of a Graminaceous Monocot", Mol. Gen. Genet, Springer-Verlag, 1985, vol. 199, pp. 183-188.

S.N.I.M. Salehuzzaman et al., "Isolation and Characterization of a cDNA Encoding Granule-Bound Starch Synthase in Cassava (Manihot esculenta Crantz) and its Antisense Expression in Potato", Plant Molecular Biology, Kluwer Academic Publishers, 1993, vol. 23, pp. 947-962.

C.J.S.Smith et al., "Antisense RNA Inhibition of Polygalactronase Gene Expression in Transgenic Tomatoes", Nature, Aug. 1988, vol. 334, No. 25, pp. 724-726.

Christopher J.S. Smith et al., "Inheritance and Effect on Ripening of Antisense Polygalacturonase Genes in Transgenic Tomatoes", Plant Molecular Biology, International Society for Plant Molecular Biology, Kluwer Academic Publishers, Mar. 1990, vol. 14, No. 3, pp. 369-379.

David M. Stalker et al., "Purification and Properties of a Nitrilase Specific for the Herbicide Bromoxynil and Corresponding Nucleotide Sequence Analysis of the b*xn* Gene*"*, The Journal of Biological Chemistry, The American Society for Biochemistry and Molecular Biology, Inc., May 5, 1988, vol. 263, No. 13, pp. 6310-6314.

Joëlle Thillet et al., "Site-Directed Mutagenesis of Mouse Dihydrofolate Reductase", The Journal of Biological Chemistry, The American Society for Biochemistry and Molecular Biology, Inc. Sep. 1968, vol. 263, No. 25, pp. 12500-12508.

Sonia Torres-Schumann et al., "In Vitro Binding of the Tomato bZIP Transcriptional Activator VSF-1 to a Regulatory Element that Controls Xylem-Specific Gene Expression", The Plant Journal, 1996, vol. 9, No. 3, pp. 283-296.

Ingrid M. Van Der Meer et al., "Antisense Inhibition of Flavonoid Biosynthesis in Petunia Anthers Results in Male Sterility", The Plant Cell, American Society of Plant Physiologists, Mar. 1992, vol. 4, pp. 253-262.

Donald R. Needham et al., "Characterization of an Adduct Between CC-1065 and a Defined Oligodeoxynucleotide Duplex", Nucleic Acids Research, IRL Press Limited, 1984, vol. 12, No. 15, pp. 6159-6168.

Vimla Vasil et al., "Regeneration of Plants From Embryogenic Suspension Culture Protoplasts of Wheat (Triticum aestivum L.)", Bio/Technology, May 1990, vol. 8, pp. 429-434.

Vimla Vasil et al., "Herbicide Resistant Fertile Transgenic Wheat Plants Obtained by Microprojectile Bombardment of Regenerable Embryogenic Callus", Bio/Technology, Jun. 1992, vol. 10, pp. 667-674.

Michael A. Wosnick et al., "Rapid Construction of Large Synthetic Genes: Total Chemical Synthesis of Two Different Versions of the Bovine Prochymosin Gene", Gene, Elsevier Science Publishers, vol. 60, No. 1, pp. 115-127.

Dorothea Wyrambik et al., "Purification and Properties of Isoenzymes of Cinnamyl-Alcohol Dehydrogenase from Soybean-Cell-Suspension Cultures", European Journal of Biochemistry, Springer-Verlag, Nov. 1975, vol. 59, No. 1, pp. 9-15.

Nabila Yahiooui et al., "Comparative Efficiency of Different Constructs for Down Regulation of Tobacco Cinnamyl Alcohol Dehydrogenase", Phytochemistry, Elsevier Science Ltd., 1998, vol. 49, No. 2, pp. 295-306.

U.S. Appl. No. 60/476,222, filed Jun. 6, 2003, Chang et al.

Aronen, Tuija, Genetic transformation of scots pine (Pinus sylvestris L.), Dissertation Metsäntutkimuslaitoksen tiedonantoja 595, 1996, pp. 8-53.

Ausubel, et al., (eds.), "Current Protocols in Molecular Biology", (John Wiley & Sons, Inc.), (1990).

Ausubel, et al., (eds.), "Short Protocols in Molecular Biology", 3rd ed. (John Wiley & Sons, Inc.), (1995).

Bugos et al., "cDNA cloning, sequence analysis and seasonal expression of lignin-bispecific caffeic acid/5-hydroxyferulic acid O-methyltransferase of aspen," Plant Molecular Biology, vol. 17, 1991, pp. 1203-1215.

Ellis et al., "Stable transformation of Picea glauca by Particle Acceleration," Biotechnology, vol. 11, Jan. 1993, pp. 84-89.

Gleave et al., "A versatile binary vector system with a T-DNA organizational structure conductive to efficient integration of cloned DNA into plant genome," Plant Molecular Biology, vol. 20, 1992, pp. 1203-1207.

Gowri et al., Stress Responses in Alfalfa (Medicago sativa L.), Plant Physiol., vol. 97, 1991, pp. 7-14.

Huang et al., "Agrobacterium rhizogenes-mediated genetic transformation and regeneration of a conifer: Larix decidua," In Vitro Cell. Dev. Biol., vol. 27P, Oct. 1991, pp. 201-207.

Izawa et al., "Plant bZIP Protein DNA Binding Specificity," J. Mol. Biol., vol. 230, 1993, pp. 1131-1144.

Kawaoka et al., "Functional analysis of tobacco LIM protein Ntlin1 involved in lignin biosynthesis," The Plant Journal, vol. 22, No. 4, 2000, pp. 289-301.

Marita et al., "NMR characterization of lignins from transgenic poplars with suppressed caffeic acid O-methyltransferase activity," J. Chem. Soc. Perkin Trans. 1, 2001, pp. 2939-2945.

Menkens et al., "The G-box: a ubiquitous regulatory DNA element in plants in plants bound by the GBF family of bZIP proteins," TIBS, Dec. 1995, pp. 506-510.

Pearson, et al., Proc. Natl. Acad. Sci., vol. 85, pp. 2444-2448, (1988) USA.

Pearson, Methods in Enzymol., vol. 183, pp. 63-98, (1990).

Perera, J.R., et al., US-09/598401C-113, sequence alignment between Seq Id No. 3 and Seq Id No. 113 of U.S. Patent No. 6,596,925, issued Jul. 2003.

Ringli et al., "Specific interaction of the tomato bZIP transcription factor VSF-1 with a non-palindromic DNA sequence that controls vascular gene expression," Plant Molecular Biology, vol. 37, 1998, pp. 977-988.

Sambrook & Russel, " Molecular Cloning: A Laboratory Manual", 3$^{rd}$ Ed., Cold Spring Harbor Laboratory Press, Cold Spring Harbor, NY, (2001).

* cited by examiner

US 7,442,786 B2

VASCULAR-PREFERRED PROMOTERS

CROSS-REFERENCE TO RELATED APPLICATION

This application claims the benefit of U.S. Provisional Application No. 60/428,287, filed Nov. 22, 2002.

FIELD OF INVENTION

The present invention relates to the regulation of polynucleotide transcription and/or expression. In particular, this invention relates to polynucleotide regulatory sequences isolated from *Eucalyptus grandis* and *Pinus radiata* that confer vascular-preferred transcription of polynucleotides in plant cells. Constructs and methods for using the inventive regulatory sequences for modifying transcription of endogenous and/or heterologous polynucleotides also are included in the invention.

BACKGROUND OF THE INVENTION

A major goal in the forestry and paper industries is the control of lignin content in plants. Lignin is a complex polymer of cinnamyl alcohols that is responsible for wood's mechanical strength, coloration, and resistance to rot. Tree species synthesize large quantities of lignin, with lignin constituting between 20% to 30% of the dry weight of wood. In addition to providing rigidity, lignin aids water transport by rendering cell walls hydrophobic and water-impermeable. It follows that increasing the lignin concentration in trees can prove beneficial for certain applications, such as providing trees with improved disease resistance or increased strength for use in construction. Lignin is also useful as a fuel, and lignin together with increased cellulose content is desirable in wood or other biomass used as fuel, such as wood for charcoal production, corn stover, and trees such as willow and fast growing aspen hybrids used for biofuels.

Conversely, the high concentration of lignin in trees presents a significant problem for the paper industry, which must expend considerable resources to separate lignin from cellulose fiber. In the U.S. alone, about 20 million tons of lignin are removed from wood per year. Further, the content of lignin is largely responsible for the digestibility, or lack thereof, of forage crops, with small increases in plant lignin content resulting in relatively high decreases in digestibility. For example, crops with reduced lignin content provide more efficient forage for cattle, with the yield of milk and meat being higher relative to the amount of forage crop consumed. Lignin content increases during plant growth, so that farmers must choose between harvesting crops early to obtain a lower yield of more digestible crops or later to obtain a higher yield of less digestible material.

For these reasons, the control of lignin content or composition through genetic modification of plants is desirable. Considerable effort has been made to this end to identify and characterize the genes responsible for lignin biosynthesis and to determine sequences that regulate their expression. Polynucleotides encoding many of the enzymes involved in lignin biosynthesis have been cloned, including cinnamyl alcohol dehydrogenase (CAD), cinnamate 4-hydroxylase (C4H), coumarate 3-hydroxylase (C3H), phenolase (PNL), O-methyl transferase (OMT), cinnamoyl-CoA reductase (CCR), phenylalanine ammonia-lyase (PAL), 4-coumarate:CoA ligase (4CL) and peroxidase (POX) from pine. U.S. Pat. No. 6,204,434.

Manipulation of the expression of these genes has been used to modify lignin content. Such experiments include altering the number of copies of genes encoding CAD, coniferin β-glucosidase (CBG), and caffeic acid 3-O-methyltransferase (COMT). U.S. Pat. No. 5,451,514, WO 94/23044, and Dharmawardhana et al., *Plant Mol. Biol.* 40: 365-72 (1999). Furthermore, antisense expression of sequences encoding CAD in poplar, *N. tabacum*, and pine leads to the production of lignin having a modified composition. Grand et al., *Planta (Berl.)* 163: 232-37 (1985), Yahiaoui et al., *Phytochemistry* 49: 295-306 (1998), and Baucher et al., *Plant Physiol.* 112: 1479 (1996), respectively.

Another major goal of the forest products, paper, plant biomass and forage industries is to increase the size of the stem, to manipulate cellulose content in the stem, or to manipulate characteristics of the cell wall in order to facilitate the recovery of cellulose from the stem. For example, cellulose is recovered from the xylem fibers in pulp production, and the number of xylem fibers and vessel elements, thickness of the cell walls, diameter of the cell lumens, length of the fibers, cellulose microfibril angle and other characteristics of these xylem cells determine the quality and quantity of cellulose recovered. Manipulation of genes involved in cellulose biosynthesis has been useful to increase the total biomass of plants and the yield of cellulose from the plants, while antisense expression of such genes has demonstrated effects on cell wall development. Shani Z., Shpigel, E., Roiz, L., Goren, R., Vinocur, B., Tzfira, T., Altman, A., and Shoseyov O. Cellulose binding domain increases cellulose synthase activity in Acetobacter xylinum, and biomass of transgenic plants. In: A. Altman, M. Ziv, S. Izhar, eds., Plant Biotechnology and In Vitro Biology in the 21st Century, pp. 213-218 Kluwer Academic Publishers. (1999). Modification of polysaccharides and plant cell wall by endo-1,4-β-glucanase and cellulose-binding domains has been described. Levy, I., Shani, Z. and Shoseyov O. Biomol Eng. 19: 17-30 (2002). Accordingly, the polynucleotides of the instant invention can be used to express nucleotide sequences in vascular tissue to modify cellulose biosysnthesis thereby affecting plant growth and biomass.

Genetic regulation of biochemical pathways preferably is conducted in narrowly restricted tissue types to avoid global, detrimental effects to the modified plants. For example, when the content or composition of lignin is affected by expression of a particular gene product, it may be desirable to limit the expression of the gene product to certain segments of the plant or to certain developmental stages, to avoid decreasing the plant's disease resistance. A heterologous gene may be expressed in a selected tissue by operably linking it to a tissue-preferred promoter. Suitable tissue-preferred promoters include the bean grp1.8 promoter, which is specifically active in protoxylem tracheary elements of vascular tissue. Keller et al., *EMBO J.* 8: 1309 (1989). These promoters also include the eucalyptus CAD promoter, which is preferentially expressed in lignifying zones. Feuillet et al., *Plant Mol. Biol.* 27: 651 (1995). Such tissue-preferred promoters have been used to regulate gene expression of antisense molecules in specific tissues. Van der Meer et al., *Plant Cell* 4: 253 (1992), Salehuzzaman et al., *Plant Mol. Biol.* 23: 947 (1993), and Matsuda et al., *Plant Cell Physiol.* 37: 215 (1996).

Because tissue-preferred promoters may be less active in a heterologous environment, they do not always express genes to the same levels achieved with constitutive promoters. Yahiaoui et al., *Phytochemistry* 49: 295-306 (1998). Further, the developmental window during which these promoters are active, or the spatial distribution of their activity, may limit their usefulness. Thus, there is a continuing need in the art to define additional tissue-preferred promoters, especially vascular-preferred promoters, that have desirable spatial and temporal patterns of expression. Reviewed by Grima-Pettenati et al., *Plant Science* 145: 51-65 (1999).

SUMMARY OF THE INVENTION

The present invention relates to isolated polynucleotide regulatory sequences that confer vascular-preferred gene expression. The polynucleotides of the present invention can be used for controlling the lignin content, cellulose content, size or cell wall development of a plant. The polynucleotides of the present invention may also be used for regulating biosynthesis of lignin, cellulose, and plant cell walls.

In one aspect, the present invention provides an isolated nucleic molecule comprising a polynucleotide that is capable of conferring vascular-preferred polynucleotide transcription. In one embodiment, the isolated nucleic molecule comprises a polynucleotide selected from any one of SEQ ID NO: 1-85 and functional variants thereof. In another embodiment, the functional variant has a sequence identity that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% in sequence to any one of SEQ ID NO: 1-85.

In another aspect, the present invention provides an isolated polynucleotide having a sequence selected from (a) sequences complementary to any one of SEQ ID NO: 1-85 and functional variants thereof, (b) sequences that are reverse complements to any of the sequences in SEQ ID NO: 1-85; and (c) sequences comprising at least 20 contiguous bases, which hybridizes to any of the polynucleotides of (a) or (b). In one embodiment, the present invention contemplates wherein said polynucleotide confers xylem-preferred gene expression in a plant cell. In another embodiment, the present invention provides a polynucleotide capable of upregulating or downregulating the expression of an operably-linked gene in a plant cell.

In another aspect, the present invention provides a plant cell comprising (a) at least one polynucleotide sequence that has the sequence of any one of SEQ ID NO: 1-85, and (b) a desired gene, wherein said polynucleotide and said desired gene are operably linked. In one embodiment, the desired gene encodes a polypeptide or protein. In another embodiment, the protein is an enzyme involved in the biosynthesis of cell walls. In a further embodiment, the protein is an enzyme involved in lignin biosynthesis. In another embodiment, the desired gene produces an RNA transcript. In yet another embodiment, the RNA transcript has an antisense sequence of a gene that is endogenous to a plant cell. In an further embodiment, the RNA transcript induces RNA interference of a gene that is normally expressed in a plant cell.

In another aspect, the present invention provides a plant comprising a plant cell having (a) at least one polynucleotide sequence that has the sequence of any one of SEQ ID NO: 1-85, and (b) a desired gene, wherein said polynucleotide and said desired gene are operably linked. In one embodiment, the plant is selected from angiosperms and gymnosperms.

In another embodiment, the present invention contemplates a method for regulating the lignin content of a plant, comprising cultivating the plant comprising a plant cell comprising a DNA construct that comprises (a) at least one polynucleotide sequence that has the sequence of any one of SEQ ID NO: 1-85, and (b) a desired gene, wherein said polynucleotide and said desired gene are operably linked.

In another aspect, the present invention contemplates a method for regulating cell wall development in a plant, comprising cultivating the plant comprising a plant cell comprising a DNA construct that comprises (a) at least one polynucleotide sequence that has the sequence of any one of SEQ ID NO: 1-85, and (b) a desired gene, wherein said polynucleotide and said desired gene are operably linked.

In another aspect, the present invention provides a transgenic plant comprising a polynucleotide sequence selected from any one of SEQ ID NO: 1-85 and functional variants thereof.

In one aspect, the present invention provides a method for obtaining wood, comprising (a) introducing into a plant cell of a woody plant a DNA construct comprising (i) a promoter having the sequence of any one of SEQ ID NOS: 1 to 85 or functional variants thereof and (ii) and a desired nucleic acid, wherein said promoter regulates the expression of said desired nucleic acid; (b) culturing said transformed plant cell under conditions that promote growth of a plant; and (c) obtaining wood from said plant. In one embodiment, the woody plant is selected from a species of *Eucalyptus* or *Pinus*.

The present invention also contemplates an isolated polynucleotide sequence selected from the group consisting of SEQ ID NO: 1-85, and polynuclucleotides having at least 60% sequence identity to any of these sequences. The invention also contemplates a polynucleotide having at least 65% sequence identity to any one of SEQ ID NO: 1-85. The invention further contemplates a polynucleotide having at least 70% sequence identity to any one of SEQ ID NO: 1-85. The present invention provides an isolated polynucleotide sequence having at least 75% sequence identity to any of SEQ ID NO: 1-85. The invention contemplates a polynucleotide having at least 80% sequence identity to any of SEQ ID NO: 1-85. Also provided is an isolated polynucleotide having 85% sequence identity to any one of SEQ ID NO: 1-85. The present invention contemplates sequences having at least 90% sequence identity to any one of SEQ ID NO: 1-85. Sequences having at least 95% sequence identity with any of SEQ ID NO: 1-85 are provided by the present invention.

DETAILED DESCRIPTION OF THE EMBODIMENTS

Figure 1:
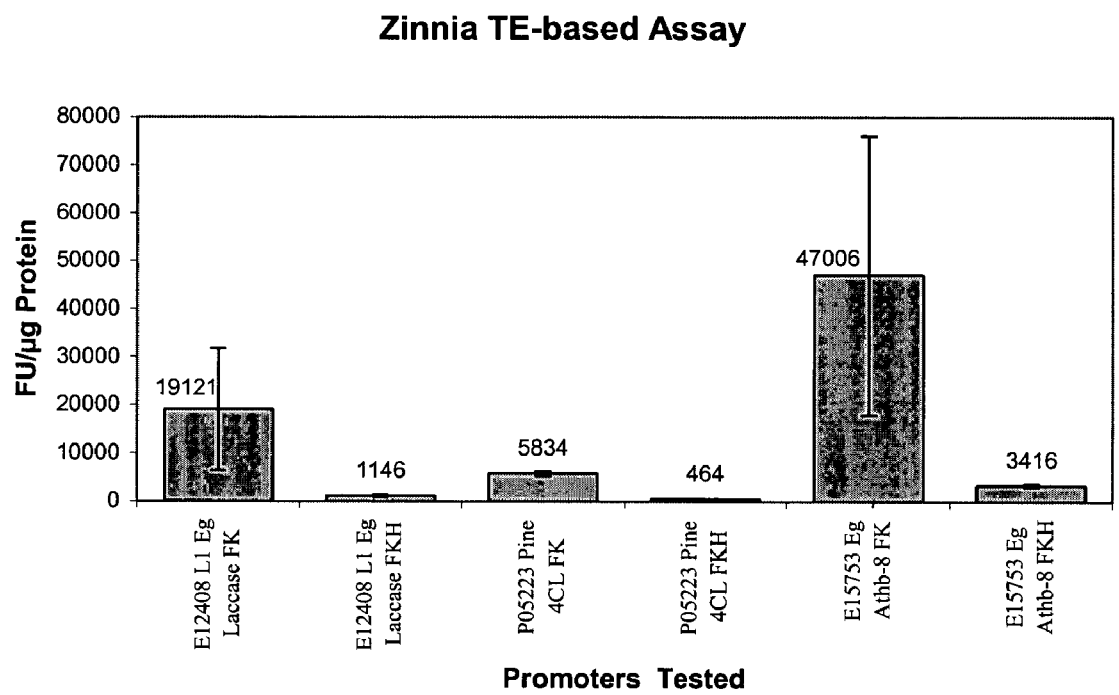
FIG. 1 depicts a Zinnia TE-based assay demonstrating three promoters having a similar expression profiles at Day 3 of culture.
Figure 2A:
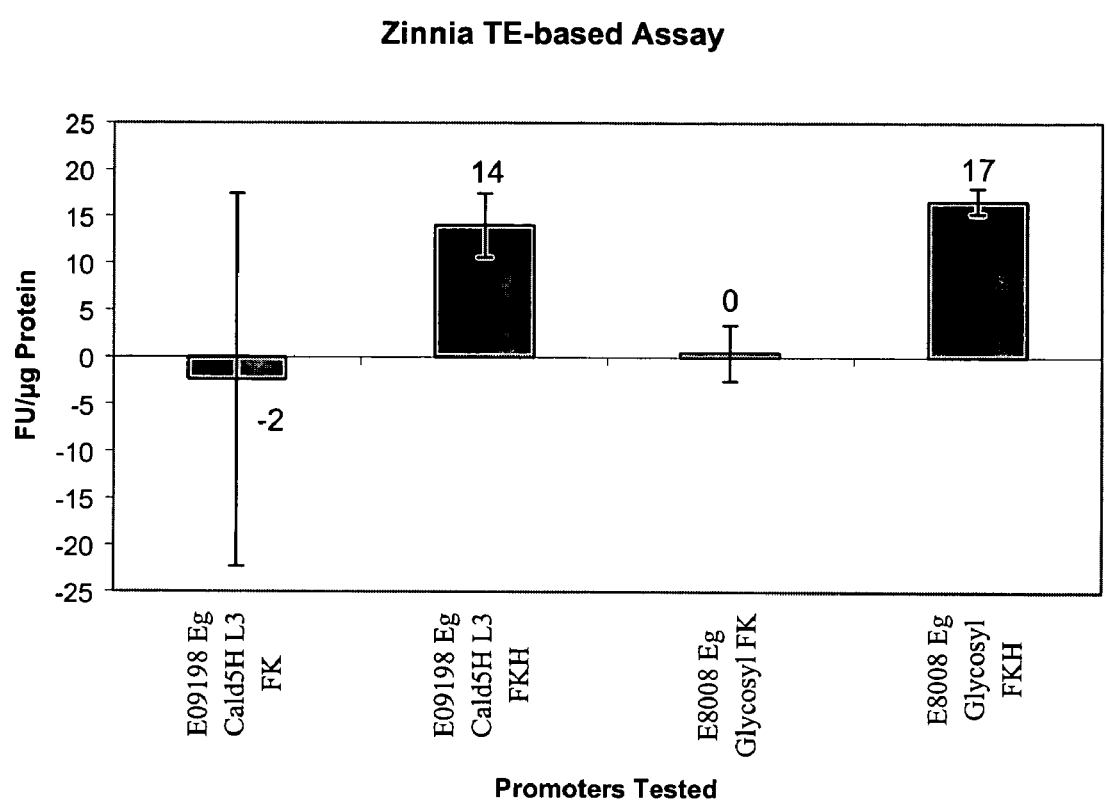
FIG. 2 depicts a Zinnia TE-based assay demonstrating two promoters having a similar expression profile at Day 3 of culture.
Figure 2B:
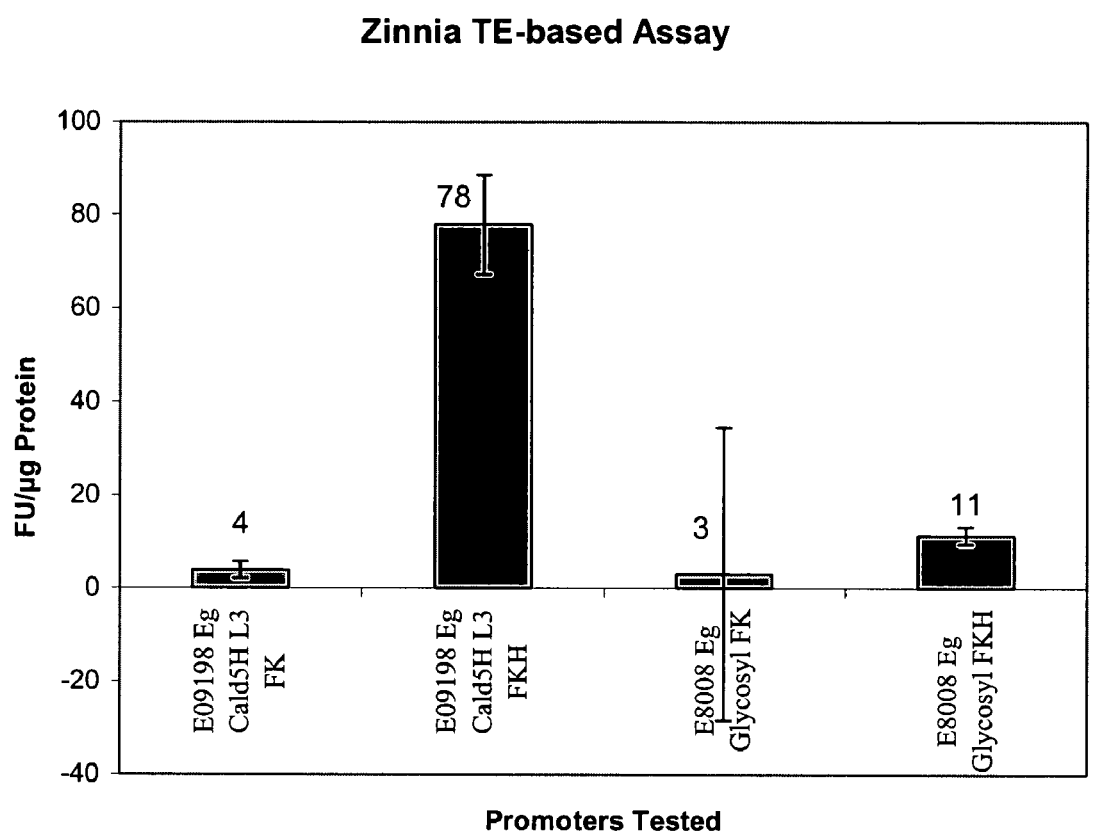
Figure 3:
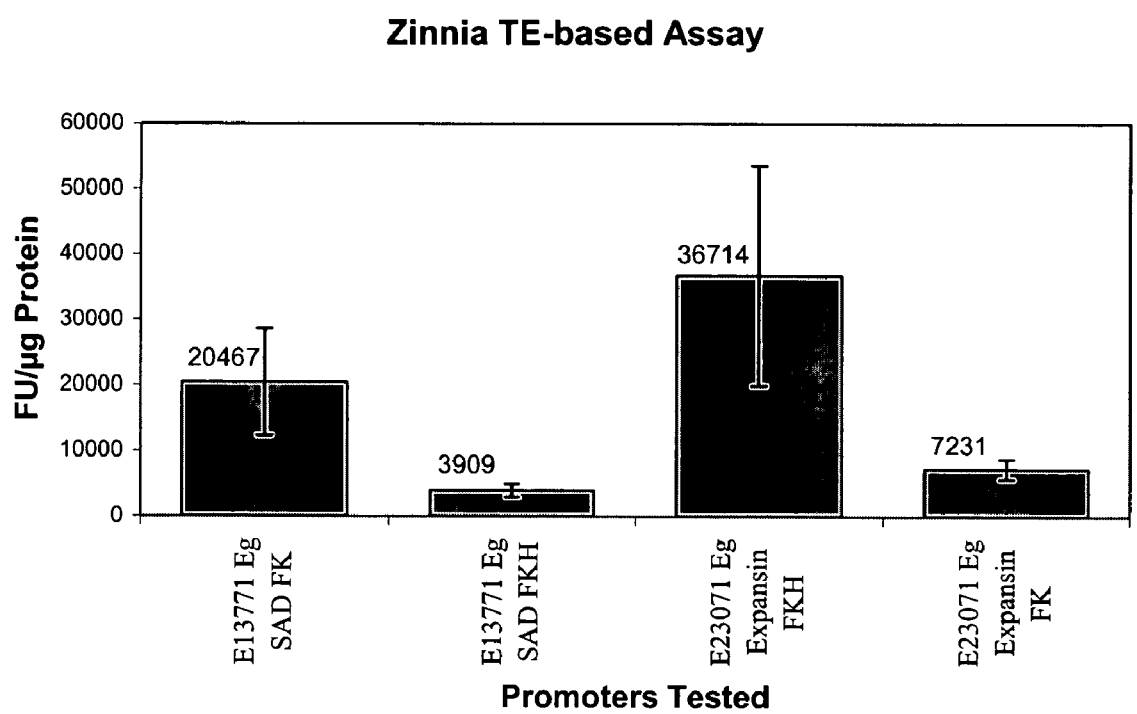
FIG. 3 depicts a Zinnia TE-based assay demonstrating two promoters having a similar expression profile at Day 3 of culture.

The present invention relates to an isolated nucleic molecule comprising a polynucleotide having a sequence at least 95% identical to a sequence selected from the group consisting of any of the polynucleotide sequences set forth in Table 6. The invention also provides functional fragments of the polynucleotide sequences disclosed in Table 6. The invention further provides complementary nucleic acids, or fragments thereof, to any of the polynucleotide sequences listed in Table 6, as well as a nucleic acid, comprising at least 15 contiguous bases, which hybridizes to any of the polynucleotide sequences disclosed in Table 6

The present invention relates to an isolated nucleic molecule comprising a polynucleotide having a sequence at least 95% identical to a sequence selected from the group consisting of any of the polynucleotide sequences set forth in Table 6. The invention also provides functional fragments of the polynucleotide sequences disclosed in Table 6. The invention further provides complementary nucleic acids, or fragments thereof, to any of the polynucleotide sequences listed in Table 6, as well as a nucleic acid, comprising at least 15 contiguous bases, which hybridizes to any of the polynucleotide sequences disclosed in Table 6.

The nucleotide sequences of the nucleic acids of the invention are provided in a sequence listing. What is intended by "SEQ ID NO: (2N+1)" are all the odd numbered sequences in the sequence listing, e.g., 1, 3, 5, 7 etc. What is intended by "SEQ ID NO: 2N" are the even numbered sequences. The difference between an odd numbered sequence, and the immediately proceeding even numbered sequence (e.g., SEQ ID NO: 1 and SEQ ID NO:2) should be that the even numbered sequence has additional bases. The last three bases of the even numbered sequences are usually ATG and represent the start codon (usually coding for methionine) for translation.

The present invention uses terms and phrases that are well known to those practicing the art. Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described herein are those well known and commonly employed in the art. Standard techniques are used for recombinant nucleic acid methods, polynucleotide synthesis, microbial culture, cell culture, tissue culture, transformation, transfection, transduction, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. The techniques and procedures are generally performed according to conventional methodology. See, e.g., Sambrook & Russel, MOLECULAR CLONING: A LABORATORY MANUAL, 3$^{rd}$ ed., Cold Spring Harbor Laboratory Press, Cold Spring Harbor, N.Y., 2001.

*Agrobacterium*: as is well known in the field, *Agrobacteria* that are used for transforming plant cells are disarmed and virulent derivatives of, usually, *Agrobacterium tumefaciens* or *Agrobacterium rhizogenes* that contain a vector. The vector typically contains a desired polynucleotide that is located between the borders of a T-DNA.

Angiosperm: vascular plants having seeds enclosed in an ovary. Angiosperms are seed plants that produce flowers that bear fruits. Angiosperms are divided into dicotyledonous and monocotyledonous plants.

Desired Polynucleotide: a desired polynucleotide of the present invention is a genetic element, such as a promoter, enhancer, or terminator, or gene or polynucleotide that is to be transcribed and/or translated in a transformed cell that comprises the desired polynucleotide in its genome. If the desired polynucleotide comprises a sequence encoding a protein product, the coding region may be operably linked to regulatory elements, such as to a promoter and a terminator, that bring about expression of an associated messenger RNA transcript and/or a protein product encoded by the desired polynucleotide. Thus, a "desired polynucleotide" may comprise a gene that is operably linked in the 5'- to 3'-orientation, a promoter, a gene that encodes a protein, and a terminator.

Alternatively, the desired polynucleotide may comprise a gene or fragment thereof in an "antisense" orientation, the transcription of which produces nucleic acids that may form secondary structures that affect expression of an endogenous gene in the plant cell. A desired polynucleotide may also yield a double-stranded RNA product upon transcription that initiates RNA interference of a gene to which the desired polynucleotide is associated. A desired polynucleotide of the present invention may be positioned within a T-DNA, such that the left and right T-DNA border sequences flank or are on either side of the desired polynucleotide. The present invention envisions the stable integration of one or more desired polynucleotides into the genome of at least one plant cell. A desired polynucleotide may be mutated or may be a variant of its wild-type sequence. It is understood that all or part of the desired polynucleotide can be integrated into the genome of a plant. It also is understood that the term "desired polynucleotide" encompasses one or more of such polynucleotides. Thus, a T-DNA of the present invention may comprise one, two, three, four, five, six, seven, eight, nine, ten, or more desired polynucleotides.

Dicotyledonous plant (dicot): a flowering plant whose embryos have two seed halves or cotyledons, branching leaf veins, and flower parts in multiples of four or five. Examples of dicots include but are not limited to, *Eucalyptus, Populus, Liquidamber, Acacia*, teak, mahogany, cotton, tobacco, *Arabidopsis*, tomato, potato sugar beet, broccoli, cassava, sweet potato, pepper, poinsettia, bean, alfalfa, soybean, carrot, strawberry, lettuce, oak, maple, walnut, rose, mint, squash, daisy, geranium, avocado, and cactus.

Endogenous refers to a gene that is native to a plant genome.

Fiber composition: as used herein, fiber composition refers to a trait that can be modified to change the structure, appearance, or use of fiber. Traits that determine fiber composition include but are not limited to fiber length, coarseness, strength, color, cross-sectional width, and fiber density. For example, it is known that fiber length imparts strength, whereas fiber coarseness is a determinant of texture and flexibility.

Foreign: "foreign," with respect to a nucleic acid, means that that nucleic acid is derived from non-plant organisms, or derived from a plant that is not the same species as the plant to be transformed or is not derived from a plant that is not interfertile with the plant to be transformed, or does not belong to the species of the target plant. According to the present invention, foreign DNA or RNA may include nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product.

Gene: A gene is a segment of a DNA molecule that contains all the information required for synthesis of a product, polypeptide chain or RNA molecule, and includes both coding and non-coding sequences.

Genetic element: a "genetic element" is any discreet nucleotide sequence including, but not limited to, a promoter, a gene, a terminator, an intron, an enhancer, a spacer, a 5'-untranslated region, a 3'-untranslated region, or a recombinase recognition site.

Genetic modification: stable introduction of DNA into the genome of certain organisms by applying methods in molecular and cell biology.

Gymnosperm: as used herein, refers to a seed plant that bears seed without ovaries. Examples of gymnosperms include conifers, cycads, ginkgos, and ephedras.

Introduction: as used herein, refers to the insertion of a nucleic acid sequence into a cell, by methods including infection, transfection, transformation or transduction.

Juvenility: describes a physiological difference between a young tree and a mature tree. In the present invention, juvenility refers to differences in microfibril angle, wood density, cellulose yield, regenerability, and reproductive ability between a young tree and a mature tree. For example, it has been shown that as a woody plant tissue matures, the tissue loses its ability to regenerate.

Lignin: as used herein, refers to a polymeric composition composed of phenylpropanoid units, including polymerized derivatives of monolignols coniferyl, coumaryl, and sinapyl alcohol. Lignin quality refers to the ability of a lignin composition to impart strength to cell wall matrices, assist in the transport of water, and/or impede degradation of cell wall polysaccharides. Lignin composition or lignin structure may be changed by altering the relative amounts of each of monolignols or by altering the type of lignin. For example, guaiacyl lignins (derived from ferulic acid) are prominent in softwood species, whereas guaiacyl-syringyl lignins (derived from ferulic acid and sinapic acid) are characteristic of hardwood species. The degradation of lignin from softwoods, such as pine, requires substantially more alkali and longer incubations, compared with the removal of lignin from hardwoods. Lignin composition may be regulated by either up-regulation or down-regulation of enzymes involved lignin biosynthesis. For example, key lignin biosynthsesis enzymes include, but are not limited to, 4-coumaric acid: coenzyme A ligase (4CL), Cinnamyl Alcohol dehydrogenase (CAD), and Sinapyl Alcohol Dehydrogenase (SAD).

Monocotyledonous plant (monocot): a flowering plant having embryos with one cotyledon or seed leaf, parallel leaf veins, and flower parts in multiples of three. Examples of monocots include, but are not limited to turfgrass, maize, rice, oat, wheat, barley, sorghum, orchid, iris, lily, onion, and palm. Examples of turfgrass include, but are not limited to *Agrostis* spp. (bentgrass species including colonial bentgrass and creeping bentgrasses), *Poa pratensis* (kentucky bluegrass), *Lolium* spp. (ryegrass species including annual ryegrass and perennial ryegrass), *Festuca arundinacea* (tall fescue) *Festuca rubra commutata* (fine fescue), *Cynodon dactylon* (common bermudagrass varieties including Tifgreen, Tifway II, and Santa Ana, as well as hybrids thereof); *Pennisetum clandestinum* (kikuyugrass), *Stenotaphrum secundatum* (st. augustinegrass), *Zoysia japonica* (zoysiagrass), and *Dichondra micrantha*.

Operably linked: combining two or more molecules in such a fashion that in combination they function properly in a plant cell. For instance, a promoter is operably linked to a structural gene when the promoter controls transcription of the structural gene.

Phenotype: phenotype is a distinguishing feature or characteristic of a plant, which may be altered according to the present invention by integrating one or more "desired polynucleotides" and/or screenable/selectable markers into the genome of at least one plant cell of a transformed plant. The "desired polynucleotide(s)" and/or markers may confer a change in the phenotype of a tranformed plant by modifying any one of a number of genetic, molecular, biochemical, physiological, morphological, or agronomic characteristics or properties of the transformed plant cell or plant as a whole. Thus, expression of one or more, stably integrated desired polynucleotide(s) in a plant genome may yield a phenotype selected from the group consisting of, for example, increased drought tolerance, enhanced cold and frost tolerance, improved vigor, enhanced color, enhanced health and nutritional characteristics, improved storage, enhanced yield, enhanced salt tolerance, enhanced heavy metal tolerance, increased disease tolerance, increased insect tolerance, increased water-stress tolerance, enhanced sweetness, improved vigor, improved taste, improved texture, decreased phosphate content, increased germination, increased micronutrient uptake, improved starch composition, improved flower longevity, altered density, altered stem strength or stem stiffness, increased dimensional stability, and altered cellulose or lignin content.

Plant tissue: a "plant" is any of various photosynthetic, eukaryotic, multicellular organisms of the kingdom Plantae characteristically producing embryos, containing chloroplasts, and having cellulose cell walls. A part of a plant, i.e., a "plant tissue" may be transformed according to the methods of the present invention to produce a transgenic plant. Many suitable plant tissues can be transformed according to the present invention and include, but are not limited to, somatic embryos, pollen, leaves, stems, calli, stolons, microtubers, and shoots. Thus, the present invention envisions the transformation of angiosperm and gymnosperm plants such as turfgrass, wheat, maize, rice, barley, oat, sugar beet, potato, tomato, tobacco, alfalfa, lettuce, carrot, strawberry, cassava, sweet potato, geranium, soybean, oak, apple, grape, pine, fir, acacia, eucalyptus, walnut, and palm. According to the present invention "plant tissue" also encompasses plant cells. Plant cells include suspension cultures, callus, embryos, meristematic regions, callus tissue, leaves, roots, shoots, gametophytes, sporophytes, pollen, seeds and microspores. Plant tissues may be at various stages of maturity and may be grown in liquid or solid culture, or in soil or suitable media in pots, greenhouses or fields. A plant tissue also refers to any clone of such a plant, seed, progeny, propagule whether generated sexually or asexually, and descendents of any of these, such as cuttings or seed. Of particular interest are conifers such as pine, fir and spruce, monocots such as Kentucky bluegrass, creeping bentgrass, maize, and wheat, and dicots such as cotton, tomato, lettuce, *Arabidopsis*, tobacco, apple and geranium.

Plant transformation and cell culture: broadly refers to the process by which plant cells are genetically modified and transferred to an appropriate plant culture medium for maintenance, further growth, and/or further development. Such methods are well known to the skilled artisan.

Progeny: a "progeny" of the present invention, such as the progeny of a transgenic plant, is one that is born of, begotten by, or derived from a plant or the transgenic plant. Thus, a "progeny" plant, i.e., an "F1" generation plant is an offspring or a descendant of the transgenic plant produced by the inventive methods. A progeny of a transgenic plant may contain in at least one, some, or all of its cell genomes, the desired polynucleotide that was integrated into a cell of the parent transgenic plant by the methods described herein. Thus, the desired polynucleotide is "transmitted" or "inherited" by the progeny plant. The desired polynucleotide that is so inherited in the progeny plant may reside within a T-DNA construct, which also is inherited by the progeny plant from its parent. The term "progeny" as used herein also may be considered to be the offspring or descendants of a group of plants. A transgenic plant of the instant invention can be asexually reproduced to produce progeny plants.

Promoter: is intended to mean a nucleic acid, preferably DNA, that binds RNA polymerase and/or other transcription regulatory elements. As with any promoter, the promoter sequences of the current present invention will facilitate or control the transcription of DNA or RNA to generate an mRNA molecule from a nucleic acid molecule that is operably linked to the promoter. As stated earlier, the RNA generated may code for a protein or polypeptide or may code for an RNA interfering, or antisense molecule.

A promoter, as used herein, may also include regulatory elements. Conversely, a regulatory element may also be separate from a promoter. Regulatory elements confer a number of important characteristics upon a promoter region. Some elements bind transcription factors that enhance the rate of transcription of the operably linked nucleic acid. Other elements bind repressors that inhibit transcription activity. The effect of transcription factors on promoter activity may determine whether the promoter activity is high or low, i.e. whether the promoter is "strong" or "weak."

A plant promoter is a promoter capable of initiating transcription in plant cells, whether or not its origin is a plant cell. Exemplary plant promoters include, but are not limited to, those that are obtained from plants, plant viruses, and bacteria such as *Agrobacterium* or *Rhizobium* which comprise genes expressed in plant cells. Examples of promoters under developmental control include promoters that preferentially initiate transcription in certain tissues, such as xylem, leaves, roots, or seeds. Such promoters are referred to as tissue preferred promoters. Promoters which initiate transcription only in certain tissues are referred to as tissue specific promoters. A cell type specific promoter primarily drives expression in certain cell types in one or more organs, for example, vascular cells in roots or leaves. An inducible or repressible promoter is a promoter which is under environmental control. Examples of environmental conditions that may effect transcription by inducible promoters include anaerobic conditions or the presence of light. Tissue specific, tissue preferred, cell type specific, and inducible promoters constitute the class of non-constitutive promoters. A constitutive promoter is a promoter which is active under most environmental conditions, and in most plant parts.

Polynucleotide is a nucleotide sequence comprising a gene coding sequence or a fragment thereof (comprising at least 15 consecutive nucleotides, at least 30 consecutive nucleotides, or at least 50 consecutive nucleotides), a promoter, an intron, an enhancer region, a polyadenylation site, a translation initiation site, 5' or 3' untranslated regions, a reporter gene, a selectable marker or the like. The polynucleotide may comprise single stranded or double stranded DNA or RNA. The polynucleotide may comprise modified bases or a modified backbone. The polynucleotide may be genomic, an RNA transcript (such as an mRNA) or a processed nucleotide sequence (such as a cDNA). The polynucleotide may comprise a sequence in either sense or antisense orientations.

An isolated polynucleotide is a polynucleotide sequence that is not in its native state, e.g., the polynucleotide is comprised of a nucleotide sequence not found in nature, or the polynucleotide is separated from nucleotide sequences to which it typically is in proximity, or is in proximity to nucleotide sequences with which it typically is not in proximity.

Regenerability: as used herein, refers to the ability of a plant to redifferentiate from a de-differentiated tissue.

Seed: a "seed" may be regarded as a ripened plant ovule containing an embryo, and a propagative part of a plant, as a tuber or spore. Seed may be incubated prior to *Agrobacterium*-mediated transformation, in the dark, for instance, to facilitate germination. Seed also may be sterilized prior to incubation, such as by brief treatment with bleach. The resultant seedling can then be exposed to a desired strain of *Agrobacterium*.

Selectable/screenable marker: a gene that, if expressed in plants or plant tissues, makes it possible to distinguish them from other plants or plant tissues that do not express that gene. Screening procedures may require assays for expression of proteins encoded by the screenable marker gene. Examples of such markers include the beta glucuronidase (GUS) gene and the luciferase (LUX) gene. Examples of selectable markers include the neomycin phosphotransferase (NPTII) gene encoding kanamycin and genetic in resistance, the hygromycin phosphotransferase (HPT or APHIV) gene encoding resistance to hygromycin, acetolactate synthase (als) genes encoding resistance to sulfonylurea-type herbicides, genes (BAR and/or PAT) coding for resistance to herbicides which act to inhibit the action of glutamine synthase such as phosphinothricin (Liberty or Basta), or other similar genes known in the art.

Sequence identity: as used herein, "sequence identity" or "identity" in the context of two nucleic acid or polypeptide sequences includes reference to the residues in the two sequences which are the same when aligned for maximum correspondence over a specified region.

As used herein, percentage of sequence identity means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

Transcription factor: Transcription factor refers to a polypeptide sequence that regulates the expression of a gene or genes by either directly binding to one or more nucleotide sequences associated with a gene coding sequence or indirectly affecting the activity of another polypeptide(s) that bind directly to one or more nucleotide sequences associated with a gene coding sequence. A transcription factor may activate (up-regulate) or repress (down-regulate) expression of a gene or genes. A transcription factor may contain a DNA binding domain, an activation domain, or a domain for protein-protein interactions. In the present invention, a transcription factor is capable of at least one of (1) binding to a nucleic acid sequence or (2) regulating expression of a gene in a plant. Additionally, the inventive polynucleotide sequences and the corresponding polypeptide sequences function as transcription factors in any plant species, including angiosperms and gymnosperms.

Transcription and translation terminators: The expression DNA constructs of the present invention typically have a transcriptional termination region at the opposite end from the transcription initiation regulatory element. The transcriptional termination region may be selected, for stability of the mRNA to enhance expression and/or for the addition of polyadenylation tails added to the gene transcription product.

Transfer DNA (T-DNA): an *Agrobacterium* T-DNA is a genetic element that is well-known as an element capable of integrating a nucleotide sequence contained within its borders into another genome. In this respect, a T-DNA is flanked, typically, by two "border" sequences. A desired polynucleotide of the present invention and a selectable marker may be positioned between the left border-like sequence and the right border-like sequence of a T-DNA. The desired polynucleotide and selectable marker contained within the T-DNA may be operably linked to a variety of different, plant-specific (i.e., native), or foreign nucleic acids, like promoter and terminator regulatory elements that facilitate its expression, i.e., transcription and/or translation of the DNA sequence encoded by the desired polynucleotide or selectable marker.

Transformation of plant cells: A process by which a nucleic acid is stably inserted into the genome of a plant cell. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, electroporation, microinjection, polyethylene glycol-treatment, heat shock, lipofection and particle bombardment.

Transgenic plant: a transgenic plant of the present invention is one that comprises at least one cell genome in which an exogenous nucleic acid has been stably integrated. According to the present invention, a transgenic plant is a plant that may comprise only one genetically modified cell and cell genome, or it may comprise several or many genetically modified cells, or all of the cells may be genetically modified. A transgenic plant of the present invention may be one in which expression of the desired polynucleotide, i.e., the exogenous nucleic acid, occurs in only certain parts of the plant. Thus, a transgenic plant may contain only genetically modified cells in certain parts of its structure.

Variant: a "variant," as used herein, is understood to mean a nucleotide sequence that deviates from the reference (i.e., native, standard, or given) nucleotide sequence of a particular gene. The terms, "isoform," "isotype," and "analog" also refer to "variant" forms of a nucleotide sequence.

"Variant" may also refer to a "shuffled gene" such as those described in Maxygen-assigned patents. For instance, a variant of the present invention may include variants of sequences and desired polynucleotides that are modified according to the methods and rationale disclosed in U.S. Pat. No. 6,132,970, which is incorporated herein by reference.

Wood composition, as used herein, refers to a trait that can be modified to change the structure, appearance, or use of wood. While not limiting, traits that determine wood composition include cell wall thickness, cell length, cell size, lumen size, cell density, microfibril angle, tensile strength, tear strength, wood color, and length and frequency of cell division.

Wood pulp refers to fiber generated from wood having varying degrees of purification. Wood pulp can be used for producing paper, paper board, and chemical products.

It is understood that the present invention is not limited to the particular methodology, protocols, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a gene" is a reference to one or more genes and includes equivalents thereof known to those skilled in the art and so forth. Indeed, one skilled in the art can use the methods described herein to express any native gene (known presently or subsequently) in plant host systems.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vitro RNA transcripts of the DNA molecules of the present invention. Isolated nucleic acid molecules, according to the present invention, further include such molecules produced synthetically.

Nucleic acid molecules of the present invention may be in the form of RNA, such as mRNA, or in the form of DNA, including, for instance, cDNA and genomic DNA obtained by cloning or produced synthetically. The DNA or RNA may be double-stranded or single-stranded. Single-stranded DNA may be the coding strand, also known as the sense strand, or it may be the non-coding strand, also referred to as the antisense strand.

Unless otherwise indicated, all nucleotide sequences determined by sequencing a DNA molecule herein were determined using an automated DNA sequencer (such as the Model 3700 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 95% identical, more typically at least about 96% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence may be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

The present invention is also directed to fragments of the isolated nucleic acid molecules described herein. By a fragment of an isolated DNA molecule having the nucleotide sequences shown in Table 6 is intended DNA fragments at least 15 nucleotides, at least 20 nucleotides, at least 30 nucleotides in length, which are useful as diagnostic probes and primers is discussed in more detail below. Of course larger nucleic acid fragments of up to the entire length of the nucleic acid molecules of the present invention are also useful diagnostically as probes, according to conventional hybridization techniques, or as primers for amplification of a target sequence by the polymerase chain reaction (PCR), as described, for instance, in Molecular Cloning, A Laboratory Manual, 3rd. edition, edited by Sambrook, J and Russel, D. W., (2001), Cold Spring Harbor Laboratory Press, Cold Spring Harbor, N.Y., the entire disclosure of which is hereby incorporated herein by reference.

By a fragment at least 20 nucleotides in length, for example, is intended fragments which include 20 or more contiguous bases from the nucleotide sequence of the as shown in Table 6. The nucleic acids containing the nucleotide sequences listed in Table 6 can be generated using conventional methods of DNA synthesis which will be routine to the skilled artisan. For example, restriction endonuclease cleavage or shearing by sonication could easily be used to generate fragments of various sizes. Alternatively, the DNA fragments of the present invention could be generated synthetically according to known techniques.

In another aspect, the invention provides an isolated nucleic acid molecule comprising a polynucleotide which hybridizes under stringent hybridization conditions to a portion of the polynucleotide in a nucleic acid molecule of the invention described above. By a polynucleotide which hybridizes to a "portion" of a polynucleotide is intended a polynucleotide (either DNA or RNA) hybridizing to at least about 15 nucleotides, at least about 20 nucleotides, at least about 30 nucleotides, and more than 30 nucleotides of the reference polynucleotide. These fragments that hybridize to the reference fragments are useful as diagnostic probes and primers. A probe, as used herein is defined as at least about 100 contiguous bases of one of the nucleic acids in Table 6. For the purpose of the invention, two sequences hybridize when they form a double-stranded complex in a hybridization solution of 6×SSC, 0.5% SDS, 5× Denhardt's solution and 100 µg of non-specific carrier DNA. See Ausubel et al., section 2.9, supplement 27 (1994). Sequences may hybridize at "moderate stringency," which is defined as a temperature of 60° C. in a hybridization solution of 6×SSC, 0.5% SDS, 5× Denhardt's solution and 100 µg of non-specific carrier DNA. For "high stringency" hybridization, the temperature is increased to 68° C. Following the moderate stringency hybridization reaction, the nucleotides are washed in a solution of 2×SSC plus 0.05% SDS for five times at room temperature, with subsequent washes with 0.1×SSC plus 0.1% SDS at 60° C. for 1 h. For high stringency, the wash temperature is increased to 68° C. For the purpose of the invention, hybridized nucleotides are those that are detected using 1 ng of a radiolabeled probe having a specific radioactivity of 10,000 cpm/ng, where the hybridized nucleotides are clearly visible following exposure to X-ray film at −70° C. for no more than 72 hours.

As mentioned previously, the present application is directed to such nucleic acid molecules which are at least 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to a nucleic acid sequence described above. One embodiment encompasses nucleic acid molecules which are at least 95%, 96%, 97%, 98%, 99% or 100% identical to the nucleic acid sequence shown in Table 6. By a polynucleotide having a nucleotide sequence at least, for example, 95% "identical" to a reference nucleotide sequence, is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to a reference nucleotide sequence refers to a comparison made between two molecules using standard algorithms well known in the art. Although any sequence algorithm can be used to define sequence identity, for clarity, the present invention defines identity with reference to the Basis Local Alignment Search Tool (BLAST) algorithm (Altschul et al., *J. Mol. Biol.* 215:403-410 (1990)), where a promoter sequence set forth in the disclosure is used as the reference sequence to define the percentage identity of polynucleotide homologues over its length. The choice of parameter values for matches, mismatches, and inserts or deletions is arbitrary, although some parameter values have been found to yield more biologically realistic results than others.

When using BLAST or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Relatedness between two polynucleotides also may be described by reference to their ability to hybridize to form double-stranded complexes by the formation of complementary base pairs. Hybridization conditions have been described previously herein. An increase in temperature can be used to break apart these complexes. The more structurally identical two sequences are, the higher the temperature required to break them apart or "melt" them. The temperature required to melt a double-stranded complex is called the "$T_m$." The relationship between the $T_m$ and other hybridization parameters is given by:

$$T_m(° C.)=81.5+16.6(\log_{10}[Na^+])+0.41(\text{fraction } G+C)-0.63(\% \text{ formamide})-(600/l),$$

where $T_m$ is the melting temperature of a DNA duplex consisting of the probe and its target; and l=the length of the hybrid in base pairs, provided l>100 base pairs. Bolton et al., *Proc. Natl. Acad. Sci.* 48:1390 (1962). Generally, a change of 1° C. in the melting point represents from 0.7% to 3.2% difference in DNA sequence similarity. Bonner et al., *Journal of Molecular Biology* 81:123-35 (1973); McCarthy et al., In EVOLUTION OF GENETIC SYSTEMS, H. H. Smith (ed.), Brookhaven Symposium in Biology No. 23, Gordon and Breach, New York, pp. 1-43 (1972). The formation of a stable DNA duplex at 60° C. typically requires at least an 80% sequence identity between sequences. Sibley et al., *ACTA* 1: 83-121 (Proceedings of the 18th International Ornithological Congress, Moscow, Aug. 16-24, 1982, Academy of Sciences of the USSR).

The nucleic acids of the present invention confer preferential expression of polypeptides or proteins in the vascular tissue of plants. The nucleic acids of the present invention can also preferentially direct the expression of antisense RNA, or RNA involved in RNA interference (RNAi) such as small interfering RNA (siRNA), in the vascular tissue of plants, which can be useful for inhibiting or completely blocking the expression of targeted genes.

As used herein, vascular plant tissue refers to xylem, phloem or vascular cambium tissue. In one embodiment, the promoters of the invention are either "xylem-specific", "cambium-specific" and/or "phloem-specific" and direct expression of an operably linked nucleic acid segment in the xylem, cambium and/or phloem, respectively. As used herein, "coding product" is intended to mean the ultimate product of the nucleic acid that is operably linked to the promoters. For example, a protein or polypeptide is a coding product, as well as antisense RNA or siRNA which is the ultimate product of the nucleic acid coding for the antisense RNA. The coding product may also be non-translated mRNA. The terms polypeptide and protein are used interchangeably herein. Xylem-specific, for example, is intended to mean that the nucleic acid molecules of the current invention are more active in the xylem than in any other plant tissue. In one embodiment, the nucleic acids of the current invention are promoters that are active specifically in the xylem, cambium and/or phloem, meaning that the promoters are only active in the xylem, cambium, and/or phloem tissue of plants, respectively. In other words, a "xylem-specific" promoter, for example, drives the expression of a coding product such that detectable levels of the coding product are expressed only in xylem tissue of a plant. However, because of solute transport in plants, the coding product that is specifically expressed in the xylem, phloem or cambium may be found anywhere in the plant and thus its presence is not necessarily confined to xylem tissue. A vascular-preferred promoter, on the other hand can be preferentially active is any of the xylem, phloem or cambium tissues, or in at least two of the three tissue types. A vascular-specific promoter, is specifically active in any of the xylem, phloem or cambium, or in at least two of the three tissue types.

The vascular system, as used herein, comprises the xylem and phloem tissues that are used to conduct water and photosynthates in higher plants and the vascular cambium that is positioned between the xylem and phloem. As components of the vascular system, xylem and phloem are collectively referred to as vascular tissue. Vascular tissue is produced during two developmentally distinct stages. During embryogenesis and/or the post-embryogenic stage, primary vascular tissue develops from the differentiation of the apical meristem and the procambium. Secondary vascular tissue develops from the differentiation of the vascular cambium The vascular cambium is the lateral meristem positioned between the xylem and phloem and differentiates to produce secondary vascular tissue. The vascular cambium is composed of two cell types, fusiform and ray initials, which are collectively referred to as cambial initials. The division of fusiform initials results in the longitudinal or axial systems of the xylem and phloem, whereas the division of ray initials leads to the development of the transverse or ray systems. The cambial initials divide about a tangential axis, such that the xylem cells aggregate towards the interior of the axis and the phloem cells towards the periphery.

As used herein, xylem refers to the conducting tissue that transports water and mineral ions from the root system to aerial portions of the plant. Both primary and secondary xylem tissue comprises three distinct cell types, the tracheary elements, fibers, and parenchyma cells. The tracheary elements, comprising imperforate tracheids and perforate vessel elements, function in water conduction. Xylem fibers, comprising fiber tracheids and libriform fibers, impart strength and rigidity to the xylem structure. Parenchyma cells are comprised of axial and ray parenchyma cells, which are important for the storage of starch, oil, and other energy-rich molecules. Thus, a xylem-specific promoter, as contemplated in the current invention, is active in the tracheary elements, fibers, and/or parenchyma cells of the primary and/or secondary xylem.

Phloem is the plant tissue that translocates the products of photosynthesis from mature leaves to areas of growth and storage. The principal cells comprising both primary and secondary phloem tissue include sieve elements, parenchyma cells, and fibers. The sieve elements refer to the conducting elements of the phloem and are further comprised of sieve cells in gymnosperms or sieve-tube elements present in angiosperms. Sieve-tube elements form specialized structures called sieve tubes, wherein the sieve tube is comprised of a series of sieve-tube elements that are vertically arranged and interconnect through a portion of the cell wall referred to as the sieve plate. In contrast, the less specialized sieve cells, present in gymnosperms and lower vascular plants, do not interconnect to form sieve plates. Sieve cells are arranged in overlapping arrays such that conduction is facilitated through enlarged pores, called sieve areas. The sieve elements are associated with, and depend upon, specialized parenchyma cells called companion cells in angiosperms and albuminous cells in gymnosperms. Both companion and albuminous cells provide storage for proteins and metabolites necessary for sieve element function. In addition to the specialized parenchyma cells, the phloem contains parenchyma cells that function in the accumulation and storage of starch, fat, and other compounds. Phloem fibers impart strength to the phloem structure and may contribute to starch storage. Thus, a phloem-specific promoter, as contemplated in the present invention, is active in the sieve elements, parenchyma cells, and/or fibers of the primary and/or secondary phloem.

In most higher plants, the vascular tissues appear as a cylinder positioned between ground tissue. In both the stem and root, the pith and cortex comprise the ground tissue. The pith is located in the interior of vascular cylinder, whereas the cortex is located between the epidermis and the vascular tissue. Collectively, the vascular system and associated ground tissues are termed the vascular cylinder.

As used herein, promoter is intended to mean a nucleic acid, preferably DNA, that binds RNA polymerase and/or other transcription regulatory elements. As with any promoter, the promoters of the current invention will facilitate or control the transcription of DNA or RNA to generate an mRNA molecule from a nucleic acid molecule that is operably linked to the promoter. As stated earlier, the RNA generated may code for a protein or polypeptide or may code for an RNA interfering, or antisense molecule. As used herein, "operably linked" is meant to refer to the chemical fusion, ligation, or synthesis of DNA such that a promoter-nucleic acid sequence combination is formed in a proper orientation for the nucleic acid sequence to be transcribed into an RNA segment. The promoters of the current invention may also contain some or all of the 5' untranslated region (5' UTR) of the resulting mRNA transcript. On the other hand, the promoters of the current invention do not necessarily need to possess any of the 5' UTR.

A promoter, as used herein, may also include regulatory elements. Conversely, a regulatory element may also be separate from a promoter. Regulatory elements confer a number of important characteristics upon a promoter region. Some elements bind transcription factors that enhance the rate of transcription of the operably linked nucleic acid. Other elements bind repressors that inhibit transcription activity. The integrated effect of transcription factors on promoter activity may determine whether the promoter activity is high or low, i.e. whether the promoter is "strong" or "weak." Transcription factors that bind regulatory elements may themselves be regulated by the interaction with other bound proteins or by covalent modification, e.g. phosphorylation, in response to extracellular stimuli. The activity of some transcription factors is modulated by signaling molecules, such as intracellular metabolites or chemicals exogenous to the organism that communicate with the cellular nucleus. Promoters that are unaffected by changes in the cellular environment are referred to as constitutive promoters.

The present invention also provides vectors comprising the isolated nucleic acid molecules of the invention. In one embodiment, the vectors of the present invention are Ti-plasmids derived from the *A. tumefaciens*.

In developing the nucleic acid constructs of this invention, the various components of the construct or fragments thereof will normally be inserted into a convenient cloning vector, e.g., a plasmid that is capable of replication in a bacterial host, e.g., *E. coli*. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. to tailor the components of the desired sequence. Once the construct has been completed, it may then be transferred to an appropriate vector for further manipulation in accordance with the manner of transformation of the host cell.

A recombinant DNA molecule of the invention typically includes a selectable marker so that transformed cells can be easily identified and selected from non-transformed cells. Examples of such markers include, but are not limited to, a neomycin phosphotransferase (nptII) gene (Potrykus et al. (1985), Mol. Gen. Genet. 199:183-188), which confers kanamycin resistance. Cells expressing the nptII gene can be selected using an appropriate antibiotic such as kanamycin or G418. Other commonly used selectable markers include the bar gene, which confers bialaphos resistance; a mutant EPSP synthase gene (Hinchee et al., Bio/Technology 6:915-922 (1988)), which confers glyphosate resistance; a nitrilase gene, which confers resistance to bromoxynil (Stalker et al. (1988) J. Biol. Chem. 263:6310-6314); a mutant acetolactate synthase gene (ALS), which confers imidazolinone or sulphonylurea resistance (European Patent Application 154,204, 1985); and a methotrexate resistant DHFR gene (Thillet et al. (1988) J. Biol. Chem. 263:12500-12508).

Additionally, vectors may include an origin of replication (replicons) for a particular host cell. Various prokaryotic replicons are known to those skilled in the art, and function to direct autonomous replication and maintenance of a recombinant molecule in a prokaryotic host cell.

The vectors will preferably contain selectable markers. Numerous selectable markers for use in selecting transfected plant cells including, but not limited to, kanamycin, glyphosate resistance genes, and tetracycline or ampicillin resistance for culturing in *E. coli*, *A. tumefaciens* and other bacteria.

A plasmid vector suitable for the introduction of nucleic acid of the current invention into monocots using microprojectile bombardment is composed of the following: the promoter of choice; an intron that provides a splice site to facilitate expression of the gene, such as the Hsp70 intron (PCT Publication WO 93/19189); and a 3' polyadenylation sequence such as the nopaline synthase 3' sequence (NOS 3'; Fraley et al. (1983) Proc Natl Acad Sci USA 80: 4803-4807). This expression cassette may be assembled on high copy replicons suitable for the production of large quantities of DNA.

A particularly useful *Agrobacterium*-based plant transformation vector for use in transformation of dicotyledonous plants is plasmid vector pMON530 (Rogers et al. (1987) Improved vectors for plant transformation: expression cassette vectors and new selectable markers. In Methods in Enzymology. Edited by R. Wu and L. Grossman. p253-277. San Diego: Academic Press). Plasmid pMON530 is a derivative of pMON505 prepared by transferring the 2.3 kb StuI-HindIII fragment of pMON316 (Rogers et al. (1987) Improved vectors for plant transformation: expression cassette vectors and new selectable markers. In Methods in Enzymology. Edited by R. Wu and L. Grossman. p253-277. San Diego: Academic Press) into pMON526. Plasmid pMON526 is a simple derivative of pMON505 in which the SmaI site is removed by digestion with XmaI, treatment with Klenow polymerase and ligation. Plasmid pMON530 retains all the properties of pMON505 and the CaMV35S-NOS expression cassette and now contains a unique cleavage site for SmaI between the promoter and polyadenylation signal.

Binary vector pMON505 is a derivative of pMON200 (Rogers et al., 1987) in which the Ti plasmid homology region, LIH, has been replaced with a 3.8 kb HindIII to SmaI segment of the mini RK2 plasmid, pTJS75 (Schmidhauser and Helinski. (1985) J. Bacteriol. 164-155). This segment contains the RK2 origin of replication, oriV, and the origin of transfer, oriT, for conjugation into *Agrobacterium* using the tri-parental mating procedure (Horsch and Klee. (1986) Proc. Natl. Acad. Sci. U.S.A. 83:4428-4432). Plasmid pMON505 retains all the important features of pMON200 including the synthetic multi-linker for insertion of desired DNA fragments, the chimeric NOS/NPTII'/NOS gene for kanamycin resistance in plant cells, the spectinomycin/streptomycin resistance determinant for selection in *E. coli* and *A. tumefaciens*, an intact nopaline synthase gene for facile scoring of transformants and inheritance in progeny, and a pBR322 origin of replication for ease in making large amounts of the vector in *E. coli*. Plasmid pMON505 contains a single T-DNA border derived from the right end of the pTiT37 nopaline-type T-DNA. Southern blot analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

Another particularly useful Ti plasmid cassette vector is pMON17227. This vector is described in PCT Publication WO 92/04449 and contains a gene encoding an enzyme conferring glyphosate resistance (denominated CP4), which is an excellent selection marker gene for many plants, including potato and tomato. The gene is fused to the *Arabidopsis* EPSPS chloroplast transit peptide (CTP2), and expression is driven by the promoter of choice.

For secretion of the translated protein into the lumen of the endoplasmic reticulum, the periplasmic space or into the extracellular environment, appropriate secretion signals may be incorporated into the expressed polypeptide. The signals may be endogenous to the polypeptide or they may be heterologous signals.

In one embodiment, the vectors of the current invention are designed in a manner such that the nucleic acids described herein are tissue-specific promoters which are operably linked to DNA encoding a polypeptide of interest. In another embodiment, the polypeptide of interest is an enzyme involved in lignin biosynthesis in plants. Polynucleotides encoding many of the enzymes involved in lignin biosynthesis include, but are not limited to, cinnamyl alcohol dehydrogenase (CAD), cinnamate 4-hydroxylase (C4H), coumarate 3-hydroxylase (C3H), phenolase (PNL), O-methyl transferase (OMT), cinnamoyl-CoA reductase (CCR), phenylalanine ammonia-lyase (PAL), 4-coumarate:CoA ligase (4CL) and peroxidase (POX) from pine. U.S. Pat. No. 6,204,434. Other enzymes include coniferin β-glucosidase (CBG), and caffeic acid 3-O-methyltransferase (COMT). U.S. Pat. No. 5,451,514, WO 94/23044, and Dharmawardhana et al., *Plant Mol. Biol.* 40: 365-72 (1999).

In another embodiment, the coding sequence operably linked to the promoter may code for a gene product that inhibits the expression or activity of enzymes involved in lignin biosynthesis. For example, of particular interest for control of lignin biosynthesis is an antisense gene for cinnamyl alcohol dehydrogenase (CAD), cinnamate 4-hydroxylase (C4H), coumarate 3-hydroxylase (C3H), phenolase (PNL), O-methyl transferase (OMT), cinnamoyl-CoA reductase (CCR), phenylalanine ammonia-lyase (PAL), 4-coumarate:CoA ligase (4CL) and peroxidase (POX) from pine.

In a further embodiment, the vectors of the current invention are designed such that the nucleic acids of the current invention are operably linked to DNA or RNA that encodes antisense RNA or interfering RNA, which corresponds to genes that code for polypeptides of interest, resulting in a decreased expression of targeted gene products. Preferably the gene products targeted for suppression are enzymes involved in lignin biosynthesis, as discussed previously. The use of RNAi inhibition of gene expression is described generally in Paddison et al., *Genes & Dev.* 16: 948-958 (2002), and the use of RNAi to inhibit gene expression in plants is specifically described in WO 99/61631, both of which are herein incorporated by reference.

The use of antisense technology to reduce or inhibit the expression of specific plant genes has been described, for example in European Patent Publication No. 271988. Reduction of gene expression led to a change in the phenotype of the plant, either at the level of gross visible phenotypic difference, for example a lack of lycopene synthesis in the fruit of tomato leading to the production of yellow rather than red fruit, or at a more subtle biochemical level, for example, a change in the amount of polygalacturonase and reduction in depolymerisation of pectins during tomato fruit ripening (Smith et. al., Nature, 334:724-726 (1988); Smith et. al., Plant Mol. Biol., 14:369-379 (1990)). Thus, antisense RNA has been demonstrated to be useful in achieving reduction of gene expression in plants.

In one embodiment of the method of making a plant of the invention, an exogenous DNA capable of being transcribed inside a plant to yield an antisense RNA transcript is introduced into the plant, e.g., into a plant cell. The exogenous DNA can be prepared, for example, by reversing the orientation of a gene sequence with respect to its promoter. Transcription of the exogenous DNA in the plant cell generates an intracellular RNA transcript that is "antisense" with respect to that gene.

For example, antisense technology may be used to suppress the expression of gene encoding enzymes involved in lignin biosynthesis, such as 4CL. A construct containing an antisense 4CL DNA sequence can be prepared by reversing the orientation of an exogenous DNA sequence encoding 4CL and operably linking the sequence to a promoter. Transcription of the exogenous 4CL DNA sequence in the plant cell would generate a 4CL RNA transcript that is in the antisense orientation.

The invention also provides host cells which comprise the vectors of the current invention. As used herein, a host cell refers to the cell in which the coding product is ultimately expressed. Accordingly, a host cell can be an individual cell, a cell culture or cells as part of an organism. The host cell can also be a portion of an embryo, endosperm, sperm or egg cell, or a fertilized egg.

The polynucleotides or vectors containing the polynucleotides of the current invention are introduced into the host cells by standard procedures known in the art for introducing recombinant vector DNA into the target host cell. Such procedures include, but are not limited to, transfection, infection, transformation, natural uptake, electroporation, biolistics and *Agrobacterium*. Methods for introducing foreign genes into plants are known in the art and can be used to insert a gene construct of the invention into a plant host, including, biological and physical plant transformation protocols. See, for example, Miki et al., 1993, "Procedure for Introducing Foreign DNA Into Plants", In: Methods in Plant Molecular Biology and Biotechnology, Glick and Thompson, eds., CRC Press, Inc., Boca Raton, pages 67-88. The methods chosen vary with the host plant, and include chemical transfection methods such as calcium phosphate, microorganism-mediated gene transfer such as *Agrobacterium* (Horsch et al., Science 227:1229-31, 1985), electroporation, micro-injection, and biolistic bombardment.

Accordingly, the present invention also provides plants or plant cells, comprising the polynucleotides or vectors comprising the polynucleotides of the current invention. In one embodiment, the plants are angiosperms or gymnosperms. In another embodiment, the plants are selected from *Eucalyptus* and *Pinus* species. In particular, the transgenic plant may be of the species *Eucalyptus grandis* and hybrids, *Pinus radiata, Pinus taeda* L (loblolly pine), *Populus nigra, Populus deltoides*, or *Liquidamber styraciflua*. Beyond the ordinary meaning of plant, the term "plants" is also intended to mean the fruit, seeds, flower, strobilus etc. of the plant. The plant of the current invention may be a direct transfectant, meaning that the vector was introduced directly into the plant, such as through *Agrobacterium*, or the plant may be the progeny of a transfected plant. The progeny may also be obtained by asexual reproduction of a transfected plant. The second or subsequent generation plant may or may not be produced by sexual reproduction, i.e., fertilization. Furthermore, the plant can be a gametophyte (haploid stage) or a sporophyte (diploid stage).

The present invention also provides a method of controlling the lignin content of a plant comprising cultivating a plant or seed comprising the vectors of the current invention. Proper cultivation to induce or sustain the growth or germination of the plants or seeds of the current invention is species-specific, and within the level of ordinary skill in the art. The setting for cultivation may be anywhere which fosters the growth or germination of the plant or seed. Furthermore, cultivation can also include steps such as, but not limited to, providing a stress treatment, (e.g., nitrogen deprivation, heat shock, low temperatures, sucrose deprivation) which can induce embryogenesis in anthers and/or microspores.

The invention further provides isolated regulatory elements that bind transcription factors and are capable of regulating tissue-preferred or tissue-specific expression. The degree of regulation conferred by the regulatory elements may be complete, meaning that transcription is not detectable without the transcription factors, or partial, meaning that transcription is enhanced in the presence of the transcription factors. In one embodiment, at least one regulatory element is operably linked to a heterologous promoter to provide a composite promoter. The composite promoter is expressed preferentially or specifically in vascular tissue. As used herein, heterologous promoters is a phrase whose meaning term that is relative to the regulatory elements. If a regulatory element and a promoter do not associate with one another in a natural setting, the promoter would be considered heterologous to the regulatory element. Typically, the precise orientation of a regulatory element within a promoter region will not affect its activity. Furthermore, regulatory elements can function normally when inserted into heterologous promoter regions. Thus, for example, xylem-preferred regulatory elements can be removed from their endogenous promoter and can be inserted into heterologous promoter regions to confer xylem-specificity or preference. Likewise, phloem-preferred regulatory elements can be removed from their endogenous promoter and can be inserted into heterologous promoter regions to confer phloem-specificity or preference. Similarly, cambium-preferred regulatory elements can be removed from their endogenous promoter and can be inserted into heterologous promoter regions to confer cambium-specificity or preference. The heterologous promoter may be, for example, a minimal CaMV 35S promoter. Promoters that direct expression in plant cells which are suitable for modification to minimal promoters include the cauliflower virus (CaMV) 35S promoter (Jefferson et al., EMBO J., 6: 3901-07 (1987)), the rice actin promoter (McElroy et al., Plant Cell, 2: 163-71 (1990)), the maize ubiquitin-1 promoter (Christensen et al., Transgenic Research, 5: 213-18 (1996)), and the nopaline synthase promoter (Kononowics et al., Plant Cell 4: 17-27 (1992)).

To prepare the nucleic acids of the invention, genomic libraries were made from Pinus radiata and Eucalyptus grandis, using a variety of restriction endonucleases to digest the genome into discrete fragments. Genomic libraries can be similarly constructed from any plant species from which it is desirable to obtain tissue-selective promoters. An adaptor was ligated to each of these genomic sequences, according to the procedure provided by Clontech for use of its GenomeWalker™ Systems (Clontech, Palo Alto, Calif.). Promoter sequences then were PCR-amplified using adaptor-specific primers and "gene-specific primers." Alternatively, this PCR amplification step optionally may be conducted by the methodology described in U.S. Pat. Nos. 5,565,340 and 5,759,822, herein incorporated by reference, to yield reaction products of long length and minimal background. Using this general PCR amplification methodology, the identification of the promoter of the invention and its identification as a tissue-selective promoter, is governed by the choice of the "gene-specific primer."

A gene-specific primer is any transcribed sequence that is expressed at high levels in a tissue of interest. In the present invention, the gene-specific primer is a fragment of, or is complementary to, an mRNA that is expressed at high levels in vascular tissue. In one embodiment, the gene-specific primer is selected by its homology to genes that are known to be expressed specifically in a particular vascular tissue type. Genes of particular interest are those that are expressed in a particular vascular tissue at high levels, which typically is an indicator of vascular-selective activity of the corresponding promoter.

Expressed sequence tags (ESTs) provide another source of gene-specific primers. An EST is a cDNA fragment of a corresponding mRNA that is present in a given library. Any plant EST database may be searched electronically to find ESTs that share identity to segments of genes that are known to be expressed specifically in a desired tissue type ("in silico screening"). These ESTs thus will provide gene-specific primers for the amplification of the promoter of the corresponding gene in a given genomic library. The amplified gene promoter need not be from the same species from which the EST database was obtained. All that is required is that the EST bears sufficient sequence similarity to the gene promoter of interest to act as a primer for PCR amplification of the target segment of the gene.

An alternative methodology to identify tissue-specific promoters rests on detection of mRNAs that are expressed in one tissue type, but not in another, implying that they are transcribed from a tissue-specific promoter. Populations of mRNAs can be distinguished on this basis by subtractive hybridization, for example. One such suitable subtractive hybridization technique is the PCR-Select™ described by Clontech.

Alternatively, a tissue-specific mRNA distribution can be determined by in situ hybridization of thin slices of plant tissue with radiolabeled probes. Probes that radioactively stain a particular tissue type are then used to detect the promoter associated with the mRNA by Southern analysis of genomic libraries, using the methodologies described below. All of the aforementioned techniques require the preparation of mRNA libraries from the tissue of interest, in this case vascular tissue. The preparation of cDNA libraries from xylem tissue, for example, is described in Dharmawardhana et al., Plant Mol. Biol. 40: 365-72 (1999) or Loopstra et al., Plant Mol. Biol. 27: 277-91 (1995). Briefly, actively differentiating xylem is first stripped from felled trees. Total RNA is isolated using standard techniques, and poly(A) RNA then is isolated and reverse transcribed to construct a xylem-tissue cDNA library. As described in Dharmawardhana (1999), for example, the cDNA library was constructed in the λZAP-XR vector, employing Strategene cDNA synthesis and GigapakII Gold™ packaging kits. Xylem-specific promoters can, in turn, be isolated from such cDNA libraries by PCR using a gene-specific probe and a primer that recognizes a sequence at the 5' end of the promoter. A gene-specific probe can be obtained by the in silico approach described above, or by designing a specific probe based on the sequence of the mRNA, if known. Furthermore, a primer can be synthesized which is complementary to the 5' UTR of the desired target gene. Alternatively, the primer can be designed from a partial amino acid sequence of the encoded protein, as a so-called degenerate primer. (See Dharmawardhana (1999)).

Following isolation of the promoter of interest, various methods can be used to characterize its tissue-specific expression pattern and promoter strength. One commonly employed method is to operably link the promoter to a readily assayed reporter gene. For example, the xylem-preferred promoter and 5' UTR of the Eucalyptus gunnii cinnamoyl-CoA reductase (EgCCR) gene (position −1448 to +200, where +1 is the transcription start site) has been operably linked to the gene encoding β-glucuronidase (GUS). Lacombe et al., Plant J. 23: 663-76 (2000). Suitable expression constructs can be made using well-known methodologies.

Transformation of plants can be accomplished by any one of many suitable techniques, including Agrobacterium-mediated transformation, as described in U.S. Pat. No. 6,051,757. Other methods for transforming trees are known in the art, as exemplified by U.S. Pat. No. 6,518,485, which discloses an accelerated particle transformation method of gymnosperm somatic embryos. Other transformation methods include micro-projectile bombardment (Klein et al., *Biotechnology* 6: 559-63 (1988)), electroporation (Dhalluin et al., *Plant Cell* 4: 1495-1505 (1992)), and polyethylene glycol treatment (Golovkin et al., *Plant Sci.* 90: 41-52 (1993)). Further, U.S. Pat. No. 6,187,994 provides for a recombinase-assisted insertion of the expression construct into a specific, selected site within a plant genome. All of the aforementioned patents and publications are herein incorporated by reference.

A DNA molecule of the present invention can be inserted into the genome of a plant by any suitable method. Suitable plant transformation vectors include those derived from a Ti plasmid of *Agrobacterium tumefaciens*, as well as those disclosed, e.g., by Herrera-Estrella et al. (1983) *Nature* 303:209, Bevan (1984) *Nucleic Acids Res.* 12 (22): 8711-8721, Klee et al. (1985) *Bio/Technology* 3(7): 637-642 and EPO publication 120,516. In addition to plant transformation vectors derived from the Ti or root-inducing (Ri) plasmids of *Agrobacterium*, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen. DNA may also be inserted into the chloroplast genome (Daniell et al. (1998) *Nature Biotechnology* 16:345-348).

When adequate numbers of cells (or protoplasts) containing the nucleic acid of interest are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, e.g., Ammirato et al. (1984) Handbook of Plant Cell Culture-Crop Species. Macmillan Publ. Co.; Fromm, M., (1990) UCLA Symposium on Molecular Strategies for Crop Improvement, Apr. 16-22, 1990. Keystone, CO.; Vasil et al. (1990) *Bio/Technology* 8:429-434; Vasil et al. (1992) *Bio/Technology* 10:667-674; Hayashimoto et al. (1990) *Plant Physiol.* 93:857-863; and Datta et al. (1990).

The vector comprising the promoter and reporter gene includes a mechanism to select those plant cells successfully transformed with the vector, which may be, for example, kanamycin resistant. The presence of the GUS gene in transformants may be confirmed by a PCR approach, using GUS-specific PCR primers (Clontech, Palo Alto). Segregation of kanamycin resistance in the progeny of the transformed plant cells can be used in conjunction with Southern analysis to determine the number of loci harboring the stably inserted vector. The temporal and spatial pattern of promoter expression is then inferred from a quantification of the reporter gene expression, as described in Jefferson et al., *EMBO J.* 6: 3901-07 (1987). Generally, GUS expression is determined histochemically in thin slices of plant tissues that are fixed first in 90% acetone and then in a buffered solution containing a GUS substrate, 5-bromo-4-chloro-3-indoyl-β-D-glucuronic acid (X-Gluc). The presence of the GUS expression product is indicated by a calorimetric reaction with the X-Gluc.

Xylem-specific expression, for example, can be conferred by the presence of regulatory elements that specifically bind transcription factors in xylem tissue. The interaction between transcription factors that influence the degree of xylem specific expression depends on the alignment between a subset of base pairs of the regulatory element with amino acid residues of the transcription factor. Likewise, phloem-specific or cambium-specific expression, for example, can be conferred by the presence of regulatory elements that specifically bind transcription factors in phloem and cambium tissue, respectively. Base pairs that do not interact with the bound transcription factor may be substituted with other base pairs, while maintaining the overall ability of the regulatory element to bind specifically the tissue-specific transcription factor.

Various methodologies can be used to identify and characterize regulatory elements that affect tissue-preferred or tissue-specific promoter activity, once a promoter is identified as tissue-preferred or specific. In one methodology, the promoter region is sequentially truncated at the 5' end and the series of truncated promoters are each operably linked to a reporter gene. When a regulatory element is deleted, the effect on the promoter activity is inferred by the loss of tissue-specific expression of the reporter gene. Alternatively, a putative regulatory element can be inserted into an expression construct containing a minimal promoter, such as the CaMV 35S minimal promoter (Keller et al., *Plant Mol. Biol.* 26: 747-56) to ascertain if the putative regulatory element confers tissue-specific expression. A minimal promoter contains only those elements absolutely required for promoter activity, such as a RNA polymerase binding site. Additional examples for elucidating putative regulatory elements are provided by studies of tissue-specific regulatory elements that coordinately regulate transcription of the genes encoding L-phenylalanine ammonia-lyase (PAL) and 4-coumarate CoA ligase (4CL). Hatton et al., *Plant J.* 7: 859-76 (1995); Leyva et al., *Plant Cell* 4: 263-71 (1992); Hauffe et al., *Plant J.* 4: 235-53 (1993); Neustaedter et al., *Plant J.* 18: 77-88 (1999), all of which are incorporated herein by reference.

Another methodology to locate putative regulatory elements is to compare sequences among known vascular-preferred or vascular-specific regulatory elements. Nucleotide comparison will identify regions similar to known tissue-preferred regulatory elements, such as, for example, vascular-preferred regulatory elements. For example, comparison of promoter sequences between cinnamyl CoA reductase and other promoters involved in phenyl-propanoid production reveals a conserved AC-rich region having the sequence CCCACCTACC (SEQ ID NO: 86). See Lacombe (2000). Conservation of the above-noted sequence in promoters involved in phenylpropanoid synthesis implies that the conserved sequence is a binding site for a coordinately activating transcription factor, such as MYB, which has been identified in several plant species. See Martin, *Trends Genet.* 13: 67-73 (1997). For example, MYB binding sites have been identified in maize ([C/A]TCC[T/A]ACC) and Petunia (TAAC[C/G]GTT or TAACTAAC). Id.

Sequence comparisons of this sort, based on the nucleic acid sequences of the invention, reveal a series of motifs shown in Table 1, below. It is expected that the motifs in Table 1 bind tissue-preferred or tissue-specific transcription factors and can be used to modulate tissue-preferred or tissue-specific expression of a heterologous, minimal promoter.

TABLE 1

| SEQ ID NO: | MOTIF | PROMOTER | |
|---|---|---|---|
| SEQ ID NO:72 | AATCAAATCCTCC | Eucalyptus Microtubule assoc | (SEQ ID NO 5) |
| SEQ ID NO:73 | AATCAAATCCTCC | Eucalyptus F5H | (SEQ ID NO 7) |
| SEQ ID NO:74 | TCTCCCTCCTCT | Eucalyptus cellulose synthase | (SEQ ID NO 8) |
| SEQ ID NO:75 | ATAAAGAAGTGAA | Eucalyptus cellulose synthase | (SEQ ID NO 8) |
| SEQ ID NO:76 | TAAACTTATTTTCT | Pine LIM | (SEQ ID NO 9) |
| SEQ ID NO:77 | TAAACTTATTTTCT | Pine Pectate Lyase | (SEQ ID NO 10) |
| SEQ ID NO:78 | GGAGAAACAAAA | Pine Pectate Lyase | (SEQ ID NO 10) |
| SEQ ID NO:79 | AAGTAACCAATGATGC | Pine Expansin | (SEQ ID NO 11) |
| SEQ ID NO:80 | ACTTTGAAGAAAA | Pine Expansin | (SEQ ID NO 11) |
| SEQ ID NO:81 | TGAGGAGAAGA | Pine 4CL3 | (SEQ ID NO 13) |
| SEQ ID NO:82 | ATCAAGCTGAT | Pine 4CL | (SEQ ID NO 13) |
| SEQ ID NO:83 | AATTTCATTTTC | Pine dirigent | (SEQ ID NO 16) |
| SEQ ID NO:84 | TAAATTTGAATTT | Eucalyptus Laccase | (SEQ ID NO 17) |

The interaction of bZIP proteins with vascular-specific or vascular-preferred promoters, for example, provides another example of how one of skill in the art can characterize regulatory elements. For example, the gene encoding glycine-rich protein, grp1.8, is expressed in a xylem-specific manner, as determined by histochemical staining of a GRP1.8-β-glucuronidase fusion protein. Keller et al., *EMBO J.* 8: 1309-14 (1989). A 5' deletion study of the grp1.8 promoter revealed a 20-base pair negative regulatory element that is essential for vascular-specific expression. Keller et al., *Plant Cell* 3: 1051-61. Similar xylem-specific regulatory elements that operate by negative tissue-specific regulation of a promoter have been identified in the bean pa12 and parsley 4CL-1. Leyva et al., *Plant Cell* 4: 263-71 (1992); Hauffe et al., *Plant J.* 4: 235-53 (1993), respectively. A transcription factor in xylem, VSF-1, specifically interacts with the 20-base pair regulatory element sequence of the grp1.8 gene. The interaction of VSF-1 and the regulatory element was demonstrated by the formation of a high molecular weight complex between VSF-1 and the regulatory element, using an electrophoretic mobility shift assay, with the specificity of binding being demonstrated by the unlabeled DNA target competing for VSF-1 binding. Torres-Schumann et al., *Plant J.* 9: 283-96 (1996). The precise residues with which VSF-1 interacts were delineated further by measuring the sensitivity of the regulatory element to DNaseI. Briefly, the interaction of VSF-1 with the regulatory element prevents DNaseI from degrading certain residues that are contacted by the protein, by virtue of steric hindrance by the bound transcription factor. Typically, the DNaseI analysis also reveals residues that become hypersensitive to degradation when the transcription factor is bound. To verify that the putative regulatory element was xylem-specific, monomers or multimers of the putative regulatory region were fused upstream of a minimal CaMV 35S or minimal grp1.8 promoter. The putative regulatory region conferred xylem-specific expression on these promoters, as determined by the histochemical analysis using a fused β-glucuronidase gene operably linked to the modified promoter, stably transfected into tobacco. See Torres-Schumann (1996).

Functional Variants or Fragments of the Promoters of the Invention

Additional variants or fragments of the promoters of the invention are those with modifications interspersed throughout the sequence. Functional variants or fragments, as used herein, are nucleic acids that have a nucleic acid sequence at least about 70% identical to the reference nucleic acid, but still confer tissue-specific expression of coding products. The tissue-specificity or preference of the functional variant must be towards the same tissue as the reference nucleic acid. However, even if the functional variant is not as preferential or as specific as the reference nucleic acid, the variant is still considered a functional variant as used herein. In one embodiment, the sequence of the functional variant or fragment is at least about 75% identical to the reference nucleic acid. In other embodiments, the sequence of the functional variant or fragment is at least about 80%, 85%, 86%, 87%, 88%, 89%, 90%, 91%, 92%, 93%, 94%, 95%, 96%, 97%, 98% or 99%.

Modifications that can produce functional variants may be made by sequential deletion of residues from the 5' end or the deletion of 5' UTR sequences from the 3' end. Alternatively, internal residues may be modified. Modifications that do not affect the function of the promoter regions most likely will be those that do not affect the binding of transcription factors. The modifications encompassed by the invention also include those that occur naturally in the form of allelic variants of the promoters of the invention. The variants of the current invention are tested for organ or tissue specific, or organ or tissue preferred activity using the methods described herein.

Methods of Making the Nucleic Acids of the Present Invention

The nucleic acids of the invention can be obtained by using well-known synthetic techniques, standard recombinant methods, purification techniques, or combinations thereof. For example, the isolated polynucleotides of the present invention can be prepared by direct chemical synthesis using the solid phase phosphoramidite triester method (Beaucage et al., *Tetra. Letts.* 22: 1859-1862 (1981)), an automated synthesizer (Van Devanter et al., *Nucleic Acids Res.* 12: 6159-

6168 (1984)), or the solid support method of U.S. Pat. No. 4,458,066. Chemical synthesis generally produces a single stranded oligonucleotide, which can be converted into double stranded oligonucleotides by hybridization with a complementary sequence, or by polymerization, using the single strand as a template. Also, longer sequences may be obtained by the ligation of shorter sequences.

Alternatively, the nucleic acids of the present invention can be obtained by recombinant methods using mutually priming oligonucleotides. See e.g Ausubel et al., (eds.), CURRENT PROTOCOLS IN MOLECULAR BIOLOGY (John Wiley & Sons, Inc. 1990). Also, see Wosnick et al., Gene 60: 115 (1987); and Ausubel et al. (eds.), SHORT PROTOCOLS IN MOLECULAR BIOLOGY, $3^{rd}$ ed., (John Wiley & Sons, Inc. 1995). Established techniques using the polymerase chain reaction provide the ability to synthesize polynucleotides at least 2 kilobases in length. Adang et al., Plant Mol. Biol. 21: 1131 (1993); Bambot et al., PCR Methods and Applications 2: 266 (1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263-268, (Humana Press, Inc. 1993); Holowachuk et al., PCR Methods Appl. 4: 299 (1995).

Methods of Using the Nucleic Acids of the Invention

The nucleic acids of the current invention are useful for altering characteristics of the plant. The nucleic acids may be operably linked to a gene of interest to increase the levels of a molecule found in the vascular tissue. Alternatively, the gene of interest may inhibit the formation of an ultimate end product, e.g. cellulose, thus the nucleic acids of the current invention can be used to decrease the levels of a predetermined molecule in vascular tissue.

One of the primary targets of such manipulated expression is the lignin biosynthetic pathway. For the reasons set forth above, there is considerable interest in regulating the amount of lignin in plants, either positively or negatively, which can be accomplished through expression of gene products that impact this pathway. For example, manipulation of the number of copies of CAD and COMT modifies lignin content, as described in U.S. Pat. No. 5,451,514 and WO 94/23044. Furthermore, antisense expression of sequences encoding CAD in poplar or pine leads to a modified lignin composition. Grand et al., Planta (Berl.) 163: 232-37 (1985); Baucher et al., Plant Physiol. 112: 1479 (1996), respectively.

Other characteristics which may be important to alter include sugars. Increasing the levels of enzymes responsible for sugar production, for example, in phloem tissue would increase the sugar content in the plants. Enzymes which may increase or decrease the levels of sugar production include, but are not limited to β-glucosidases, 1-3 β glucanase, 6-phospho-fructo-1-kinase, sucrose synthase, UDP-glucose-pyrophosphorylase, hexokinase, phosphoglucomutase, sucrose transporters, and invertases.

Additional characteristics include, but are not limited to, increasing insecticidal, antiviral or antibacterial proteins present in the leaves of the plant. Such proteins include, but are not limited to cecropins, thionins, defensin, lipid transfer proteins, hevein-like peptides, and GASA peptides. Still other characteristics include drought tolerance, cold tolerance, peroxidase activity, salt tolerance, and nitrogen transport.

The present invention, thus generally described, will be understood more readily by reference to the following examples, which are provided by way of illustration and are not intended to be limiting of the present invention.

EXAMPLES

Example 1

Isolation of Vascular-Specific Promoters

Pinus radiata and Eucalyptus grandis cDNA libraries were constructed and screened as follows. mRNA was extracted from plant tissue using the protocol of Chang et al., Plant Molecular Biology Reporter 11: 113-116 (1993) with minor modifications. Specifically, samples were dissolved in CPC-RNAXB (100 mM Tris-Cl, pH8.0; 25 mM EDTA; 2.0M NaCl; 2% CTAB; 2% PVP and 0.05% Spermidine*3 HCl) and extracted with chloroform:isoamyl alcohol 24:1.

RNA was precipitated with ethanol and purified using MessageMaker kit (Life Technologies). A cDNA expression library was constructed from purified mRNA by reverse transcriptase (Loopstra et al., Plant Mol. Biol. 27:277-291 (1995)) synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY Broth (Gibco BRL, Gaithersburg, Md.) and plated out onto LB-kanamycin agar plates containing 5-bromo-4-chloro-3-indolyl-beta-D-galactoside (X-gal) and isopropylthio-beta-galactoside (IPTG).

Colonies were picked and DNA prepared using standard miniprep technology. Colonies containing a correct insert were cultured in NZY Broth with kanamycin and cDNA was purified by means of alkaline lysis and polyethylene glycol (PEG) precipitation. Agarose gel at 1% was used to screen sequencing templates for chromosomal contamination. Dye terminator chemistry was set up using Big Dye Chemistry (Applied Biosystems), according to the manufacturer's protocol.

The DNA sequence of positive clones were obtained using a 3700 Capillary Machine (Applied Biosystems) or a Prism 377 sequencer Perkin Elmer/Applied Biosystems Division. cDNA clones were sequenced first from the 5' end, and in some cases, also from the 3' end. For some clones internal sequence was obtained using subcloned fragments. Subcloning was performed using standard procedures of restriction mapping and subcloning into pBluescript II SK+ vector.

Plant EST sequences homologous to a selected gene were identified from either a Pinus radiata or Eucalyptus grandis cDNA expression library and are displayed in Table 2.

TABLE 2

| SEQ ID NO | Gene Homology | Species | BLASTX Hit | E Value | Identity |
|---|---|---|---|---|---|
| 1 | Glucosyl Transferase | E. grandis | Glucosyl Transferase | e-130 | 214/421 (50%) |
| 2 | Ted 2 (970 bp) | E. grandis | NADP-Dependent Oxidoreductase Ted2 | e-160 | 276/324 (85%) |
| 3 | Cyclin B (447 bp) | E. grandis | Putative G2/Mitotic-Specific Cyclin 1 (B-like Cyclin) | e-122 | 242/360 (67%) |
| 4 | Cyclin B (883 bp) | E. grandis | Putative G2/Mitotic-Specific Cyclin 1 (B-like Cyclin) | e-122 | 242/360 (67%) |
| 5 | Microtubule associated | E. grandis | AT2G45170 Putative Microtubule-Associated Protein | 2.00E-53 | 100/117 (85%) |
| 6 | CAP Adenyl Cyclase Associated | E. grandis | Adenyl Cyclase Associated Protein | 0.0 | 382/476 (80%) |
| 7 | Ferulate-5-Hydroxylase | E. grandis | Ferulate-5-Hydroxylase | 0.0 | 402/517 (77%) |
| 8 | Cellulose synthase | E. grandis | Cellulose Synthase | 0.0 | 845/978 (86%) |
| 9 | LIM promoter | P. radiata | LIM Domain Protein PLIM1 | 3.00E-78 | 126/175 (72%) |
| 10 | Pectate Lyase | P. radiata | Pectate Lyase | 0.0 | 298/379 (78%) |
| 11 | Expansin | P. radiata | Alpha-Expansin | e-122 | 197/240 (82%) |
| 12 | ACC Oxidase 1 1-Aminocyclopropane-1-carboxylate oxidase | P. radiata | ACC Oxidase | 9.00E-99 | 187/321 (58%) |
| 13 | 4-Coumarate CoA Ligase 3(4CL3) (contains 5'-end 40 bp insert) | P. radiata | 4-Coumarate-CoA Ligase (EC 6.2.1.12) | 0.0 | 392/533 (73%) |
| 14 | 4CL1 or 4CL2 (650 bp) | P. radiata | 4-Coumarate-CoA Ligase (EC 6.2.1.12) | 1.00E-89 | 168/175 (96%) |
| 15 | 4CL1 or 4CL2 (1650 bp) | P. radiata | 4-Coumarate-CoA Ligase (EC 6.2.1.12) | 3.00E-89 | 168/175 (96%) |
| 16 | Dirigent Protein | P. radiata | Dirigent Protein, Putative (Hypothetical 20.6 KDa Protein) | 5.00E-41 | 77/150 (51%) |
| 17 | Laccase (898 bp) | E. grandis | Laccase Precursor (EC 1.10.3.2) | e-153 | 263/318 (82%) |
| 18 | Laccase (500 bp) | E. grandis | Laccase Precursor (EC 1.10.3.2) | e-153 | 263/318 (82%) |
| 19 | Unknown protein Euc E11912 (600 bp) | E. grandis | AT4G27438 | 8.00E-65 | 122/172 (70%) |
| 20 | Cellulose-synthase like | P. radiata | Putative Glucosyl Transferase | 0.0 | 487/690 (70%) |
| 21 | 4CL3 (without 5'-end 40 bp insert) | P. radiata | 4-Coumarate-CoA Ligase (EC 6.2.1.12) | 0.0 | 392/533 (73%) |

Polynucleotide or polypeptide sequences can be aligned with other polynucleotide and/or polypeptide sequences and the degree of shared identical sequence can be determined using computer algorithms that are publicly available. The BLAST family of algorithms, including BLASTN, BLASTP, and BLASTX, is described in the publication of Altschul et al., "Gapped BLAST and PSI-BLAST: a new generation of protein database search programs," Nucleic Acids Res. 25:3389-3402, 1997. The BLASTN algorithm Version 2.0.11 [Jan. 20, 2000] set to the default parameters described in the documentation and distributed with the algorithm, are preferred for use in the determination of polynucleotide variants according to the present invention.

BLASTX searches were performed using SWISSPROT-TREMBLE Sequences [Jul. 9, 2002] and the searches were performed on Nov. 15, 2002. The following running parameters are preferred for the determination of alignments and similarities using BLASTX that contribute to the E values and percentage identity of polypeptide sequences: blastall -p blastx -d swissprotdb -e 10 -G 0 -E 0 -FF -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -F Filter Query Sequence [String]; -v Number of one-line descriptions (v) [Integer]; -b Number of alignments to show (b) [Integer]; -I Query File [File In]; -o BLAST report Output File [File Out] Optional.

The promoters were cloned using a "Genome Walker" kit (Clontech, Palo Alto, Calif.). This is a PCR-based method, which requires four PCR primers to be constructed, two of which must be gene-specific. The gene specific primers are designed generally within the 5' UTR of the gene. The fragment is amplified and then cloned into a T-tailed vector in front of the GUS reporter gene.

Example 2

Methodology to Determine the Tissue Specificity of a Promoter

Following the identification and cloning of a promoter by the procedure outlined above in Example 1, the promoter is operably linked with a reporter gene to determine those tissue types in which the promoter is active. To this end, a construct containing an inventive promoter is transformed into *Agrobacterium tumefaciens* by electroporation. Briefly, 40 µl of diluted AgL-1 competent cells are placed on ice and are contacted with about 10 ng of pART27 vector containing the promoter sequence. Electroporation is conducted under the following parameters:

Resistance=129 ohm
Charging voltage=1.44 kV
Field strength=14.4 kV/cm
Pulse duration=5.0 ms Following electroporation, 400 µl of YEP liquid media is added and the cells are allowed to recover for one hour at room temperature. Cells then are centrifuged at 6000 rpm for 3 min and are resuspended in ~50 µl YEP. Cell samples are spread over the surface of a YEP Kan50/Rif50 plate, sealed with parafilm, and incubated at 29° C. for 2 days for colony growth.

Wild type *Arabidopsis thaliana* cv. 'Columbia-0' plants are then transformed with *Agrobacterium* containing constructs of interest by floral dip infiltration. Briefly, *Agrobacterium* cultures are centrifuged at ~8600 rcf for 10 min at 20° C. and are resuspended to an optical density of ~0.7-0.8. Plants are dipped into an infiltration solution containing the *Agrobacterium* for 5 sec. Plants are drained of excess solution and placed under grow lights in ambient conditions. After 24 hrs, the plants are misted and maintained for seed production. $T_1$ seeds are surface sterilized in 5% commercial bleach solution and plated on MS media containing Kanamycin (50 mg/l) and Timentin (250 mg/l) to select for putative transformants.

*N. benthamiana* plants are transformed with constructs of interest by *Agrobacterium*-mediated leaf tissue transformation (Burow et al., *Plant Mol. Biol. Rep.* 8:124-139, 1990).

Successfully transformed plants are then assayed for the expression of the operably linked reporter gene. Leaf, stem, root and floral regions are immersed in a staining solution (50 mM $NaPO_4$, pH 7.2, 0.5% Triton X-100, 1 mM X-Glucuronide, cycloheximide salt (Ducheffa). A vacuum is applied twice for 5 min to infiltrate the tissue with the staining solution. The tissue is then left shaking overnight at 37° C. for color development. Tissues are checked at three or four time-points to check stain development, and if samples show early development, a piece of tissue is destained in 70% ethanol. This tissue is then examined for GUS expression using a light microscope and photographed.

Example 3

Isolation and Culture of *Zinnia elegans* Mesophyll Cells in Tracheary Element (TE) Inducing (FKH) and Non-Inducing (FK) Medium Primary and secondary pair leaves from *Zinnia* seedlings were harvested from 8 punnets. Leaves were sterilized in 500 ml of 0.175% sodium hypochlorite solution for 10 minutes. Leaves were then rinsed twice in 500 ml of sterile water. Using 20-30 leaves at a time, leaves were ground in 25-30 ml of FK medium with a mortar and pestle. The cells were filtered through a 40 µm nylon mesh and a total of 90 ml of mesophyll cells were obtained in this fashion. The cells were centrifuged at 200×g for 2 minutes at 20° C. and the resultant pellet was washed once more with an equal volume of FK medium. Upon completion of the second wash, the pellet was split into two equal halves, wherein one half was washed with 45 ml of FK medium and the other with 45 ml of FKH medium. The pellets were resuspended in 60 ml of FK medium and 60 ml of FKH medium, respectively. They were cultured in the dark in two 6-well plates on the rotary shaker set at 120 rpm.

Example 4

Isolation of *Zinnia elegans* Protoplasts from Leaves or Mesophyll Cells Cultured Overnight to Three Days in FK Medium and FKH Medium Sterile *Zinnia elegans* primary leaves (6-8 in number) were cut into 1 mm slivers and placed in 15 ml of cell wall digesting enzyme mix (1% Cellulase Onozuka R-10 and 0.2% pectolyase Y23 in Protoplast isolation buffer). Mesophyll cells cultured in FK medium (40 ml) or FKH medium (40 ml) were pelleted by centrifuging at 200×g for 2 minutes at 20° C. Each pellet was resuspended in 20 ml of sterile protoplast isolation buffer containing 200 mg Cellulase Onozuka R-10 and 40 mg Pectolyase Y23. The protoplasts were isolated by incubating the cell suspensions in CellStar culture plates for 2-4 hours on a rotary shaker set at ~70 rpm at 23° C. The protoplasts were pelleted by centrifuging the contents of the plates at 200×g for 2 minutes. Each pellet was then resuspended in 20 ml of 24% sucrose solution.

Fukuda and Komamine Medium Stock Solutions

| Stock A (10X) | Stock B (400X) | Stock C (400X) | Stock D (400X) | Stock E (400X) |
|---|---|---|---|---|
| 20,200 mg KNO$_3$ | 2,500 mg MnSO$_4$•4H$_2$O | 3,700 mg Na$_2$EDTA | 200 mg Glycine | 50 mg Folic Acid |
| 540 mg NH$_4$Cl | 1,000 mg H$_3$BO$_3$ | 2,800 mg FeSO$_4$•7H$_2$0 | 10,000 mg myo-Inositol | 250 ml Milli-Q water |
| 2,470 mg MgSO$_4$•7H$_2$0 | 1,000 mg ZnSO$_4$•7H$_2$O | 250 ml Milli-Q water | 500 mg Nicotinic acid | |
| 1,470 mg CaCl$_2$•2H20 | 25 mg Na$_2$MoO$_4$•2H$_2$O | | 50 mg pyridoxine hydrochloride | |
| 680 mg KH$_2$PO$_4$ | 2.5 mg CuSO$_4$•5H$_2$0 | | 5 mg thiamine hydrochloride | |
| 1,000 ml Milli-Q water | 250 ml Milli-Q water | | 1,000 ml Milli-Q water | |

| For 1 Liter Solution | FK Medium | FKH Medium |
|---|---|---|
| Stock A | 100 ml | 100 ml |
| Stock B | 2.5 ml | 2.5 ml |
| Stock C | 2.5 ml | 2.5 ml |
| Stock D | 2.5 ml | 2.5 ml |
| Stock E | 2.5 ml | 2.5 ml |
| Sucrose | 10,000 mg | 10,000 mg |
| d-(−) Mannitol | 36,000 mg | 36,000 mg |
| 1-Naphthaleneacetic acid (NAA | | 0.1 mg |
| 6-Benzyladenine (BA) | | 0.2 mg |
| Milli-Q water | up to 1,000 ml | up to 1,000 ml |

Example 5

Transfection of *Zinnia elegans* Protoplasts

*Zinnia* protoplasts suspended in 24% sucrose solution were overlaid with 1 ml W5 solution (150 mM NaCl, 125 mM CaCl$_2$.2H$_2$O, 5 mM KCl, 5 mM sucrose, pH 5.6-6) and centrifuged at 70×g for 10 minutes at 20° C. with brakes off. Floating protoplasts were harvested, resuspended in 10 ml W5 solution, and pelleted by centrifuging at 70×g for 10 minutes at 20° C. Protoplast pellets were resuspended in MaMg medium (450 mM mannitol, 15 mM MgCl$_2$, 0.1% MES, pH 5.6) at a density ~5×10$^6$ protoplasts/ml and aliquoted into individual 15 ml tubes (300 μl: 1.5×10$^6$ protoplasts). For each construct, 5 μg DNA and 50 μg Salmon Testes DNA was added to the protoplast suspension, mixed, and incubated for 5 minutes at 20° C. Three hundered μl 40% PEG solution (40% PEG 3340, 100 mM Ca(NO$_3$)$_2$.4H$_2$O, 0.45 M mannitol, pH 9.0) was added to each protoplast aliquot, mixed, and incubated for 20 minutes at 20° C. Five ml of K3/0.4M sucrose (for 1 L solution: 4.3 g Murashige and Skoog plant salts, 100 mg Myo-inositol, 250 mg xylose, 10 mg Thiamin-HCl, 1 mg Nicotinic acid, 1 mg Pyridoxin-HCl, 1 mg NAA, 0.2 mg kinetin, 137 g sucrose, pH 5.6 adjust with KOH) was added to each aliquot of leaf-derived transfected protoplasts or transfected protoplasts from mesophyll cells cultured in FK medium and mixed. Similarly, 5 ml of K3/0.4M sucrose+0.1 ppm NAA+0.2 ppm BA was added to each aliquot of transfected protoplasts from mesophyll cells cultured in FKH medium and mixed. The transfected protoplast suspensions were incubated overnight at 23° C. in the dark.

Example 6

Harvesting of Transfected *Zinnia elegans* Protoplasts and Reporter Gene Analysis Transfected *Zinnia* protoplast suspensions, prepared as described in Example 5, were individually harvested by adding 9.5 ml of W5 solution, mixing the contents of each tube, and centrifuging at 70×g for 10 minutes at 20° C. The bulk of the supernatant was decanted and the protoplast volume was brought to 900 μl. For each 900 μL sample, 300 μL of protoplasts were aliquoted into 5 ml polystyrene round-bottom tubes, resuspended in 500 μl W5 medium, and set aside for analysis of fluorescent reporter gene expression and cell viability. The remaining 600 μL of protoplasts and solution were transferred into individual microtubes and pelleted by centrifugation at 420×g for 2 minutes at 20° C. The protoplast pellet was assayed for GUS reporter gene expression as described by Jefferson, R. A., 1987, *Plant Mol. Biol. Rep.* 5, 387. GUS (MUG) assays were performed using a Wallac (Turku, Finland) Victor[2] 1420 Multilabel Counter. Umbelliferone was detected using a 355 nm excitation filter and a 460 nm emission filter for 1 second.

Example 7

In Planta Expression Data

Three weeks post-transfer to soil, transformed *Arabidopsis* and *N. benthamiana* tissues are analyzed for GUS reporter gene expression. To assay GUS expression, leaf, root, and floral materials are immersed in the GUS solution as described in Example 2. A vacuum is applied twice for 5 minutes to infiltrate the tissue with the staining solution and the tissue is then incubated overnight in a shaker at 37° C. for color development. Following overnight incubation, the tissue samples are then destained in 70% ethanol and examined under a light microscope for GUS expression. Table 3 contains the percentage of transformed *Arabidopsis* and *N. benthamiana* plants expressing GUS.

Three months post-soil transfer, tissues from *N. benthamiana* T$_1$ plants are embedded into paraplast, sectioned with a microtome, and analyzed with a light microscope for GUS expression. The GUS localization and microtome results, as shown in Table 3, demonstrate that the disclosed isolated nucleotide sequences confer reporter gene expression preferentially in vascular cambium, xylem, and/or phloem tissues.

TABLE 3

In planta GUS Vascular Expression

| SEQ ID NO | Size (bp) | No Plants GUS+ | No Plants Tested | % GUS Expression | GUS Vascular Localization | Microtome Results |
|---|---|---|---|---|---|---|
| 1 | 168 | 2 | 12 | 16.67 | Stem material | |
| 2 | 934 | 7 | 12 | 58.33 | | Cambial cells, early xylem |
| 3 | 408 | 11 | 12 | 91.67 | Stem, developing lateral roots | Cambium, xylem |
| 4 | 847 | 11 | 12 | 91.67 | cambium | Cambium initials, lateral roots |
| 5 | 286 | 8 | 12 | 66.67 | Phloem, pith, Phloem parenchyma | |
| 6 | 216 | 4 | 12 | 33.33 | xylem | |
| 7 | 473 | 7 | 10 | 70.00 | Not specified | |
| 8 | 519 | 8 | 10 | 80.00 | Not specified | |
| 9 | 1607 | 11 | 12 | 91.67 | Leaf veins, roots | |
| 10 | 1163 | 2 | 12 | 16.67 | Stem pith, primary xylem | |
| 11 | 881 | 11 | 12 | 91.67 | Stem, trichomes | Primary xylem cells |
| 12 | 638 | 5 | 5 | 100.00 | Stem, leaf veins, root tip | |
| 13 | 900 | 8 | 12 | 66.67 | Primary xylem, cortex, pith, anthers, tip of style | |
| 14 | 603 | 10 | 10 | 100.00 | Stem, leaf veins | |
| 15 | 1631 | 7 | 12 | 58.33 | Roots, leaf veins, stem | Primary xylem, cambial cells, xylem ray cells |
| 16 | 786 | 12 | 12 | 100.00 | Parenchyma, pith | Parenchyma, pith, xylem |
| 17 | 898 | 5 | 10 | 50.00 | Phloem, leaf veins, cortex-parenchyma cells/phloem cells, and epidermal cells | |
| 18 | 563 | 2 | 7 | 28.57 | Primary xylem, parenchyma cells | |
| 19 | 524 | 2 | 12 | 16.67 | Late developing xylem, roots | |
| 20 | 638 | 5 | 12 | 41.67 | Inner pith, parenchyma cells, xylem | |
| 21 | 862 | | | | | |
| 22 | 691 | | | | Stem pith | |
| 23 | 970 | 7 | 12 | 58.33 | Vascular tissue | Cambial initials, early xylem |
| 24 | 447 | 11 | 12 | 91.67 | Stem, Vascular tissue, lateral roots | Differentiating Cambial initials, xylem, |
| 25 | 883 | 11 | 12 | 91.67 | Vascular tissue | Cambial initials, xylem, lateral roots, |
| 26 | 500 | 7 | 10 | 70.00 | Vascular tissue | |
| 27 | 650 | 8 | 10 | 80.00 | Vascular tissue | |
| 28 | 252 | 4 | 12 | 33.33 | Vascular tissue | Xylem, branch points |
| 29 | 322 | 8 | 12 | 66.67 | Vascular tissue | Pith, cortex, phloem |
| 30 | 204 | 2 | 12 | 16.67 | Vascular, stem material | |
| 31 | 784 | 6 | 8 | 75.00 | Vascular tissue | |
| 32 | 1161 | | | | Vascular tissue | Phloem, xylem, cambium |
| 33 | 500 | 2 | 7 | 28.29 | Vascular tissue | Xylem, parenchyma |
| 34 | 524 | 5 | 12 | 41.67 | Vascular tissue | Early, developing xylem, metaxylem |
| 35 | 1766 | 12 | 12 | 100.00 | Vascular tissue | Xylem, cambial cells, secondary xylem |
| 36 | 650 | 12 | 12 | 100.00 | Vascular tissue | Phloem, xylem |
| 37 | 894 | 9 | 9 | 100.00 | Vascular tissue | Primary xylem |
| 38 | 583 | 3 | 6 | 50.00 | Vascular Tissue | Primary xylem |

TABLE 3-continued

In planta GUS Vascular Expression

| SEQ ID NO | Size (bp) | No Plants GUS+ | No Plants Tested | % GUS Expression | GUS Vascular Localization | Microtome Results |
|---|---|---|---|---|---|---|
| 39 | 898 | 11 | 11 | 100.00 | Vascular Tissue | Xylem |
| 40 | 611 | 6 | 7 | 85.86 | Vascular Tissue | Inner pith cells |
| 41 | 537 | 7 | 10 | 70.00 | Vascular Tissue | Primary Xylem, phloem |
| 42 | 362 | 11 | 11 | 100.00 | Vascular Tissue | Xylem |
| 43 | 810 | 8 | 9 | 88.89 | Branch, base tissue | Xylem |
| 44 | 335 | 10 | 12 | 83.33 | Vascular | Xylem |
| 45 | 476 | 8 | 9 | 88.89 | Stem, vascular | |
| 46 | 536 | 8 | 11 | 72.73 | vascular | Xylem vessels, |
| 47 | 716 | 6 | 7 | 85.86 | vascular | Xylem, cambial, ray cells |
| 48 | 1643 | 11 | 12 | 91.67 | Vascular, stem material | xylem |
| 49 | 917 | 11 | 12 | 91.67 | Vascular, stem material | Primary xylem |
| 50 | 900 | 8 | 12 | 66.67 | Vascular material | Primary xylem, |
| 51 | 650 | 10 | 10 | 100.00 | Vascular material, stem section | Xylem, lignified xylem |
| 52 | 1650 | 12 | 12 | 100.00 | Vascular material | Xylem vessels |
| 53 | 1200 | 2 | 12 | 16.67 | Stem material, pith | Phloem, xylem |
| 54 | 674 | 5 | 5 | 100.00 | Stem, veins | |
| 55 | 822 | 12 | 12 | 100.00 | Parenchyma, stem | Xylem, cortex, thickened xylem cells |
| 56 | 1300 | 2 | 12 | 16.67 | Vascular material | |
| 57 | 674 | 5 | 12 | 41.67 | Vascular material | Xylem, pith, parenchyma cells |
| 58 | 1350 | 9 | 12 | 75.00 | Vascular material | Xylem rays, xylem |
| 59 | 700 | 2 | 7 | 28.57 | Stem sections | Xylem ring, cortex |

*N. benthamiana* tissue samples are placed in a vial containing fixative solution (100% Ethanol, Glacial acetic acid, 37% Formaldehyde, mQH$_2$0) and a vacuum is applied twice for 15 minutes. The samples are incubated in the fixative solution for two hours to ensure tissue infiltration. Following tissue infiltration, a vacuum is reapplied for 15 minutes and the tissues are placed at 4° C. overnight.

Following overnight incubation, the tissue samples are dehydrated through a series of ethanol incubations, wherein all incubations occur at room temperature. The overnight fixative solution is removed from the vial containing the tissue samples and replaced with 50% ethanol. After 30 minutes, the 50% ethanol is decanted and the tissues are incubated in a fresh aliquot of 50% ethanol. After 30 minutes in 50% ethanol, the solution is removed and replaced with 60% ethanol. Following 30 minute incubation, 60% ethanol is replaced with 70% ethanol. The 70% ethanol is decanted after 30 minutes and replenished with 85% ethanol. Following 30 minute incubation, the 85% ethanol is removed and the samples are incubated overnight in 95% ethanol.

Following tissue dehydration, the tissues are incubated at room temperature in a series of xylene solutions. The overnight 95% ethanol solution is removed, and the tissues are incubated in 100% ethanol for 30 minutes. After 30 minutes, 100% ethanol is removed and the tissues are suspended in 25% Xylene:75% Ethanol. Following 30 minute incubation, the solution is replaced with 50% Xylene:50% Ethanol. The solution is then decanted and replenished with 75% Xylene:25% Ethanol. After 30 minutes, the tissues are thrice incubated in 100% Xylene for 60 minutes. The tissues are then overnight incubated in a vial containing xylene and 20 paraplast chips.

To infuse the paraffin, the vials are placed in a 42° C. hybridization oven until the paraplast chips dissolve. Throughout the course of 8 hours, a total of 60-80 paraffin chips are added to the vial and allowed to dissolve. The samples are left overnight in a 62° C. hybridization oven. Over the course of the next two days, the paraplast is changed four times, at 12 hour intervals. To embed the tissues, the liquid paraffin is poured into the cassette and the tissues are placed in the proper orientation. The cassette is then placed at 4° C. overnight to allow the paraffin to harden.

As illustrated in Table 3, the disclosed isolated nucleotide sequences confer GUS reporter gene expression preferentially in vascular cambium, xylem, and/or phloem tissues. Of particular interest, SEQ ID NO 21 and SEQ ID NO 13 share substantial sequence homology, except SEQ ID NO 13 contains a 40-bp fragment insertion at its 5'-end (AAATATAA-CATAATCTAACTATTGATGTACATTATTCGCC). This 40-bp fragment (SEQ ID NO: 85) is present as an imperfect repeat in SEQ ID NO 13, yet is absent in SEQ ID NO 21. Interestingly, in the presence of the 40-bp fragment (e.g. SEQ ID NO 13), GUS expression is conferred, while in the absence of the fragment (e.g. SEQ ID NO 21), there is no GUS expression. This data is significant because it suggests that the disclosed 40-bp fragment (SEQ ID NO: 85) may constitute an element necessary and sufficient for vascular-preferred gene expression.

Example 8

Methods of Using a Vascular-Specific Promoter

Once a promoter having an appropriate tissue-specific and developmental pattern of expression is found, this promoter can be used to regulate a desired characteristic in a transgenic plant. In one embodiment, a xylem-specific promoter is used to regulate the composition and content of lignin in a plant. In this example, a xylem-specific promoter of the invention is operably linked to a gene encoding an RNA interference (RNAi) molecule corresponding to a portion of the coding region of cinnamyl alcohol dehydrogenase (CAD). CAD catalyzes the last step of lignin monomer synthesis and has provided a target for successful antisense-mediated down-regulation of lignin in transgenic plants using other promoters. See Yahiaoui et al., *Phytochemistry* 49: 295-306 (1998) and references cited therein. Expression of an RNAi molecule corresponding to a portion of CAD results in a decrease in the enzyme activity and a corresponding increase in the proportion of cinnamyl aldehydes in the lignin of the transgenic plants. CAD activity in transgenic plants is assayed by the method of Wyrambik et al., *Eur. J. Biochem.* 59: 9-15 (1975) as adapted by Baucher et al., *Plant Physiol.* 112: 1479-90 (1996). Lignin content and composition are measured as set forth by Baucher (1996). Down-regulation of CAD results in a color change in the wood and an increase in the proportion of more easily extracted cinnamyl aldehydes, which is commercially important for plants used in the pulp industry. Id. For example, poplars with decreased CAD activity display red coloration, and the lignin is more easily extractable, which improves the properties of the poplar trees for application in the paper industry. See Baucher et al. (1996).

In another example, Eucalyptus and pine are transformed. Eucalyptus and pine provide useful model systems for studying the effect of gene regulation on lignin content and composition because of its the high lignin content. Additionally, Eucalyptus and Pine exemplify plants in which the modulation of lignin content or composition can provide useful properties with respect to the paper or lumber industries.

To construct these transgenic plants, a fragment of CAD cDNA is operably linked in proper orientation to a xylem-specific promoter of the invention and a nopaline synthase 3' terminator. The CAD cDNA can be prepared, for example, by reversing the orientation of the gene sequence with respect to its promoter. Transcription of the CAD cDNA in the plant cell will generate an intracellular RNA transcript that is "antisense" with respect to the CAD gene. The entire construct is inserted as a restriction fragment into the binary vector pBI101.1 (Clontech, Palo Alto, Calif.). Vectors are electroporated into *A. tumefaciens* strain LBA4404 or C58pMP90, for eucalyptus or pine transformations, respectively. See generally, No et al., *Plant Science* 160: 77-86 (2000). Kanamycin resistant transformants are tested for CAD activity, transgene copy number is determined by Southern analysis, and mRNA expression of CAD is determined as described in Yahiaoui (1998). Suitable transformants then are rooted and transferred to a greenhouse.

Example 9

In Silico Expression

In silico gene expression can be used to determine the membership of the consensi EST libraries. For each library, a consensus is determined from the number of ESTs in any tissue class divided by the total number of ESTs in a class multiplied by 1000. These values provide a normalized value that is not biased by the extent of sequencing from a library. Several libraries were sampled for a consensus value, including Cambium, Xylem, Phloem, Vegetative Bud, Root, Reproductive tissues, Leaf, Stem, and Fruit libraries. As shown below in Tables 4-5, a number of the inventive promoter sequences exhibit vascular-preferred expression and thus are likely to be involved in wood-related developmental processes.

TABLE 4

*Eucalyptus grandis* Expression Profile

| SEQ ID NO | Bud (Veg) | Cambium | Fruit | Leaf | Phloem | Reproductive | Root | Stem | Xylem |
|---|---|---|---|---|---|---|---|---|---|
| 24 | 0.42 | 1.99 | 0.08 | | | | | | 2.33 |
| 27 | | 0.35 | 0.54 | | 0.17 | | 0.12 | 0.95 | 7.71 |
| 31 | 0.59 | | | 0.17 | | | | | |
| 33 | 0.08 | 3.69 | 0.85 | 1.56 | 0.28 | | 0.08 | 0.95 | 15.68 |
| 36 | | | | 0.83 | | | | | |
| 37 | | 1.31 | 0.15 | | 0.17 | 4.01 | 0.32 | | 1.23 |
| 59 | | | | | | | | | |
| 60 | | 11.98 | 0.15 | 3.35 | 0.17 | | 0.08 | 0.95 | 47.12 |
| 61 | 0.25 | 4.69 | 0.15 | 0.51 | 0.83 | 6.69 | 0.08 | 0.24 | 3.78 |
| 62 | | | | 0.35 | | | 0.35 | | 0.47 |

TABLE 5

*Pinus radiata* Expression Profile

| SEQ ID NO | Bud (Veg) | Cambium | Fruit | Leaf | Phloem | Reproductive | Root | Stem | Xylem |
|---|---|---|---|---|---|---|---|---|---|
| 24 | 0.42 | 1.99 | 0.08 | | | | | | 2.33 |
| 27 | | 0.35 | 0.54 | | 0.17 | | 0.12 | 0.95 | 7.71 |
| 31 | 0.59 | | | 0.17 | | | | | |

TABLE 5-continued

*Pinus radiata* Expression Profile

| SEQ ID NO | Bud (Veg) | Cambium | Fruit | Leaf | Phloem | Reproductive | Root | Stem | Xylem |
|---|---|---|---|---|---|---|---|---|---|
| 33 | 0.08 | 3.69 | 0.85 | 1.56 | 0.28 | | 0.08 | 0.95 | 15.68 |
| 36 | | | | 0.83 | | | | | |
| 37 | | 1.31 | 0.15 | | 0.17 | 4.01 | 0.32 | | 1.23 |
| 59 | | | | | | | | | |
| 60 | | 11.98 | 0.15 | 3.35 | 0.17 | | 0.08 | 0.95 | 47.12 |
| 61 | 0.25 | 4.69 | 0.15 | 0.51 | 0.83 | 6.69 | 0.08 | 0.24 | 3.78 |
| 62 | | | | 0.35 | | | 0.35 | | 0.47 |

TABLE 6

| SEQ ID NO | Gene Homology | Sequence |
|---|---|---|
| 1 | *E. grandis* Glucosyl transferase | AAAACCACAAATGGCCGCGGGACGTCACAATTTTTTTTCCTTCTAGAAGCTCTATAGTCAAAGCTGATCTATAAATTTT TGGGAACCACAACCACCATGTCTCGCCACCTTCGCTCGAACCTTATCACCACCACCGCCCTTGAGCCCTCCTCCATCAAC TCTTCTTC |
| 2 | *E. grandis* Ted (2) | AAAACAATGTAGCTTCTCTGTGTTATGAAAACTAACAAAAGGGCACATCTATTTCTCCATGACCATTATATTCGGAGGAG CATGGTCAAACTTAAATCAAAATTTATTATCCATAACTTACAAATTTCCAATTTAGCTAAACTCAAATCCCAAAGTATAG CAATTCTGTTAAAATTTTATCATCCGATAGTATAGAGCAATATTTTATAATACTTACATTGCTCAGCTCAATTACAAATT CTATTTGTCCACAAATTCAAACATTTTAATGATGCATTCCACATAAAACCAATGGTTTGAGACACCTTTTCAAAAAAAG AAAAAAATACACTAGCATTGCTTAGACAAGTTAATCAATGAAAAATAACTTTATCTTGTTTTTAATTAAGGATGAAAAGG AGTTACAAACGCTTGTTTCAAGATAAATATTTTTCAAATCTTTAATATTACAAGAAATAAACGGACCTTCTTATCAACCA AAAAAATGTAACATAAAAGGAACTTACCAATTTGATTGGACTCATTTATTGATTTTTGGAAAAATGTCGCAAATTTTCGT TGAGTTTTAGCTCCATGTACAATTTAGTCATTGAACTTTTAATTTATTCAATATAATTCATGAACTTTCTATACATATTT AGTCCATATAAAAATTAAGGGACCAAATTGAGTATTCACCAAAATTTTAGGGAAAATATTGAATAAATAAAAAGTTCTTG GACCAAATTTCTATATTGAAATAAAATTCATGGACAAATCATTATTCCTTGATTAAACTTTTTTATGTAGACACCCGTAAA TACAACCTGCCAAGGTTTGTTTGCAAGGCGTTTGCAAGGCGTTTGCACTTAAGCGGGACGGAGGCGTCACCAGTCAATGG GCATGTCCAGTGGCTTCCCCGGCTTGCGAATAGGATGCTTCCTGAATCATCTCC |
| 3 | *E. grandis* Cyclin B | AAAGTTTCTCTGTAGAGAGAGGGAGGGAGATATATCTGCGGTTTGCGTCTCTATTTCGCTTGTGCAGTTTTACTACTCCC CAAACACACACACACTCTCTCTGTTTCTCTCCTTTTTCCCCAAATCAGAAGAAGAAACGACAGTGTAGTAGTGCAGTTTC ACTACACCGTCTATACTAAGGGTAATCGTTTTTTTGAAAGCACATGCATATAGCCGTTGGAAAGGGGAGGGCACCGAGAT CGAATCGGATGGCTGATCCTCACTAGCCGTTAGAGAGAGAGAGAGAGGGAGGGATAATCATGTGCGGACATATATCCG CAATTTGCGTCTCTATTTCGCTTGTGCAGTTTCACTACTCCCCACACACACTCTCTCTCTCTCTCCTTTTCCCCCA AATCAGAA |
| 4 | *E. grandis* Cyclin B | CCTTGTATTTCCCCAACATTAAATGAAAGCCTACATCCAAAAACGTGGACCCGGCATTAAAGAAAAACCCCATCATCTCA TCCCATCCTTTATTTCAACCCTAAAGTGAAATTAAGATATAAGACGAAACCACCCCCAACCCCCAAAAAAAAAATATTA AGGGAATTCGTTTTTTTGAAAGCACATGCGGAGGTAGCTGTTGGAAAGGGGCCTCTACGTTCGGAAGGAATGCGACCATT CCATCGAGATCAAATCGAACTACTGATGCTCACTAGCTGTTGCGTTTAAACCTTCTTTGTAAAGCGATAAGGGAATTCGT TATTTTGAAAGCACATGCGGAGGTAGCCATTGGAAAGGGGCCTCTACGTTCGGAAGGAACACGACCGTTCCACCGAGATC GAATCGGACCGTTGATGCTCACTAGCCATTGTGTTTAAAGTTTCTCTGTAGAGAGGGGAGGGAGATATATCTGCGGTTT GCGTCTCTATTTCGCTTGTGCAGTTTTACTACTCCCCAAACACACACACACACTCTCTCTGTTTCTCTCCTTTTCCCCCAA ATCAGAAGAAGAAACGACAGTGTAGTAGTGCAGTTTCACCACACCGTCTATACTAAGGGTAATCGTTTTTTTGAAAGCAC ATGCATATAGCCGTTGGAAAGGGGAGGGCACCGAGATCGAATCGGACGGCTGATCCTCACTAGCCGTTAGAGAGAGAG AGAGAGGGAGGGATAATCATGTGCGGACATATATCCGCAATTTGCGTCTCTATTTCGCTTGTGCAGTTTCACTACTCCCC ACACACACTCTCTCTCTCTCTCTCCTTTTCCCCCAAATCAGAA |
| 5 | *E. grandis* Microtubule- Associated Protein | AAATTATGCAATTTCTTAATCAGGCCTAGCTAGAAACAAGGGCAAGGAAAGCCCCCGACGGGCTCTTATCTGCTGACGTG GCACGCCGTGGGTGGGCCCCCCGGGTCTTCCTTCGACGAAACCTCATCGTAGACAATCAAATCCTCCTCTCGATCATTA TTGCAAAGCCAACACCCAGCATTGAATCGATCCCCACCTTCTCCTCCTCCTCCTCTTGATCCTTTTTGTCCCGATGATGA TGGGTATCTGATCAGCCGATTCAATCCCATCGTCTCCTTCCTTCTC |
| 6 | *E. grandis* CAP adenyl cyclase | GTGCGGACACGTGTCCCCTTATCCCGCCCAAGACCGCGCAAAACCTGAAAATCCTCACTATTCCCTCACTTTCGGCGAAT TCGAAACAGCGCATAAAGGAACACGGAAAGAACATTCTCTACCCCAAGACGACGACGACGACGACGACGACGCCGCG CCTTATATAAACCATCGCCACTCCTGGCCATTCCCTTCTTTCTCCCCAGATCCAAT |
| 7 | *E. grandis* Ferulate-5- Hydroxylase | AAAGATAAAAATAGTGTGGAAAATAGATTTGAGAAGTGTTCATATATTTCGATTTATCATAGCAAAGATTTTATCGACCT ATTTTAGGCTTTATAGTGTGACTATTTAAGATAACGAATATTAATCGAGAGATGCACAATTAATAAGAGATATTCTCACG ATCTTGAGATATATAGAAACCGACAGAAAATATATTGATTATCTCTAATATAGAATAATATTCTAGAGAAGTATTGTAAT TGTGACCACCAACTAAAATGGGGCAGACAAAGTAGAGGGCCAGGTATAGTCAAGGCCAGTGAAAAGGAAATGAAATGAA ATAAAAGAAAAGAAAAGAAAAATCAAATCCTCCAACTTGTGTACAGGATACACCCGAAGCTTTGTGTATATAAAGGCCAC TTAATATCCTCCAACCTAGCAACACATTCGAAAGATAAGTTGCGCTTAAATCCTCTCCAAAAGAGCTAATC |
| 8 | *E. grandis* Cellulose Synthase | CTGCTGAAATTCTCGAGGAAGTTGAGAGGTTCCAGATTAGATCTTTACCAAACAAAAAAAAACTATTGCTTATGCTAAAT TGGTCATTATAATAAGATTTTTAGAATACTCGTTGAGTATACTCAACTCAAGATATTATAAGTTTTCTCAATTGGTTTT CTCCATTTCTTATGATCCGTCCACGAGCTTGGAGTCGCTTTTGAAGATGTAGCCAGCCCAACAGAACCGTTTCCTTCAT CTTCCCGCGAAAGTTTCATGTCATCTCCCTCCTCTGCATCACGAACCAAACCTCTGCTCTCTCTCTCTCTCTCTCTGC |

TABLE 6-continued

| SEQ ID NO | Gene Homology | Sequence |
|---|---|---|
| | | TTCAACACAATGACACCAACATCGCACCCTCCTCACCTTCCCAACCACCGCCATACCATCTCCTTTAAGCATTCCGATGA GTCCCTGATCCACCGCCTTCTCACTGAGCCTTCCCGCTCTCCCTCTTCTCGTCTCACTTTCTCATATAAAGAAGTGAAAG AATACGAGGATACTCCACTTGGGTATCGCCAAGAACTCAT |
| 9 | P. radiata LIM Promoter | CCTTTGGGAATGAACTTTGAGACCACCTCCAACCCGGATTCTGAAATCCATCCAGCAATTCCAAAGTTCCAAACCGAAAT AAACATCCCACCATACCATGGCATTCGGAAAAAAGCTAGGCTAAGCTGAAAATCACTGTCATAACCCAGTAAGACCATGC CACTAATAGCAAGAGAACCATACACCAACATGCAAAGCCATGCATGTCCAAACCAGCTAGGAAATCACACATGCAAGGG TTACCTGCAAGTATTCCTGTTGAAGTTGCTTGATCCTACTTTCTTTTCCTTGAGCCTTGCTTGCCTTCCTTTCCTTTGCT TGATTTTCCTTTCCTTGCTCCAAACTAGAGTGCTCTAAGAAAACTCTAAGTGACCAAGAGAGTGAGAGAGAGAGAGAATA ATGAGAGTCCAAACATGAACTTGACAAAAGCCATGAACTGATCCTCAGAAGTCATTTTATGCACGAGGCTTCTATTTTCT TCATTTTCCATCATTTTCCTTCAATTTCCTCATCACATGCAACGTGCGACTTTTCACCCCGTTTTCCTCCTAATTTCTTT TATTTTCATAAATAAATGTGCCAAAAATGCCTcTTGCCTTAGCCTTTGCCAGTTTCCTTAGCCAAAACACACATCCAATG ATGCCCACTAGGATATCTTTGCCCAACATTAAGCCTGGAATAAATGTCTCTTAATCGTGGTCTTATTTTGCTTTTATTAA CTTTTATTACATGAACTTTTCACTAAAGCTATTACAAAGATATATTTATTATGGCAATTATGTTTGATTTTTGAAGAGC TAGTAACTTTTAGTTTATTATGGCCTTTTCCGTAAACTTATTTTCTTGAAAATCTCTATAAATCCAATGAAAAATTTATA GAATATATGTTGTTGTTTCTTCACTACCTCTAATAAATTTTTACTTAGTAATCTACAAAGCCATTTATTAAAAAATTCA AGTTAATTAAAAATTAATATCATTTCAAAAGTCTTTTTAATATAGTCAAAGTTTATTAAATTCTATGATGTATATTTCT TTTAAATAAATGAAGAATCCATTTTTTTACTTAAAACCATATATTTTTTATAACGTTGATAAATAGCATGCATTTATATA AACAAATATATATTTTTATAACGTTAAGAGATTGTTAAAACTTTTAAATAATTAATATTTTATTTATTGTTTTGAAAAT GTCATGATTTCCACCTACCTCGCCCATCAAATCTTGCTGCAAACCAGGCTTACCCAACCCCACACCCACAATATATTTTT GGGATCTGGTGCCCCCACCTTTGATCACAGTGAACACCATAAAGACAAATTATAAAGGCAAGGGGACTTGGCACCCATGA GGCAACCGAAAGCAACAAATCATTTTTTTCCAAAGAGATGAGTGTATGCCAACGAAGAAACACGATGAACCCACGTGTCA TTGGCCAACTCCCACTTTCGACAAAAAGAAGGAAATTAGAATTAAAAAGGCGAATAAAAATTGAAAGGCCATTTAAAATA GAAGGAAGAATAGCCTATATGGTAGATTTAAATGCTTTTTTGAAATCCGGTTACTCGCAAGATTATCAATCGGGACTGTA GCCGAAGCTT |
| 10 | P. radiata Pectate Lyase | AAACAGAGCAGATAACACTAAAAAGACCAACCCTGTTAGGAGGGGAGAAACAAAAAAGATCACACTAAAAAGACCAACCC TCTTATCTAAACTTATTTTCTCTTATCTCTACCCCTTCTATTTTGAACCTTTATCATTTTGATAGAAAATATATGTTAAT AACCATTAAACCTACATTGTCAAGCTAGTGTAACTTATATGTTAATAACCATTAAACCTACATTGTCAAGTTAGTGTAAC TCCTTTGGTGGGGGTGGTTGTGTCTTCCTCTTCAATCTCATGCTATGACACACTTGTTTTTTAATAACATAGGCCGACAAGT TTGAGCCATTATCTATCTTGATTCCTCGAAATGATAAATAGATGTTGTCAGTGGACTTGAAAAAAACCAAGTAGGGAACA CCACGTAATCTTTCCAATGGCATTAAAAGCTACTTTGAAATATGTAACACTTAGCAATCCTTCCAAGGCATTAAACCTAC TCTAACCTATGGAACACTTAGCATCCTTCCCACGGTTGATAATAAATGATTGATTCCTCAGAATAACAAATAAAAAAAAA CTATAAAACTTACTCTAAAATATAAAATGAGTATGGAACACGTGGCAATCCTTCCCATGCTCGGCGGTAGCTACTCTCTC CAGAGATTTGAATAACACAGGCGCCGCAATTATGAGAGAGCAGTGGAGTTAAGACTTAGTAGCCATGGTTATTTTGAACG CGTGGCAATTCTTCCAAAGGTTGGTAGTTACTCTATCCAGAGATTTGAATAACACAAATGCTGCAGTTATGAGAGAGTAG TAGAGTTAAGTCTTGTCAGCAATGATAGTTACGAACAACCGTAATTTCTGGCTATCTCTGTGTTTATTGGTCGTTTACTT GCTACAGTGCTCTCACCCCACATGGTAACAGTGTTCGATGGCCATGATTTCTCCCCACCCCGCCAAACCTCTACGTTTTT ATTCTTTTAATAACTCCTAATTTAATATATAAGAGGGGGCAAGGTGTTCATACAGATTCGTGCAAACGACCTGAGTTCAG CACAAGTTTAGTCATTCCATGCGAACTCGACTGGCTCACGAGATCCCTCGCTGCAGTTATAGATTGCAGGAATTAGCTTA GCAGCATTTCTATCTATGATCTTCTGCCACTTCTTCCCCTCTC |
| 11 | P. radiata Expansin | AAATTAGTCAAATCCAAAGCAGACAACTTGGGCTCTCACCTAAATTAACACATATACCCTACCAGCTTCCATAGTTTCCA ACTTCCTTTCAATAAATCTATTCAAAAGCATGAAAAGCATGACTAAGGTTCAATTCCCAAGTTATGGACACCCACCTGCT CTAGGCATATAGGAAATCACAATCCAACTAACGACCAACTACCCAAAACTTTGAAGAAAATGAGTAAAGACTCCCCCAGT GATATTATAATTATATGGTCTCTCTAGAACCCTTTATTGCCCCTTCCAGTGTTATATTTAGTTCCCCATTTATATATCCC TTGACTTATGAAACCATTTAGGTGCATTAACATAGTCCTTGACTAACAAAAAAATTATTTAGGTGCAGTAGATACGGAAA GTAACCAATGATGCTAAGAAACTGTGCACGTACTTTAATGGAGGTATTACTTTTATTATGGTTGGTTTGGATACATTCAT AATGGAAGCATGTGCTCTTCATCGTTAAAGTTGTGGTGGGGCATTCCCATTTTCCACGAGAAACCGAATCCCGGCGTGG AGACGACGACGAAATCGATGGATATTCGGTGGAAAATTCACAGTAAAATTCCTGGAGAAAAGGTTGCCGAGGTAGTTGA AATCCAAACCGCCGAAATGAGCTGGAAACCCGCCTTCTGTCAGTTAGTTGAGTCATGACTGCAGCTGTCTCAGGTCTTAC ACTGTAAAGGCACCTTAATGAGGCATTCATTCTGGCAGTCTGGCTACGGAACTTAATAGTACTTGTTATTCCTGCCCCAA TATCTATTTAATAGGCATCCCCCCTCACTACTTCTTGCCCACAATCCCTCCATAGTCCTGAGCTTGAGACCATTTTTCTG C |
| 12 | P. radiata ACC oxidase | AAGGTTTGCTTGGACCAGCGACACAGGGAAAAACATGGCATGCGGGTTTGGATTAAGATGAGGCCCAATCTTAATTTGA TATGTTTGCCAAACCTTAGGTTGTTTATCTAATTTTTGATTGGATCTGATCTCTTGATGATTTAAGGGTTTTCCATGTTG ACACGCAATTGTAGGTTCCTGGGCACTAAGGTCTACCATGTGGCGAATTTATCGAGAGTTGACAATTCTGGTACTGTTAG TGATTTGTCACCACTCTACGGTCCCTGCAGATCTCAGATTTTTAATGGCTGCCTTTGATTATCTAAAGGCTAGCCCCTAA TCGCGGCTATGAATGTATAAAGAATGTGTTCCAATGCATTAGAGTACTCAAAGACATGTTGAAGGAAAAGGACAAGTCA AGGGACATGAGTAATAACCAAAAAGCACTTGGTCCTGACCATCTGTGTCTGATTCACACTGGGATTCACATGTTATTTA AGAAAAGTTGCATCAGTGCTGCAATCATCAAGCCATTCCTAATTTACCACCATGATTAGATTATTTAATGCAAGAAAC GCCTATATAAGGAGAGCTGCAGGCCCCAAGGTAATGCAGTAATCAAACTTGAGGAGAGATTTGAGAGTGTTTGTGAAGGG |
| 13 | P. radiata 4CL3 | AAATATAACATAATCTAACTATTGATGTACATTATTCGCCTATAACAAAATCTAAGTATTGATGTCACATTATTGGCATA TAACAAAATCTTTAGGATAACCCCTTAGTCAAGCTCTTGTACTTTCATGTTATTAACCAATAAATCAAGCTGATATGGA ATAGCAGACGTACGTGGTATAATAAATGGAGTGTAAGAGTTCGAACATTTTAATTCGGAGGGCAGCTTATGTGGAATA TCAGGCAATCATACAAGCTTGCTTTTGGGTAATAAAGACCCACATGTGGTAATAACAAGTGGATTTTAACAAACCAACAT TTTGATAGGGAGGATAGGTGGCCTGGTAAGTTAGAATGTGCTAGTCATGCCTTTGAAAGAAGTTAGTTGTGGAAGTCAAA CATGTTCCCCACACAACACCTCACCACACAAAATGCTGGTAGGTCATGTGATTGATGGATGGGCATGTGTATCCTCCA AAAAAAATGAATATACACACTAAATATTCTATTGACATAATATACAAAGAAGATTAGGTCTATGGAAGAAGGGAAGGCGA AGGGGAAGATTGGGTCGTGGGAAGATTGGGTCGTGTCCTGCTAGCACGTTGAATACCTACACGCCATTTCACATCTACC CATCAACGTCAAATAGAGCATCCAAATCAGGGCGTGGTGGTGTGAGGGGAGAGTGAGGAGAAGAAGTTGAAAAATTCTGG |

TABLE 6-continued

| SEQ ID NO | Gene Homology | Sequence |
|---|---|---|
| | | CTGAAAATCCACCTAACACACGCTCACCAGCCCCTCAACGAGGGGCACCAATTATGAATAATAATAGCTAGAACAGAGCA GCAGAAGCAGAGTTTATATCTATCCATTGTCGTCTGTAAATTACTCTGTGAGTGTTTAGTGTTTTCTTCTCTTATTGATT TCAGGGGACAAGTAGGTGGG |
| 14 | P. radiata 4CL1 or 4CL2 | AAACACCAATTTAATGGGATTTCAGATTTGTATCCCATGCTATTGACTAAGCCATTTTTCCTATTGTAATCTAACCAATT CCAATTTCCACCCTGGTGTGAACTGACTGACAAATGCGGCCCGAAAACAGCGAATGAAATGTCTGGGTGATCGGTCAAAC AAGCGGTGGGCGAGAGAACGCGGGTGTTGGCCTAGCCGGGATGGGGGTAGGTAGACGGCGTATTACCGGCGAGTTGTCCG AATGGAGTTTTCGGGGTAGGTAGTAACGTAGACGTCAATGGAAAAAGTCATAATCTCCGTCAAAAATCCAACCGCTCCTT CACATCGCAGAGTTGGTGGCCACGGGACCCTCCACCCACTCACTCAATCGATCGCCTGCCGTGGTTGCCCATTATTCAAC CATACGCCACTTGACTCTTCACCAACAATTCCAGGCCGGCTTTCGAGACAATGTACTGCACAGGAAATCCAATATAAAA GGCCGGCCTCCGCTTCCTTCTCAGTAGCCCCCAGCTCATTCAATTCTTCCCACTGCAGGCTACATTTGTCAGACACGTTT TCCGCCATTTTTCGCCTGTTTCTGCGGAGAATTTGATCAGGTT |
| 15 | P. radiata 4CL1 or 4CL2 | ATCTTATGGAGTTTTTAAATATATATATATTTTTGGGTTGAGTTTACTTAAAATTTGGAAAAGGTTGGTAAGAACTATA AATTGATTGAGTTGTGAATGAGTGTTTTATGGATTTTTTAAGATGTTAAATTTATATATGTAGTTGTGAAGGAGTGTTTT ATGGATTTTTTAAGATGTTAAATGTGTATATGTAATTAAAATTTTATTTTGAATAACAAAAAATTATAATTGGATAAAAA ATGTTTTGTTAAATTTAGAGTAAAAATTTTAAAATCTAAAATAATTAAACACTATTATTTTTAAAAAATTTGTTGGTAAA TTTTATCTTAAATTTAGTTAAAATTTAGAAAAAAAATAATTTTAAATTATTAAACTTTTGAAGTCAAATATTCCAAATG TTTTCCAAAATATTAAATTCATTTGACATTCAAAATACAATTTAAATAACAAAACTTCATGAAATAGATTAACCAATTTG TATGAAAACCAAAAATCTCAAATAAAATTTAAATTACAAAATATTATTAACATTATGATTTCAAGAAAGAGAATAACCAG TTTCCAATAAAATAAAACCTCATGGCTGGTAATTAAGATCTCATTAATTAATTCTTATTTTTTAATTTTTTACATAGAA AATATCTTTATATTATATACGAGAAATATAGAATGTTCTAGTCCAAGGACTATTAATTTCCAAATAAGTTTCAAAATCAT TACATTAAAACTCATCATGTCATTTGTGGATTGGAAATTAGACAAAGAGAATCCCAAATATTTCTCTCAATCTCCCAAA ATAAACCTAATTAATATAGTTCGAACTCCATATTTTTGGGAATTGAGAATTTTTCTACCCAATAATATATTTTTTTTATA CATTTTAGAGATTTTCCAGACATATTTGCTCTGGGATTTATTGGAATGAAGGTTTGAGTAATGAAGGTTTGAGTTATAAA CTTTCAGTAATCCAAGTATCTTCGGTTTTTGAAGATACTAAATCCATTATATAATAAAAACACATTTTAAACACCAATTT AATGGGATTTCAGATTTGTATCCCATGCTATTGGCTAAGCCATTTTTCTTATTGTAATCTAACCAATTCCAATTTCCGCC CTGGTGTGAACTGACTGACAAATGCGGCCCGAAAACAGCGAATGAAATGTCTGGGTGATCGGTCAAACAAGCGGTGGGCG AGAGAACGCGGGTGTTGGCCTAGCCGGGATGGGGGTAGGTAGACGGCGTATTACCGGCGAGTTGTCCGAATGGAGTTTTC GGGGTAGGTAGTAACGTAGACGTCAATGGAAAAAGTCATAATCTCCGTCAAAAATCCAACCGCTCCTTCACATCGCAGAG TTGGTGGCCACGGGACCCTCCACCCACTCACTCAATCGATCGCCTGCCGTGGTTGCCCATTATTCAACCATACGCCACTT GACTCTTCACCAACAATTCCAGGCCGGCTTTCGAGACAATGTACTGCACAGGAAATCCAATATAAAAGGCCGGCCTCCG CTTCCTTCTCAGTAGCCCCCAGCTCATTCAGTTCTTCCCACTGCAGGCTACATTTGTCAGACACGTTTTCCGCCATTTTT CGCCTGTTTCTGCGGAGAATTTGATCAGGTT |
| 16 | P. radiata Dirigent | AAACGCTTCATGCCCCAGAAGCCGCACTCGATGCTTTAGAATAAAATGGACCATTACCAGACTACGCGCCTCCAAAATAA CAAAACGTGTATTAGTTAAACCCTACATAGCACTTAAAGCTTGTCTTACTATTATTTTACGTAATTCTGTCTTTTTGAC AGTGGATTGATTGGAACTTCCATTCTCGATACAGTTGTATGCGTTATGTGAACTGAACCAACCTCGGCCAAAATATGGGG AAGATTCACTTCAGAAAAGACAGGACAACCATCTCTGATTGTCGACATTAATATCGGAAAAAATTCAGTCAAATGATGTG GAAAGGTTCATCTACGGAAAATAAAATAGCTCTGAGATGACCCGTTACATTTAGTGCATAGCATCTTTGTCAACAAGAAG AAATTTCCAGTTGTAGGACTGGTCATCAATGGCCGTGCCTGCAACGCTTTTTCGCAACAGGAAACACGGACTAAAAAACG CGGTCTATCTGTCATTTGACGGTACGTTTGGCACTGAGCCCGAAAAAATCCCATTGGTAGAATTTAGAAGAGGGAGCTTT CACTCGAAAATTCTGTACCACAAGCGGTGGCCTCACAATAACAAATTATTATACCCACATGGAAAATGTTAAATCGGACG GTCCGACGGTCGACCAAAGACAAAATTGATGAGAAAGTTTTGAGGGTGGGTGATAAAGTAAGCGCGTCTTTTCACAGGCA TCTGCATTATAAACCTGCAACTCCAACTTTCATCACAACAAATTTCATTTTCCCCTTCTCTGAGGC |
| 17 | E. grandis Laccase | AAAAAATTTATAACTAATATTGGTACAATTAGAAATTCTCTTGCCTTCCTTAATCTTGCTGTTAACTCCTCCATTTTAGG CGTAGACAACTATTTTTTTTCCACAAAAATGAAACAGTTCCTAAATAGACTAACGCCTTTTAAGCTGGTAGTAGACAGAC CGACACAAAATCCTGAACAGGCATGTACCGACACAAAGAGATTCATTTCACGAGTAAATTTGAATTTCGACAACTAATTC TACACATCGGTAATCACGCAAATATATCAGATCGGCAAAAAGTTATATTTTAGACAGTGACGTGACATCTCAAGCACCCA ATCCCTCTCAACAGGTGAAGAGCCATATTTTCATTACATAAAGGCATTTTTTTTTTTAATTTTTAATAGGTGGTCCGAC CGACAAGATATTATTATTTTCTATTTGCATGAAGAAGAAAAAGATTGGTTTTGACCACAATGGTTTGTCCTCTCGTTAC CCATTTTATATTTGGCAAGTTTGGTGATTGATTGTAGAAGAAACACGAAACACACGAGCAAAGTAAAGGACTCCAAACC CAAATTTTAATCCACAAACGAATTTACCCACATAAAAAAAGGGGAGATTATGATTAAATTCGTTGAATAATGCGACCCTT TAGGAGAAGGCTTATTAAGCAAGCATCGACGGAAGCTACACACTCCTTTTGGGGAGAGGCTAGTGGGTGCAACAACTACG ATTCGGGTAGAGCTAAGCTTTGTCCCCAGTGGCGGTACTGCCATGACCAGGGCTCTAAATCAAAACCTAATCTGCCAACC TCAAAACAAACGCTGTCTCGCCCCCCCCGGCTGCGCTATATAATGCAGCCGATGGCGTCCTTCCTTTCTCGAACCCTAAG CAGATCAAGAGTTTGAGT |
| 18 | E. grandis Laccase | GTGAAGAGCCATATTTTCATTACATAAAGGCATTTTTTTTTAATTTTTAATAGGTGGTCCGACCGACAAGATATTATT ATTTTTCTATTTGCATGAAGAAGAAAAAGATTGGTTTTGACCACAATGGTTTGTCCTCTCGTTACCCATTTTATATTTGG CAAGTTTGGTGATTGATTGTAGAAGAAACACGAAACACACGAGCAAAGTAAAGGACTCCAAACCCAAATTTTAATCCAC AAATGAATTTACCCACATAAAAAAAGGGGAGATTATGATTAAATTCGTTGAATAATGCGACCCTTTAGGAAAGGCTTAT TAAGCAAGCATCGACGGAAGCTACACACTCCTTTTGGGGAGAGGCTAGTGGGTGCAACAACTACGATTCGGGTAGAGCTA AGCTTTGTCCCCAGTGGCGGTACTGCCATGACCAGGGCTCTAAATCAAAACCTAATCTGCCAACCTCAAAACAAACGCTG TCTCGCCCCCCCCGGCTGCGCTATATAATGCAGCCGATGGCGTCCTTCCTTTCTCGAACCCTAAGCAGATCAAGAGTTTG AGT |
| 19 | E. grandis Unknown Protein | AAATTTTTTTTTTTTTGGGTGGGTAGTAGGATCTGTCAGAGTAAAGTGACTTAACGCCAATTCTCGACATTTCAGACT AATAAAATATTTACAGATGCAACGTCTCACTCTCTCCTTGCAAAACCAGAAAGGGACAGCAAGCAAGAAGAGGGGGAAGA GAAGCTTGCGTTTAAGCAAGGGGAGTGCTGACTTTTCAAGCGACTTAATTAATCTGTTTAGCACCCACTTTGGTTCGT TTGATCTTCTCGTGATTTATTATTTACCTATGTACAGCTGCGGTTGAAATGGCCTCTCGCTTAAATGGTAGTTTGTCC TTTTCTTGGGGTGGTTGCTTTGGAAATATTCTTTTAGAAGCAGGGGCAAAGAAATGGAGTGGCATCTGATGCTTCTTCA ACACTTTGCAGCCATATCGAGAATATATACCTAGAGAGAGAGAGAGAGAGAGAGAGAGAGGAGCAGTGGAGAAGAAGG AGAAGAAGAAAAGGGTCAGATCAGATCCAGTTGTTGGGAGCAAGT |

TABLE 6-continued

| SEQ ID NO | Gene Homology | Sequence |
|---|---|---|
| 20 | *P. radiata* Cellulose-synthase like | CTGTATTCATCACTTTACACCCATGATTCCAAACCCTACACATTTACACTGATAACCAAGGGTTCAGGTTCTTTCCAATT<br>CATTTTAATCCAGGATGATAATAAATTTGAATAGCACAATAGCATATTCCAACTGaCATATCCCTACATTTGGGATCTCT<br>TTCCACGTTATAAATGGCTTCAATTTAGGGATCCCTTTCCACATTATATAACTGGGTTCACAGTGGTTTGAAGATAGCTG<br>TGGTTTGAAGATAGCTGTATATGTTATCAAAATGACAGCTCCCTTGCCAGGGACCATCGCTTGAATGATGAGATCCCGCC<br>TGTAAGGCAACTTGCAGCATGATTATTTTACATCTGCTTGACCAATTATCTAACAATATACGCGGTGTCGTCGTTCGGTT<br>AAATAATAGTGAAACTTCCTCGTGTTGTCCCTGCAGTTACGTATGTCTTGTTCTTTTTTTGTTTAATAaCATACAGCAG<br>AGCAAGTGTTGGGTGAATAAATATTGGGAAGAAGCTGCAGCGTTCACGTTCATTCATTCACTCATCGTGAGCAGCAGTAC<br>ATCAACAGTTCTTGAAGAACATTGATAGGTTGGCTATTTCAATCCTTTCATGGGGAATATTTAAGTCTGGATCCGAGC |
| 21 | *P. radiata* 4CL3 | AAATATAACATAATCTAACTATTGATGTACATTATTCGCCTATAACAAAATCTTTAGGATAACCCCTTAGTCAAGCTCTT<br>GTACTTTCATGTTTATTAACCAATAAATCAAGCTGATATGGAATAGCAGACGTACGTGGTAATAATAAATGGAGTGTAAG<br>AGTTCGAACATTTTAATTCGGAGGGGCAGCTTATGTGGAATATCAGGCAATCATACAAGCTTGCTTTTGGGTAATAAAGA<br>CCCACATGTGGTAATAACAAGTGGATTTTAACAAACCAACATTTTGATAGGGAGGATAGGTGGCCTGGTAAGTTAGAATG<br>TGCTAGTCATGCCTTTGAAAGAAGTTAGTTGTGGAAGTCAAACATGTTCCCCACACAACACACCTCACCACACAAAATGC<br>TGGTAGGTCATGTGATTGATGGATGGGCATGTGTATCCTCCAAAAAAAATGAATATACACACTAAATATTCTATTGACAT<br>AATATACAAGGAAGATTAGGTCTATGGAAGAAGGGAAGGCGAAGGGGAAGATTGGGTCGTGGGGAAGATTGGGTCGTGTC<br>CTGCTAGCACGTTGAATACCTACACGCCATTTCACGTCTACCCATCAACGTCAAATAGAGCATCCAAATCAGGGCGTGGT<br>GGTGTGAGGGGAGAGTGAGGAGAAGAAGTTGAAAAATTCTGGCTGAAAATCCACCTAACACACGCTCACCAGCCCCTCAA<br>CGAGGGGCACCAATTATGAATAATAATAGCTAGAACAGAGCAGCAGAAGCAAAGTTTATATCTATCCATTGTCGTCTGT<br>AAATTACTCTGTGAGTGTTTAGTGTTTTCTTCTCTTATTGATTTCAGGGGACAAGTAGGTGGG |
| 22 | *E. grandis* Euc ATHB8 | AAACGGACAGGAACCAAACTGGATCGGATCCAATTCCTAGTCCTAAAACCAACCAATCCCCACTTTCTAATTTTTGGAAT<br>CGGTCCTATAGGTTCCATTTTGAAATCGATCGCCCTTATATGAATGAAAGAGCGCTCACATGTACCGTTAGATGGTATAG<br>ACCTAATAATCTGATGGCTCATTGCGTTTTGAGCTCACATGGGCGAGATTATTGTAATAATGACGTCAGGGA<br>GAGGAGAGGAGAAGAAGATGAAGAGAAAGCTGTGGAGAAACAAAACACAAGGCTCGTTGGAAGCAACGTAAACAACAGCAA<br>ACAACATCAACAACGGCGACAAAAGAAGAGAGAGAGAGAGAGAGAGAGAGAGGAAACAAAAACAAAAGCAAAGTTGGGG<br>AGTGAAGAGGGGAAAAGAAAGATGATGTGAAAACAAACCAAACTCTCCTTTTCTTCCACCTCTCATTTTCTGTCTGGTAT<br>ATGGGGGTCTCTCTCTCTCCCTCTCTCTCTCTACCTTCTCTCTCTACTTTCTCTTTCTTAGGGGGGGCGTC<br>CCCAGGGTCTCCGATCCCAATATCATTCCCCCCCACTCTTTTGCTGCCATATACATACAAAAAACCGAAGCTTGTGAACA<br>ACCCATCTCTCTCTCTCTCTCCCTCTCTCTTTCTGCCTGCGAAACTGTGTC |
| 23 | *E. grandis* Euc Ted 2 | AAAACAATGTAGCTTCTCTGTGTTATGAAAACTAACAAAAGGGCACATCTATTTCTCCATGACCATTATATTCGGAGGAG<br>CATGGTCAAACTTAAATCAAAATTTATTATCCATAACTTACAAATTTCCAATTTAGCTAAACTCAAATCCCAAAGTATAG<br>CAATTCTGTTAAAATTTTATCATCCGATAGTATAGAGCAATATTTTATAATACTTACATTGCTCAGCTCAATTACAAATT<br>CTATTTGTCCACAAATTCAAACATTTTAATGATGCATTCCACATAAAACCAATGGTTTGAGACACCTTTTCAAAAAAAAG<br>AAAAAAATACATAGCATTGCTTAGACAAGTTAATCAATGAAAAAATAACTTTATCTTGTTTTTAATTAAGGATGAAAAGG<br>AGTTACAAACGCTTGTTTCAAGATAAATATTTTTCAAATCTTTAATATTACAAGAAATAAACGGACCTTCTTATCAACCA<br>AAAAAAATGTAACATAAAAGGAACTTACCAATTTGATTGGACTCATTTATTGATTTTTGGAAAAATGTCGCAAATTTTCGT<br>TGAGTTTTAGCTCCATGTACAATTTAGTCATTGAACTTTTAATTTATTCAATATAATTCATGAACTTTCTATACATATTT<br>AGTCCATATAAAAATTAAGGGACCAAATTGAGTATTCACCAAAATTTTAGGGAAAATATTGAATAAATAAAAAGTTCTTG<br>GACCAAATTTCATATTGAAATAAAATTCATGGACAAATCATTATTCCTTGATTAAACTTTTTTATGTAGACACCGTAAA<br>TACAACCTGCCAAGGTTTGTTTGCAAGGCGTTTGCAAGGCGTTTGCACTTAAGCGGGACGGAGGCGTCACCAGTCAATGG<br>GCATGTCCAGTGGCTTCCCCGGCTTGCGAATAGGATGCTTCCTGAATCATCTCC |
| 24 | *E. grandis* Euc cyclin | AAAGTTTCTCTGTAGAGAGAGGGGAGGGAGATATATCTGCGTTTGCGTCTCTATTTCGCTTGTGCAGTTTTACTACTCCC<br>CAAACACACACACACTCTCTCTGTTTCTCCTTTTCCCCAAATCAGAAGAAGAAACGACAGTGTAGTAGTGCAGTTTC<br>ACTACACCGTCTATACTAAGGGTAATCGTTTTTTTGAAAGCACATGCATATAGCCGTTGGAAAGGGGAGGGCACCGAGAT<br>CGAATCGGATGGCTGATCCTCACTAGCCGTTAGAGAGAGAGAGAGAGGGAGGGATAATCATGTGCGGACATATATCCG<br>CAATTTGCGTCTCTATTTCGCTTGTGCAGTTTCACTACTCCCCACACACACTCTCTCTCTCTCTCTCCTTTTCCCCCA<br>AATCAGAA |
| 25 | *E. grandis* Euc cyclin | CCTTGTATTTCCCCAACATTAAATGAAAGCCTACATCCAAAAACGTGGACCCGGCATTAAAGAAAAACCCCATCATCTCA<br>TCCCATCCTTTATTTCAAACCCTAAAGTGAAATTAAGATATAAGACGAAACCACCCCCAACCCCCAAAAAAAAATATTA<br>AGGGAATTCGTTTTTTTGAAAGCACATGCGGAGGTAGCTGTTGGAAAGGGGCCTCTACGTTCGGAAGGAATGCGACCATT<br>CCATCGAGATCAAATCGAACTACTGATGCTCACTAGCTGTTGCGTTTAAACCTTCTTTGTAAAGCGATAAGGGAATTCGT<br>TATTTTGAAAGCACATGCGGAGGTAGCCATTGGAAAGGGGCCTCTACGTTCGGAAGGAACACGACCGTTCCACCGAGATC<br>GAATCGGACCGTTGATGCTCACTAGCCATTGTGTTTAAAGTTTCTCTGTAGAGAGAGGGGAGGGAGATATATCTGCGGTTT<br>GCGTCTCTATTTCGCTTGTGCAGTTTTACTACTCCCCAAACACACACACACTCTCTCTGTTTCTCCTTTTTCCCCCAA<br>ATCAGAAGAAGAAACGACAGTGTAGTAGTGCAGTTTCACCACACCGTCTATACTAAGGGTAATCGTTTTTTTGAAAGCAC<br>ATGCATATAGCCGTTGGAAAGGGGAGGGCACCGAGATCGAATCGGACGGCTGATCCTCACTAGCCGTTAGAGAGAGAG<br>AGAGAGGGAGGGATAATCATGTGCGGACATATATCCGCAATTTGCGTCTCTATTTCGCTTGTGCAGTTTCACTACTCCCC<br>ACACACACTCTCTCTCTCTCTCTCCTTTTCCCCCAAATCAGAA |
| 26 | *E. grandis* Euc F5H | AAAGATAAAAATAGTGTGGAAAATAGATTTGAGAAGTGTTCATATATTTCGATTTATCATAGCAAAGATTTTATCGACCT<br>ATTTTAGGCTTTATAGTGTGACTATTTAAGATAACGAATATTAATCGAGACGATGCACAATTAATAAGAGATATTCTCACG<br>ATCTTGAGATATATAGAAACCGACAGAAAATATATTGATTATCTCTAATATAGAATAATATTCTAGAGAAGTATTGTAAT<br>TGTGACCACCAACTAAAATGGGGCAGACAAAGTAGAGGGCAGGTATAGTCAAGGCAGTGAAAAGGAAATGAAATGAA<br>ATAAAAGAAAGAAAAGAAAATCAAATCCTCCAACTTGTGTACAGGATACACCCGAAGCTTTGTGTATATAAAGGCCAC<br>TTAATATCTCCTCCAACCTAGCAACACATTCGAAAGATAAGTTGCGCTTAAATCCTCTCCAAAAGAGCTAATC |
| 27 | *E. grandis* Euc cellulose synthase | CTGCTGAAATTCTCGAGGAAGTTGAGAGGTTCCAGATTAGATCTTTACCAAACAAAAAAAAACTATTGCTTATGCTAAAT<br>TGGTCATTATAATAAGATTTTTAGAATACTCGTTGAGTATACTCAACTCAAGATATTATAAGTTTTCTCAATTGGTTTTT<br>CTCCATTTCTTATGATCCGTCCACGAGCTTGGAGTCGCTTTTGAAGATGTAGCCAGCCCAACAGAACCGTTTCCTTCATC<br>TTCCCGCGAAAGTTTCATGTCATCTCCCTCCTCTGCATCACGAACCAAACCTCTGCTCTCTCTCTCTCTCTCTGCT |

TABLE 6-continued

| SEQ ID NO | Gene Homology | Sequence |
|---|---|---|
| | | TCAACACAATGACACCAACATCGCACCCTCCTCACCTTCCCAACCACCGCCATACCATCTCCTTTAAGCATTCCGATGAG<br>TCCCTGATCCACCGCCTTCTCACTGAGCCTTCCCGCTCTCCCTCTTCTCGTCTCACTTTCTCATATAAAGAAGTGAAAGA<br>ATACGAGGATACTCCACTTGGGTATCGCCAAGAACTCAT |
| 28 | E. grandis Euc CAP | GTGCGGACACGTGTCCCCTTATCCCGCCCAAGACCGCGCAAAACCTGAAAATCCTCACTATTCCCTCACTTTCGGCGAAT<br>TCGAAACAGCGCATAAAGGAACACGGAAAGAACATTCTCTACCCCAAGACGACGACGACGACGACGACGACGCCGCG<br>CCTTATATAAACCATCGCCACTCCTGGCCATTCCCTTCTTTCTCCCCAGATCCAAT |
| 29 | E. grandis Euc microtubule associated | AAATTATGCAATTTCTTAATCAGGCCTAGCTAGAAACAAGGGCAAGGAAAGCCCCCGACGGGCTCTTATCTGCTGACGTG<br>GCACGCCGTGGGTGGGCCCCCCGGGTCTTCCTTCGACGAAACCTCATCGTAGACAATCAAATCCTCCTCTCGATCATTA<br>TTGCAAAGCCAACACCCAGCATTGAATCGATCCCCACCTTCTCCTCCTCCTCCTCTTGATCCTTTTTGTCCCGATGATGA<br>TGGGTATCTGATCAGCCGATTCAATCCCATCGTCTCCTTCCTTCTC |
| 30 | E. grandis Euc glycosyl transferase | AAAACCACAAATGGCCGCGGGACGTCACAATTTTTTTTCCTTCTAGAAGCTCTATAGTCAAAGCTGATCTATAAATTTT<br>TGGGAACCACAACCACCATGTCTCGCCACCTTCGCTCGAACCTTATCACCACCACCGCCCTTGAGCCCTCCTCCATCAAC<br>TCTTCTTC |
| 31 | E. grandis SAD | CTGTCACCTCTGGCTGGTCGCCGAACCTCAGCGACCGACTGGAGGAAGAAGAGGAAAAGAAAAAAATAAAAATAAAATTC<br>TAAAATATTAAAATATTATTAAAAGTTGTCCACGTCAGCGTTGAGGCCACGTTAACTAGCCGGTGTCGAGTCAGCAAAAT<br>TCGGCCAAAATTGGCACAAAAAAAGGTTTAGGACTTTTTTGACGCTTTTCCCGTCATGAGCCTAAATAAGAAATTTTAAT<br>TTCTTCATACCATACCAATTATTTGATATGAGATTTTTCTAACTAATTCACACATCTATGCTAACGCTACTCGCTCAAAA<br>AGCGCTCAAGCTGAAGCCAAGTTTCAAGCATCAAGCTTATAAGCCGAGCCAAGCTCGAGCACGGTGCTTCTTTTCTCGGC<br>CTGACCCGATTAGACTCTTGACTGAACATGACATATGAAATTGCAGAGCATTCAATTTAAAAGATTGTGAAATTTCTGGG<br>CATTTATTTACCTCCCTGTTAATGATATTGCAGAGCATTCAATTTAAAGATTGTGAAATTTCTGGGCATTTATTTACCTC<br>CCTGTTAATGATATTTTATGGAATAGCGTGCAAAGAATTCGGGTGCATAGTGTTGTCCTTCTCCCAACGCCCCCTTATA<br>TAATCTCCGAACGGAGCAAGCATTTGCTCTTCCGTACCCACGGCATTTTCCTTCTCGTGACCTTTTCCCGAGAAAACAAG<br>AAGAAGAGAAAATCCTTCCATTGCATCG |
| 32 | E. grandis B-expansin | CTGACGCCTAACATGTACCTTAACTGTAATGTAGCAGCGCAGGTCGTCATAGCAGAGGCCGGTCATGCTGGTCAGGTAGT<br>TACTTTAAAAATCTGGAAAGCTTCTTTGTTGTTGTCTTTGCTGCTTTTCTTCGCTCTTTCGGCGAACTTCCCAGTCGATT<br>CATCGGTCTAAAGAATAGACACGGAGGTTATCGCAAACTTATGCAGAGATTCCTTGCGGTACGCAAATGCATGTTTAATA<br>GATCATTATGTTAAATAGATAATATAGTGACTTTCAGGATCCGTTTGTTTTGCAAATTTTTTTCCTAAAATTGGTAACA<br>TGCAACGCTTGAAATTATCAATTAGCGAAAAATATTATTATCATAGAGAACAATTTATATAAACCTTCTCCCAGCCTAAT<br>AAGCATGCCTGGTTCTCTAATATCAAAGAAAAAGAGGGAGCTAGATCTCGCCTTTAGAATGATTTGAAGTAATTGCAGTTA<br>GCTTGAAGACATTCGTAGATGTCGATTGATCAATGCTTTTGGAAGTACTAGAGATGCGCACGCATACGTGCGATATCCAA<br>ACTATTTCCGTTGACCCTCACGAAAATCTCCGTACAGACCGTTGTTGCTAATTCTTTATTTGCCGTAAAATCTGCATGAA<br>TCCATAAATTCAATGATTCGAACGTGACGCAGAGGAAGTTATGCATTGCAAAAGATAGCATTTATTTTAAATAAAGAAGT<br>GAAGATTACAATATCTTAGGTGCCTATTTATAGAGAGGTCGTCATCTAGAAAATAACCAAGTAACCGAAATTGAATAACA<br>AAATTAAAAATATATATTGATAAAAAGGGAAAGTTATCAAAATACAACTAGAAAATCTCCAAAATGTGTTTGAAATCTG<br>TGATATCTCGGATTTGTGGGATCGCTTGCTCTCATGACGCTCTAATGTTTCCATAAAGGCATTTGCGGAGATTATTGTGT<br>CGGATTATTCAGCTTGCAAGAAAAGTTATAGTGCAGAACAACATATAAAATAACAATAAATAATGGCAAAAACTATCGC<br>CGAAAATTCTCCAATGACGACAAGGACTCCGATTTAGTGGAATTTTGTGCTGTCAATTTGACTATAAATACCCGCCCGTT<br>GTGCTCCCAAATCGAGTGCAAGAAATGAAACTCCTGACCAA |
| 33 | E. grandis Putative Laccase | GTGAAGAGCCATATTTTCATTACATAAAGGCATTTTTTTTTTAATTTTTAATAGGTGGTCCGACCGACAAGATATTATT<br>ATTTTTCTATTTGCATGAAGAAGAAAAAGATTGGTTTTGACCACAATGGTTTGTCCTCTCGTTACCCATTTTATATTTGG<br>CAAGTTTGGTGATTGATTGTAGAAGAAACACGAAACACACGAGCAAAAGTAAAGGACTCCAAACCCAAATTTTAATCCAC<br>AAATGAATTTACCCACATAAAAAAAGGGGAGATTATGATTAAATTCGTTGAATAATGCGACCCTTTAGGAGAAGGCTTAT<br>TAAGCAAGCATCGACGGAAGCTACACACTCCTTTTGGGGAGAGGCTAGTGGGTGCAACAACTACGATTCGGGTAGAGCTA<br>AGCTTTGTCCCCAGTGGCGGTACTGCCATGACCAGGGCTCTAAATCAAAACCTAATCTGCCAACCTCAAAACAAACGCTG<br>TCTCGCCCCCCCCGGCTGCGCTATATAATGCAGCCGATGGCGTCCTTCCTTTCTCGAACCCTAAGCAGATCAAGAGTTTG<br>AGT |
| 34 | E. grandis Euc unkown protein | AAATTTTTTTTTTTTGGGTGGGTAGTAGGATCTGTCAGAGTAAAGTGACTTAACGCCAATTCTCGACATTTCAGACT<br>AATAAAATATTTACAGATGCAACGTCTCACTCTCTCCTTGCAAAACCAGAAAGGGACAGCAAGCAAGAAGAGGGGGAAGA<br>GAAGACTTGCGTTTTAAGCAAGGGGAGTGCTGACTTTTCAAGCGACTTAATTAATCTGTTTAGCACCCACTTTGGTTCGT<br>TTGATCTTCTCGTGATTTATTATTTACCTATGTACAGCTGCGGTTGAAATGGCCTCTCTCGCTTAAATGGTAGTTTGTCC<br>TTTTCTTGGGTGGTTGCTTTGGAAATATTCTTTTAGAAGCAGGGGCAAAGAAATGGAGTGGCATCTGATGCTTCTTCAA<br>CACTTTTGCAGCCATATCTGAGAATATATACCTAGAGAGAGAGAGAGAGAGAGAGAGAGAGAGGAGCAGTGGAGAAGAAGGA<br>GAAGAAGAAAAGGGTCAGATCAGATCCAGTTGTTGGGAGCAAGT |
| 35 | E. grandis Euc unkown protein | ATCATTAATATCATTAGAAAGATATATTACATTTTAAAGATGAATAAACATTTGAAATGTTTTCTCTACAACTAAAAAAA<br>AAATCATTGCCTCTACAACTAAAAAAAAGATCATTGCCCATTATGACATTTCATTTTTTTCTAATCACATCAAATTACT<br>TTAGAATAACTATCCAGCTGCCAAAAAAAAATAGTATTGTATATCTAAAATAAATATATTGACAAATGCCAACTAAATTA<br>GGTATCAACGAATACCTCTTACTTTCCTACAATCGAAGATGTAAAGACTAATGTACATTTCTTCATGATTATGTACTAAT<br>CGATTACAAAAACCAACATTTTTTTTAGTTCTTGAATTTCTTTTATTTAGGAACATGATACTCCACCAAATATGTTCTTTAG<br>CTAAAGAATGATATATATTATTTTTAAAATTGCGATTGGATTCTTCATATGTTATATCTTGTTCAAATATTATTATTTTG<br>ATTTGATTTTCAAAATAAAACAGAAAATAAATCTCATCTCGTTCCTTTTTCAATAGTGAAAATCCCACCAAATTCATT<br>GACAAAAATCATGAAAACAGTAAAGCTTGTATTTTCATTCCCAACTTTAAAACTGGTGGGTGACATTCCAAATGATCAT<br>ATGGTCATATACTAAATTTTCCCAATTTCTGAGCGTGCTCAACGTGATGTACCCTTTATTTTCGGATCATGCCAGGTCA<br>ATAGAGAAAATTTATCAAAGATTAGTTTAATGATGAATTGGGACCAACCTCTCAAGTCCTCATGAAACTGCCGTATGCGCAA<br>CCGTAAGCTCCGTTCCAATTTTTCTAATGATTCAAGGAAAAATAAATAAATAAAAAGTCCATCGTCGATGTGACATTTC<br>GCCTGCGCTCTCCAGCTACTTAATCAATCAATATATACGAATTATTTAGCACATGACAGCATTTTTCCCTTTTTCCTGGC<br>GTCCTCCTAGGGTGGATCCGGACCGTGGATCGAACTACAGGAGTGGCGGGCTCTCCGCCACCGACAGCAAAGTCAATAT<br>CAATCATCGATGGCAGTCGCTTTCCGGACGATTCATACTCATCCGAGTCCATTTCCCACTTCAACCTCAAGTCCCTCCTC |

TABLE 6-continued

| SEQ ID NO | Gene Homology | Sequence |
|---|---|---|
| | | GTCCACAAATGTAAAAATGAAAAAATGGAGGGCAGATTAGACTGAATTTTAGCTGTACAACACATGTTGCCTGTGCTTCA<br>CGTTCAAGATCCACGGTTGCTTTGCTGTTGCACTCGCACCAACTGTACTGAATCTCCCTTTATTTCTCTCTTTTAATTTT<br>TTTTTTTTTGGGTGGGTAGTAGGATCTGTCAGAGTAAAGTGACTTAACGCCAATTCTCGACATTTCAGACTAATAAATA<br>TTTACAGATGCAACGTCTCACTCTCTCCTTGCAAAACCAGAAAGGGACAGCAAGCAAGAAGAGGGGGAAGAGAAGACTTG<br>CGTTTTAAGCAAGGGGAGTGCTGACTTTTCAAGCGACTTAATTAATCTGTTTAGCACCCACTTTGCTTCGTTTGATCTTC<br>TCGTGATTTATTATTTACCTATGTACAGCTGCGGTTGAAATGGCCTCTCTCGCTTAAATGGTAGTTTGTCCTTTTCTTGG<br>GGTGGTTGCTTTGAAATATTCTTTTAGAAGCAGGGGCAAAGAAATGGAGTGGCGTCTGATGCTTCTTCAACACTTTGCA<br>GCCATATCGAGAATATATACCTAGAGAGAGAGAGAGAGAGAGAGAGAGAGAGGAGCAGTGGAGAAGAAGGAGAAGAAGAA<br>AAGGGTCAGATCAGATCCAGTTGTTGGGAGCAAGT |
| 36 | E. grandis Euc Csl-9314 | AAACTCATACTCTTGATAAGATGCAGACATTGCTGGCGTTCAACAAGGAAAAGAAAAAGAAGGAATAAGACAAAGTGAAA<br>GAGAAAAAGGAAAAAAAAGTAAAGTAAAATAAAATATCATTAAAAATTGTGTATGTTAGGGTTGTTAGGCATTTATGTC<br>CGCACCAATTGACGCATTTATGTCCGCACCAATCGAACCATTTATGTTCGCACCAATCGACGCATTTATGTCTGCACCAC<br>TCATCTGCACCAATTGGCCAAAATTGGCCAGAATGATTGAATTGACATAATTGCAAATATCTAAGACTGAACAAGCAAA<br>AAAAAAAGTTATGACCGAATTAGAAAAATTACAATAGATTTATGACTTTTTTTGTAATTCCCCCCACCTAACTCTGTCAA<br>ACCTGCTAATATAGACTAATTCATTCATATATTTATATATACACACTCATAGGTTGATATATGAATATGGGGGTACGTAT<br>AACCCTATGTGCTAAAATCTTGGAGAACTTCCTATTCATATCAGAAGAAGAACCGATCCTGT |
| 37 | E. grandis Euc CAD | AAAACAGATTGTTTTAGATTGATAACGTTTTCCTATCATGCCGGCATCATCTCAATTTTGAATTATATCGGAGCATTAAA<br>TATAAAAGTTAGGTTACGGATGATAATGCAGACCTAGTGAGAAATTAGTATAATCACGATAAAAATATCCATATA<br>GACATCACAAAAATGCCGCCCGATCTGATGAAATCCGACAAATAACACAAACATATATATGTCCAAGACTTGGACTTCAA<br>GTCGACATGCTTGTGCATGCACAATTTTGGGCCATAAAATTGGGCATGTGAGAACCTCAAACCGTTAAGAGATCAGGTAT<br>TTACTTTGTTTGTCGACTGACGAGACGTGCACGCATTTCACACCCTCTTCTCATTGATCTTCAAAGCTTTTCCGAACTCA<br>CGATGGTTCCAGAAAGGCGATGTTTTGCTGACAGAGGGAGCGTTCGATGGAGCTTCTCCATCACTTAATTTGTCCCTTCA<br>AGATGAAAAAAGTAAGAGGTCCACCGTACCAAAACATTCTTCCACCCAGAAGAAAAACCACAGTAGCTGGAGGGAGTCAAG<br>CATGTCAGAAGCACAGAAACTGGGAATGGCTAAAAAGCAAGTCTTGACCCTTAACCCACCCCACTGGTTCACCTACCGCA<br>CCTCGGGTTAGGTATTGCTTGCTGAGGTGTCACTTTTCGCCAAAGTCATGTCTCTCTTTTGGAATCTTCTTATTGGTCCG<br>TCTCGTTTCCTCGTTGCTGGATGCTGGTAGCGTTTTTGTCCATATATATATGCAGTCCATATGTATCCCCGTCACTCCTC<br>ATCTATGCTCCTACCCGGCAACTTCCCACTACGATAAGCAGCAAGTTTTCGGCTCTGT |
| 38 | E. grandis Euc CAD | ATCAGGTATTTACTTTGTTTGTCGACTGACGAGACGTGCACGCATTTCACACCCTCTTCTCATTGATCTTCAAAGCTTTT<br>CCGAACTCACGATGGTTCCAGAAAGGCGATGTTTTGCTGACAGAGGGAGCGTTCGATGGAGCTTCTCCATCACTTAATTT<br>GTCCCTTCAAGATGAAAAAGTAAGAGGTCCACCGTACCAAAACATTCTTCCACCCAGAAGAAAAACCACAGTAGCTGGAG<br>GGAGTCAAGCATGTCAGAAGCACAGAAACTGGGAATGGCTAAAAAGCAAGTCTTGACCCTTAACCCACCCCACTGGTTCA<br>CCTACCGCACCTCGGGTTAGGTATTGCTTGCTGAGGTGTCACTTTTCGCCAAAGTCATGTCTCTCTTTTGGAATCTTCTT<br>ATTGGTCCGTCTCGTTTCCTCGTTGCTGGATGCTGGTAGCGTTTTTGTCCATATATATATGCAGTCCATATGTATCCCCG<br>TCACTCCTCATCTATGCTCCTACCCGGCAACTTCCCACTACGATAAGCAGCAAGTTTTCGGCTCTGT |
| 39 | E. grandis Euc LIM | AAACACTTTCTGTAAACTTATTTTTGCAAACAATCCAAAGCCAAAAAAGTAAAGAAACTATTTTCAGATAGGAAATTTTT<br>CTCAAAACAAGGATCGTCGATGGGACTGGAGCTCTCAGCCCAAAAAAGAAAAAAAGAAAGGTAATGTGATGTAAGAGAGA<br>GGAAAGTAAGACAGTGTATGCAAAGCGACATGATGGGGAGAGCATTTGATGGACAATCATTGGGCCAACTCA<br>CATGAAGTCCTTACAACAAACAGTTGGAGGACGATGCAGCTCCAGCTCGATTCAGCGACTCCAATTATATTTCCCTCTCT<br>GGTCCTCTCCTCCTTTCCATGCGCAATCCAGCTAAGTTTCTATTCCATGGCCCCTTTGCTACTAGGGTCACATCTGCCAG<br>ATATTTTTCTGGTATGCAGCTAAAAGCATAGTAGTGCCCTTTGGAAAAGTTGATCATAGTAACTGGGCTGGTCCAGTTTA<br>ATTAGAGCAATCTATGATGAAATTACTAATGAATTTTTGGAAGTTCGGTTTTTGGTTTTCTCGGAATTTCTCACCAATAT<br>CATTGCTTCAATATTAGTTAAAATAGACGACTGAAAAGATCATGATAGATAAAAAAAAGGGAGTGGCCAAATTATTTTTC<br>TCTAATTCTTACTTAACTTAAGCTTCATGCATGCTGCCCATCTTGTGTTTGGTCATTAACTAACCTAGAAGGAGGGGGG<br>AAAAAGGTAAAACATGTCATAAAAGGTTTAGTTAGACCCTTCACCCAAAATGATTGCCCAATGCCACCACTTTAATCATCA<br>ACTTTCCAACCAACACTTGTTTTTTGGCTTCCCTTTCTTATCCTCCATTCTCCTCTCCT |
| 40 | E. grandis Euc 4CL | ATCAATGAGTGAAAGGGGCGGCACAAGAGAGATATACTTACACATGCTCCCCCTAGACTAGACGACGACGCAATTTAC<br>ACATGTCCGAGACATACGGTCATGAAATGGGAATTCTGATGTAGAAATAGCATGAACCCATTTAGCAAAGAATTGAGAAC<br>TGGGCCGGAACTCTGCTCGTGTTAACTAATCCAAGCGTCGGTCAAGCTGTGCGCACGCATGGGTGGGAAGGGGCGGGGG<br>TAGGTGCACAGGGAATTTGTTTGGGGGTTAGAGTTGGTCAAAAGCCGAAACGGTGTTAGGCATTGGGCTTTTTGGCTTT<br>CGGCTTCAAGACAATTTGAAGGGGAGATGGGGCGTGCCATCTGCTCTCCCCCTGCCATATGACCCATCATCCCCTCTCCA<br>TCTCCATCTACCTCTACCTACCCCGCCCCTTCCTCTTCTTCCCTTTTCTCTTTCCTTCTTGCAAAAATTTTAATTTA<br>TTAAAATATTTATTGCCCCTCCCCCTCCCCCTCTCCAAAACCGAATTTAACCCAACCCTCTCTCTTTCCCTCCACCCAAA<br>TCTCTACACATCATCATCATCATCATCATCTCCTCCCCTCCCTTTTCT |
| 41 | E. grandis Euc CAD | AAAATCACTTAACGGCTTCACCCAATATACTAGTTATCTCATAAGTGGCAATCTAAAAAAAAAAACACTATAGTTACGTC<br>GATGAAAGGTCCGACTTATCTGTTCGAAATCAGAACCTGAATTTCTATTATTGATCTAAACAAATCACGTCGAGTGTGAT<br>CTAGTTTATGAAAAATACTACAAAGAATGAAAAAAAAATGTTAAATTGAATGCAATTTATTAGCAATGGGTTTGAAAA<br>TTAGTAATAGTATATCTATTGTCATGCAAGATATGAATATTTAGATCCTTCTAGAAGCACGGATAACTTATGACTCGAT<br>GTTTTCTTAAATCTTTGGACACTTGTCATTTTTTCATGAGAAGCGACGAGAAGATCTTTCGCGGCTGTTTCACCTACCC<br>CAACCTTTGTCCCTATGCATCTTGGCTGAGATGTCAACCTTAGGCTTCCGACACCTTTGACTCTCTCTCCTCCATCGTCC<br>TCATCTCTCTCCTGTATA |
| 42 | P. radiata Cinnamoyl-CoA reductase | AAAAAGTTTCCCAATCTCTAAGCAACCATAAAGCTCAACCACTCTCTGTCCTGTGCCCCAACGTCTACCAGACGATTAG<br>GTATGCACTGCAGTTCTTCGTCTGTCATGCTACCAGACAGTTAGGTAACCACTAATGTCTTAGGTGGTGATTGATATTGA<br>TGTTTCTTCTGCAAACATGTGAATCAATGTGTATCGCTGGAATATGACACTGTGGATCACTGGATACATAGAGAGATC<br>TGCTCTGTCCATTTTAACAGATTCATCTCAATTTTCTTGTTCCAATGTCAACATTTTCTCAACTGCTCTGCCCCATCTT<br>TATTAAAGGGAACTACCCTGCATTTCCACACTCCAATC |
| 43 | P. radiata Cinnamoyl-CoA | CCTATAAAAAAGATTTTATTAAGAGCATTTGGAAAACTATCATCTTTCCAGGACCATAAAACTATTTAATAGTTCAATA<br>AAGATGAAGTAGTTACTATTTAATAGTTTAATAAAAATTAAGTAGTCTAACAGTTATATAGTTATATATATGTGTGTGTT |

TABLE 6-continued

| SEQ ID NO | Gene Homology | Sequence |
|---|---|---|
| | reductase | TTGGGTATGTTTTCAGGTTGAATGATGTATAATTGAGTAAGGATTTTTTTTGGAATTAGTGAATTTTTTTTTTCAGAAT<br>AACAATTCTATATATATCATAAAAATAAATTTTAAATAAAAAAAATCTAAATAAAAATTATTTAAAAAAACACTAAAACC<br>ATTAGTATACCAACACTTCAATTTAATGATGGATAAAATAATAAGCTAGCTCTGCTTAACATTACACTGTGGTGAGTTTG<br>ACATGAAAAAATAGATCTCTGCTTTCAGAAGTACGCATTTTTAAATTTAAAAAAGTTTCCCAATCTCTAAGCAACCATAA<br>AGCTCAACCACTCTCTGTCCTGTGCCCCAACGTCTACCAGACGATTAGGTATGCACTGCAGTTCTTCGTCTGTCATGCTA<br>CCAGACAGTTAGGTAACCACTAATGTCTTAGGTGGTGATTGATATTGATGTTTCTTCTGCAAACATGTGAATCAATGTGT<br>ATCGCTGGAATATGACACTGTGGATCACTGGATATACATAGAGAGATCTGCTCTGTCCATTTTTAACAGATTCATCTCAA<br>TTTTCTTGTTCCAATGTCAACATTTTCTCAACTGCTCTGCCCCATCTTTATTAAAAGGGAACATCTACCCTGCATTTCCA<br>CACTCCAATC |
| 44 | P. radiata<br>Phenylalanine<br>ammonia-lyase | AAAACTAATTTTCAAAATATGAGGAAAAAAGCGAGACCACGAAAAAATCATTGAAAAAGACCTTGCAAAATTCAGGACTT<br>GCTCTCACCAACCTCGCCAGGACTTTGACCGTGCTCATGCTTGTGTCATGCTTGCATATCTATACGTGTCACATCGACCG<br>TCCGATCTATCATGAAAAGAACGGTCATGATGAAATCTCAACTAAACCCACTGCGTTAAATTTTCGAACAGTGAGAAAGT<br>AATCGTATAAATACCCCTAAGCTCTTAGACCGAGAACGCATGCAGCATTCGGCTCTCATTCTGAGGTTCATCTGGCTGAA<br>GTTTGAACTGTGCT |
| 45 | P. radiata<br>Phenylalanine<br>ammonia-lyase | ATCATCACCAGTGCCACCTAAGAACGCGTTTGTATTGAGATACCATCTATTTTTTCGGATGCAATTACTAGTTAATAATT<br>TATAACATTATTAGGGGTGGGGTCCAGAAAAATGAAAAAAGAAAAAGAAAATTGAAATTTTAAAACTAATTTTCAAAATA<br>TGAGGAAAAAAGCGAGACCACGAAAAAATCATTGAAAAAGACCTTGCAAAATTCAGGACTTGCTCTCACCAACCTCGCCA<br>GGACTTTGACCGTGCTCATGCTTGTGTCATGCTTGCATATCTATACGTGTCACATCGACCGTCCGATCTATCATGAAAAG<br>AACGGTCATGATGAAATCTCAACTAAACCCACTGCGTTAAATTTTCGAACAGTGAGAAAGTAATCGTATAAATACCCCTA<br>AGCTCTTAGACCGAGAACGCATGCAGCATTCGGCTCTCATTCTGAGGTTCATCTGGCTGAAGTTTGAACTGTGCTC |
| 46 | P. radiata<br>Laccase | AAAGATGCTACAATTTGATTTCTTTTTAGTTAAATTTAATCAGAAATATAGAAAAAGGTTAGGAAGATGTTTGCAGTCGT<br>AAATATGAGCGCAATGGCCTTTAGTCCACGCGTAGTGGCACATCTTACACGGATACTTGGTTTTCAGCCCCACACAACTG<br>CAAGGGTTGCTTCGAAGGTAACTCTTACGTTGGTTTGAGTGCCCAAAACATATTAGCTTTTTATTTTGTGTCACTGTCGA<br>CATCGTTGGCCCTAATTTTATCGTATGATCAGGCCCTGATCTCTCTCGCCACCATTTCCTTATAAGGCGCCAGCAGACAA<br>GCACAGCTCTGGAAGGAACATGGGTGAGTGACATTAAAGCAACGCGATGACCTCATACCAGCTTCAACAGCTTACACCAT<br>AAGCACACGCTTTCCCATGGACATCCTCCTACGTATCACTCACTTGCCTATATATTCATGCAACTCCGTCACAGTTTTATA<br>ATAATTCAGGTGCCTTTTATATCAGTAGTATCAACGGATACACCCAGGGTGATTGT |
| 47 | P. radiata<br>Cellulose Synthase | AAATTCATGTTTGTCATAGGTTATGGTATTTTGCACACATGAAACAAATTTTACAATTGACTTTGATTAAGATATTAAAT<br>CTACAATAGGTTATCAACTCCACGTGATAATGAAGTAAAAAGACTGGATGGCTAAGTCAATAAAACAACCAAATAATCAA<br>GCAATGATAGCTTCTATCAAATAAGGATGGTTCAGCTAGATCCAGGCGAAATATGATTCAGCCAGATACGAAAAGGCGAG<br>CGGTTGAAATGTTTGAATGTTTGCGGGGTCCCTGGTTGCTTCGGAGGTTATTCTACGTAATTTATTCGTTATACCTTGCC<br>TTCTAAGCATCGCAAACTGTGATTTCTTAACAAACTCGATGCATGCGCCATAACCAACAAAACCATTTAGTTGAGTTTAC<br>GGTTCTTCAACAATTCATGCTCAGTCACCTTCACTATTATGACAGATTAGGTGCTACTTATTCTCTCGTTACCCTTTAGAG<br>TGAACTTTAATCTCAAATTGTCAGGTGATTTGGGCCCCCAGGCGATGGATCCAGCGACAGGGGAACGCAAGTTTGGTGGTT<br>GTGGCAGTGCAGTTGGTATGCCCCAGAGAGTTTAAGCTTCAGATTTGTGTTCAGTATCAGGAGCTGCTATGGAAAAAG<br>CAACCATATAAAACTATTGCCATTCGCACAGGAACAGAAC |
| 48 | P. radiata<br>LIM | CCTTTGGGAATGAACTTTGAGACCACCTCCAACCCGGATTCTGAAATCCATCCAGCAATTCCAAAGTTCCAAACCGAAAT<br>AAACATCCCACCATACCATGGCATTCGGAAAAAAGCTAGGCTAAGCTGAAAATCACTGTCATAACCCAGTAAGACCATGC<br>CACTAATAGCAAGAGAACCATACACCAACATGCAAAGCCATGCATGTCCAAACCAGCTAGGAAATCACACATGCAAAGGG<br>TTACCTGCAAGTATTCCTGTTGAAGTTGCTTGATCCTACTTTCTTTTCCTTGAGCCTTGCTTGCCTTCCTTTCCTTTGCT<br>TGATTTTCCTTTCCTTGCTCCAAACTAGAGTGCTCTAAGAAAACTCTAAGTGACCAAGAGAGTGAGAGAGAGAGAGAATA<br>ATGAGAGTCCAAACATGAACTTGACAAAAGCCATGAACTGATCCTCAGAAGTCATTTTATGCACGAGGCTTCTATTTTCT<br>TCATTTTCCATCATTTTCCTTCAATTTCCTCATCACATGCAACGTGCGACTTTTCACCCCGTTTTCCTCCTAATTTCTTT<br>TATTTTCATAAATAAATGTGCCAAAAATGCCTcTTGCCTTAGCCTTTGCCAGTTTCCTTAGCCAAAACACACATCCAATG<br>ATGCCCACTAGGATATCTTTGCCCAACATTAAGCCTGGAATAAAATGTCTCTTAATCGTGGTCTTATTTTGCTTTTATTAA<br>CTTTTTATTCATGAACTTTTCACTAAAGCTATTACAAAGATATATTTATTATGGCAATTATGTTTGATTTTTGAAGAGCT<br>AGTAACTTTTAGTTTATTATGGCCTTTTCCGTAAACTTATTTTCTTGAAAATCTCTATAAATCAATGAAAAATTTATAG<br>AATATATGTTGTGTTTCTTCACTACCTCTAATAAATTTTTACTTAGTAATCTACAAAGCCATTTATTAAAAAATTCAA<br>GTTAATTAAAATAATATCATTTCAAAAGTCTTTTTAATATAGTCAAAGTTTATTAAATTCTATGATGTATATTTCTTT<br>TAAATAAATGAAGAATCCATTTTTTTACTTAAAACCATATATTTTTTATAACGTTGATAAATAGCATGCATTTATATAAA<br>CAAATATATATTTTTATAACGTTAAGAGATTGTTAAAACTTTTAAATAATTAATATTTTATTTATTGTTTTGAAAATGTC<br>ATGATTTTCCACCTACCTCGCCCATCAAATCTTGCTGCAAACCAGGCTTACCCAACCCCACACCCACAATATATTTTGGG<br>ATCTGGTGCCCCCACCTTTGATCACAGTGAACACCATAAAGACAAATTATAAAGGCAAGGGGACTTGGCACCCATGAGGC<br>AACCGAAAGCAACAATCATTTTTTTCCAAAGAGATGAGTGTATGCCAACGAAGAAACACGATGAACCCACGTGTCATTG<br>GCCAACTCCCACTTTCGACAAAAAGAAGGAAATTAGAATTAAAAAGGCGAATAAAAATTGAAAGGCCATTTAAAATAGAA<br>GGAAGAATAGCCTATATGGTAGATTTAAATGCTTTTTTGAAATCCGGTTACTCGCAAGATTATCAATCGGGACTGTAGCC<br>CGAAGCTT |
| 49 | P. radiata<br>Expansin | AAATTAGTCAAATCCAAAGCAGACAACTTGGGCTCTCACCTAAATTAACACATATACCCTACCAGCTTCCATAGTTTCCA<br>ACTTCCTTTCAATAAATCTATTCAAAAGCATGAAAGCATGACTAAGGTTCAATTCCCAAGTTATGGACACCCACCTGCT<br>CTAGGCATATAGGAAATCACAATCCAACTAACGACCAACTACCCAAAACTTTGAAGAAATAGAGTAAAGACTCCCCCAGT<br>GATATTATAATTATATGGTCTCTCTAGAACCCTTTATTGCCCCTTCCAGTGTTATATTTAGTTCCCCATTTATATATCCC<br>TTGACTTATGAAACCATTTAGGTGCATTAACATAGTCCTTGACTAACAAAAAAATTATTTAGGTGCAGTAGATACGGAAA<br>GTAACCAATGATGCTAAGAAACTGTGCACGTACTTTAATGGAGGTATTACTTTTATTATGGTTGGTTTGGATACATTCAT<br>AATGGAAGCATGTGCTCTTCATCGTTAAAGTTGTGGTGGGGCATTCCCCATTTTCCACGAGAAACCGAATCCCGGCGTGG<br>AGACGACGACGAAATCGATGGATATTCGGTGGAAAATTCACGTAAAATTCCTGGAGAAAAAGGTTGCCGAGGTAGTTGA<br>AATCCAAACCGCCGAAATGAGCTGGAAACCCGCCTTCTGTCAGTTAGTTGAGTCATGACTGCAGCTGTCTCAGGTCTTAC<br>ACTGTAAAGGCACCTTAATGAGGCATTCATTCTGGCAGTCTGGCTACGGAACTTAATAGTACTTGTTATTCCTGCCCCAA<br>TATCTATTTAATAGGCATCCCCCCTCACTACTTCTTGCCCACAATCCCTCCATAGTCCTGAGCTTGAGACCATTTTTCTG<br>C |

TABLE 6-continued

| SEQ ID NO | Gene Homology | Sequence |
|---|---|---|
| 50 | P. radiata 4CL3 | AAATATAACATAATCTAACTATTGATGTACATTATTCGCCTATAACAAAATCTAAGTATTGATGTCACATTATTGGCATA<br>TAACAAAATCTTTAGGATAACCCCTTAGTCAAGCTCTTGTACTTTCATGTTTATTAACCAATAAATCAAGCTGATATGGA<br>ATAGCAGACGTACGTGGTAATAATAAATGGAGTGTAAGAGTTCGAACATTTTAATTCGGAGGGGCAGCTTATGTGGAATA<br>TCAGGCAATCATACAAGCTTGCTTTTGGGTAATAAAGACCCACATGTGGTAATAACAAGTGGATTTTAACAAACCAACAT<br>TTTGATAGGGAGGATAGGTGGCCTGGTAAGTTAGAATGTGCTAGTCATGCCTTTGAAAGAAGTTAGTTGTGGAAGTCAAA<br>CATGTTCCCCACACAACACACCTCACCACACAAAATGCTGGTAGGTCATGTGATTGATGGATGGGCATGTGTATCCTCCA<br>AAAAAAATGAATATACACACTAAATATTCTATTGACATAATATATACAAAGAAGATTAGGTCTATGGAAGAAGGGAAGGCGA<br>AGGGGAAGATTGGGTCGTGGGAAGATTGGGTCGTGTCCTGCTAGCACGTTGAATACCTACACGCCATTTCACATCTACC<br>CATCAACGTCAAATAGAGCATCCAAATCAGGGCGTGGTGGTGTGAGGGGAGAGTGAGGAGAAGAAGTTGAAAAATTCTGG<br>CTGAAAATCCACCTAACACACGCTCACCAGCCCCTCAACGAGGGGCACCAATTATGAATAATAATAGCTAGAACAGAGCA<br>GCAGAAGCAGAGTTTATATCTATCCATTGTCGTCTGTAAATTACTCTGTGAGTGTTTAGTGTTTTCTTCTCTTATTGATT<br>TCAGGGGACAAGTAGGTGGG |
| 51 | P. radiata 4CL1 or 2 | AAACACCAATTTAATGGGATTTCAGATTTGTATCCCATGCTATTGACTAAGCCATTTTTCCTATTGTAATCTAACCAATT<br>CCAATTTCCACCCTGGTGTGAACTGACTGACAAATGCGGCCCGAAAACAGCGAATGAAATGTCTGGGTGATCGGTCAAAC<br>AAGCGGTGGGCGAGAGAACGCGGGTGTTGGCCTAGCCGGGATGGGGGTAGGTAGACGGCGTATTACCGGCGAGTTGTCCG<br>AATGGAGTTTTCGGGGTAGGTAGTAACGTAGACGTCAATGGAAAAAGTCATAATCTCCGTCAAAAATCCAACCGCTCCTT<br>CACATCGCAGAGTTGGTGGCCACGGGACCCTCCACCCACTCACTCAATCGATCGCCTGCCGTGGTTGCCCATTATTCAAC<br>CATACGCCACTTGACTCTTCACCAACAATTCCAGGCCGGCTTTCGAGACAATGTACTGCACAGGAAAATCCAATATAAAA<br>GGCCGGCCTCCGCTTCCTTCTCCAGTAGCCCCCAGCTCATTCAATTCTTCCCACTGCAGGCTACATTTGTCAGACACGTTT<br>TCCGCCATTTTTCGCCTGTTTCTGCGGAGAATTTGATCAGGTT |
| 52 | P. radiata 4CL1 or 2 | ATCTTATGGAGTTTTTAAATATATATATATTTTTGGGTTGAGTTTACTTAAAATTTGGAAAAGGTTGGTAAGAACTATA<br>AATTGATTGAGTTGTGAATGAGTGTTTTATGGATTTTTTAAGATGTTAAATTTATATATGTAGTTGTGAAGGAGTGTTTT<br>ATGGATTTTTTAAGATGTTAAATGTGTATATGTAATTAAAATTTTATTTTGAATAACAAAAAATTATAATTGGATAAAAA<br>ATGTTTTGTTAAATTTAGAGTAAAAATTTTAAAATCTAAAATAATTAAACACTATTATTTTTAAAAAATTTGTTGGTAAA<br>TTTTATCTTAAATTTAGTTAAAATTTAGAAAAAAAATAATTTTAAATTATTAAACTTTTGAAGTCAAATATTCCAAATG<br>TTTTCCAAAATATTAAATTCATTTGACATTCAAAATACAATTTAAATAACAAAACTTCATGAAATAGATTAACCAATTTG<br>TATGAAAACCAAAAATCTCAAATAAAATTTAAATTACAAAATTATTTATTAACATTATGATTTCAAGAAAGAGAATAACCAG<br>TTTCCAATAAAATAAAACCTCATGGCTGGTAATTAAGATCTCATTAATTAATTCTTATTTTTTAATTTTTTACATAGAA<br>AATATCTTTATATTATATACGAGAAATATAGAATGTTCTAGTCCAAGGACTATTAATTTCCAAATAAGTTTCAAATCAT<br>TACATTAAAACTCATCATGTCATTTGTGGATTGGAAATTAGACAAAAGAGAATCCCAAATATTTCTCTCAATCTCCCAAA<br>ATAAACCTAATTAATATAGTTCGAACTCCATATTTTTGGGAATTGAGAATTTTTCTACCCAATAATATATTTTTTATA<br>CATTTTAGAGATTTTCCAGACATATTTGCTCTGGGATTTATTGGAATGAAGGTTTGAGTAATGAAGGTTTGAGTTATAAA<br>CTTTCAGTAATCCAAGTATCTTCGGTTTTTGAAGATACTAAATCCATTATATAATAAAAACACATTTTAAACACCAATTT<br>AATGGGATTTCAGATTTGTATCCCATGCTATTGGCTAAGCCATTTTTCTTATTGTAATCTAACCAATTCCAATTTCCGCC<br>CTGGTGTGAACTGACTGACAAATGCGGCCCGAAAACAGCGAATGAAATGTCTGGGTGATCGGTCAAACAAGCGGTGGGCG<br>AGAGAACGCGGGTGTTGGCCTAGCCGGGATGGGGGTAGGTAGACGGCGTATTACCGGCGAGTTGTCCGAATGGAGTTTTC<br>GGGGTAGGTAGTAACGTAGACGTCAATGGAAAAAGTCATAATCTCCGTCAAAAATCCAACCGCTCCTTCACATCGCAGAG<br>TTGGTGGCCACGGGACCCTCCACCCACTCACTCAATCGATCGCCTGCCGTGGTTGCCCATTATTCAACCATACGCCACTT<br>GACTCTTCACCAACAATTCCAGGCCGGCTTTCGAGACAATGTACTGCACAGGAAAATCCAATATAAAAGGCCGGCCTCCG<br>CTTCCTTCTCAGTAGCCCCCAGCTCATTCAGTTCTTCCCACTGCAGGCTACATTTGTCAGACACGTTTTCCGCCATTTTT<br>CGCCTGTTTCTGCGGAGAATTTGATCAGGTT |
| 53 | P. radiata Pectate Lyase | AAACAGAGCAGATAACACTAAAAAGACCAACCCTGTTAGGAGGGGAGAAACAAAAAGATCACACTAAAAAGACCAACCC<br>TCTTATCTAAACTTATTTTCTCTTATCTCTACCCCTTCTATTTTGAACCTTTATCATTTTGATAGAAAATATATGTTAAT<br>AACCATTAAACCTACATTGTCAAGCTAGTGTAACTTATATGTTAATAACCATTAAACCTACATTGTCAAGTTAGTGTAAC<br>TCCTTTGGTGGGGGTGGTTGTCTTCCTCTTCAATCTCATGCTATGACACACTTGTTTTTAATAACATAGGCCGACAAGT<br>TTGAGCCATTATCTATCTTGATTCCTCGAAATGATAAATAGATGTTGTCAGTGGACTTGAAAAAAACCAAGTAGGGAACA<br>CCACGTAATCTTTCCAATGGCATTAAAAGCTACTTTGAAATATGTAACACTTAGCAATCCTTCCAAGGCATTAAACCTAC<br>TCTAACCTATGGAACACTTAGCATCCTTCCCACGGTTGATAATAAATGATTGATTCCTCAGAATAACAAATAAAAAAAAA<br>CTATAAAACTTACTCTAAAATATAAAATGAGTATGGAACACGTGGCAATCCTTCCCATGCTCGGCGGTAGCTACTCTCTC<br>CAGAGATTTGAAATAACACAGGCGCCGCAATTATGAGAGAGCAGGTGGAGTTAAGACTTAGTAGCCATGGTTATTTTGAACG<br>CGTTGGCAATTCTTCCAAAGGTTGGTAGTTACTCTATCCAGAGATTTGAATAACACAAATGCTGCAGTTATGAGAGAGTAG<br>TAGAGTTAAGTCTTGTCAGCAATGATAGTTACGAACAACCGTAATTTCTGGCTATCTCTGTGTTTATTGGTCGTTTACTT<br>GCTACAGTGCTCTCACCCCACATGGTAACAGTGTTCGATGGCCATGATTTCTCCCCACCCCGCCAAACCTCTACGTTTTT<br>ATTCTTTTAATAACTCCTAATTTAATATATAAGAGGGGGCAAGGTGTTCATACAGATTCGTGCAAACGACCTGAGTTCAG<br>CACAAGTTTAGTCATTCCATGCGAACTCGACTGGCTCACGAGGATCCCTCGCTGCAGTTATAGATTGCAGGAATTAGCTTA<br>GCAGCATTTCTATCTATGATCTTCTGCCACTTCTTCCCCTCTC |
| 54 | P. radiata ACC Oxidase | AAGGTTTGCTTGGACCAGCGACACAGGGAAAAACATGGCATGCGGGTTTGGATTAAGATGAGGCCCAATCTTAATTTGAT<br>ATGTTTGCCAAACCTTAGGTTGTTTATCTAATTTTTGATTGGATCTGATCTCTTGATGATTTAAGGGTTTTCCATGTTGA<br>CACGCAATTGTAGGTTCCTGGGCACTAAGGTCTACCATGTGGCGAATTTATCGAGAGTTGACAATTCTGGTACTGTTAGT<br>GATTTGTCACCACTCTACGGTCCCTGCAGATCTCAGATTTTTAATGGCTGCCTTTGATTATCTAAAGGCTAGCCCCTAAT<br>CGCGGCTATGAATGTATAAAGAATGTGTTCAATGCATTAGAGTACTCAAAGACATGTTGAAGGAAAAGGACAAGTCAAG<br>GGACATGAGTAATAACCAAAAAAGCACTTGGTCCTGACCATCTGTGTCTGATTCACACTGGGATTCACATGTTATTTAAG<br>AAAAGTTGCATCAGTGCTGCAATCATCAAGCCATTCCTAATTTACCACCATGATTAGATTATTTAATGCAAGAAACGC<br>CTATATAAGGAGAGCTGCAGGCCCCAAGGTAATGCAGTAATCAAACTTGAGGAGAGATTTGAGAGTGTTTGTGAAGGG |
| 55 | P. radiata Dirigent | AAACGCTTCATGCCCCAGAAGCCGCACTCGATGCTTTAGAATAAAATGGACCATTACCAGATACGCGCCTCCAAAATAA<br>CAAAAACGTGTATTAGTTAAACCCTACATAGCACTTAAAGCTTGTCTTACTATTATTTTACGTAATTCTGTCTTTTTGAC<br>AGTGGATTGATTGGAACTTCCATTCTCGATACAGTTGTATGCGTTATGTGAACTGAACCAACCTCGGCCAAAATATGGGG<br>AAGATTCACTTCAGAAAAGACAGGACAACCATCTCTGATTGTCGACATTAATATCGGAAAAAATTCAGTCAAATGATGTG<br>GAAAAGGTTCATCTACGGAAAATAAAATAGCTCTGAGATGACCCGTTACATTTAGTGCATAGCATCTTTGTCAACAAGAAG |

TABLE 6-continued

| SEQ ID NO | Gene Homology | Sequence |
|---|---|---|
| | | AAATTTCCAGTTGTAGGACTGGTCATCAATGGCCGTGCCTGCAACGCTTTTTCGCAACAGGAAACACGGACTAAAAAACG<br>CGGTCTATCTGTCATTTGACGGTACGTTTGGCACTGAGCCCGAAAAATCCCATTGGTAGAATTTAGAAGAGGGAGCTTT<br>CACTCGAAAATTCTGTACCACAAGCGGTGGCCTCACAATAACAAATTATTATACCCACATGGAAATGTTAAATCGGACG<br>GTCCGACGGTCGACCAAAGACAAAATTGATGAGAAAGTTTTGAGGGTGGGTGATAAAGTAAGCGCGTCTTTTCACAGGCA<br>TCTGCATTATAAACCTGCAACTCCAACTTTCATCACAACAAATTTCATTTTCCCCTTCTCTGAGGC |
| 56 | P. radiata CSL | AAACAACAAAAAATAACAATCTACCTAGAAATTATATTACCAAATTTCAATTAAAAAACCCATTTCTTAGATTATTAAAC<br>TACACCATTATAATTTTCATAATAACTACTAATACACCATTATAAATTTCATAATACTATTCATCCCATTATAAATTTCA<br>TAATAACTTCTAATACACCATTATAAATTTCATAATACTATTCATCCCAATATGTGCTACCATTTAGATATTTTGAGCC<br>AAAACCCAACCCGAACAAAAATTTGTAATCTCGAGATTAATCACAAAATTTGACTCGATTCATATGCAAATTGGAATAAT<br>TACTCGTCATGGATGAGATCTTACCGTTGGTGTGATCATGATGACGGCCAACTTTGGCACGCTTCATATCACAAATTGCA<br>ACAACTACTCTGCTTTTAATGGATGACCATTGATGACGACCAAGCTTGACACGATTCATATGAGAGAAAGAACTCAAACA<br>ATCTACTGCAATGTGAAAAGCCATGGGCACCGCCAAGATATTTAATTGTCCAACGCGTAACAATTAGTTACCCCCAATGG<br>GCATTGGACTTGCCTTTGTCTTGATGTCGAAAACAAGGGGGGATTTCCTCTCTTTAAGAAAAATAGAAAAAACAAAACCC<br>CTGCACAGCTGGGTTCTCCTTTCTTCAAGCCTGGTTTGGCTTCAACATAAAGAAACAAAACCCATTCCATGGTGTTGTCT<br>TATTGTGGGTTTGCCTAATTCAATGTTATTAGTGGTTGAAACTTCATTACAGCAGGATGGGAGAGCCAACCTCAAGAGAG<br>TGACTCTGTAACCATCAATCTTCCGCATTGCCCTGCTGCCATGGATGTACTGGCGAAAATAAAGGGTCAACTTTGCTTAA<br>AGATGCAGTCAGCTAGAGTTTAACTCAAGGAGGCAACCGGCTTCTATGTAATACCTGTGGAATGAAAACGAATCCCATGT<br>ACCGAATTAAGGGAAAACTGGGTGCAGAGATTTGTTTGGTTTAGACTCTAGATATGGTATTACAGCTCCGATTGGGTGG<br>TCGAAATACGTCAGAGCACCCCACATTGCGTAATTCTTCAGGTATCAGATGCCTGCCTAGTCTACATACATGAGTTGCAG<br>TTTCTCTTCAGCAGTGGGGTTTGGCGGCTCTGACAGTACAGTTAGTAGAGACTATCTATTTTCCGTGTACACAACGCTTG<br>CAATGCAGATCTGGGCGCTATTATAAAAGATCAAACAAGAGCTAGGCTTTCAGAATTGCCTGAAAGCTGCTGCCAATTGC<br>ATAGATCTGCTCAAGGCACCAC |
| 57 | P. radiata CSL | CTGTATTCATCACTTTACACCCATGATTCCAAACCCTACACATTTACACTGATAACCAAGGGTTCAGGTTCTTTCCAATT<br>CATTTTAATCCAGGATGATAATAAATTTGAATAGCACAATAGCATATTCCAACTGaCATATCCCTACATTTGGGATCTCT<br>TTCCACGTTATAAATGGCTTCAATTTAGGGATCCCTTTCCACATTATATAACTGGGTTCACAGTGGTTTGAAGATAGCTG<br>TGGTTTGAAGATAGCTGTATATGTTATCAAAATGACAGCTCCCTTGCCAGGGACCATCGCTTGAATGATGAGATCCCGCC<br>TGTAAGGCAACTTGCAGCATGATTATTTTACATCTGCTTGACCAATTATCTAACAATATACGCGGTGTCGTCGTTCGGTT<br>AAATAATAGTGAAACTTCCTCGTGTTGTCCCTGCAGTTACGTATGTCTTGTTCTTTTTTTTGTTTAATAaCATACAGCAG<br>AGCAAGTGTTGGGTGAATAAATATTGGGAAGAAGCTGCAGCGTTCACGTTCATTCATTCACTCATCGTGAGCAGCAGTAC<br>ATCAACAGTTCTTGAAGAACATTGATAGGTTGGCTATTTCAATCCTTTCATGGGGAATATTTAAGTCTGGATCCGAGC |
| 58 | P. radiata CSL | ATCTTATCACATTTTCTCAAGAGAAGGGTTGTGACCAACTTTAAATTTTGGTCTCTTTGATGGTGGTAAATTGGGGCAA<br>TGAGACTCAACATTGTTAGAACATTTACCTTTCTCATACTTTGGAGGATCTATTAAGACAAAAGCTCTCATGTATTTCCT<br>TTACATGCATGCACATTTATAGGGAATAGAATGGAGTAGCAAATTGACTTTCTAAGGAAGGCCTACTCTTGACTCGGGGG<br>TTGTGGCAGGTAGTTGAAGACTAGGGAGCCGGTCACTACCAATTTTACCATCAACCATTTACAGACGAGATACAAAATGA<br>TGATTATGTTTAATTTTTGAAACTTTCACTTATTAATTTTTGTGACGCATTCATAACATATTATGTTAGTATATATGTTC<br>GTTCACAGGTTGTTGGCTTTGGTAACACTATACTAGTATTTCTTTGTGATTATTTTTATGTAATGCAATATAGCCCTAA<br>ATGAATATTGTGAAAGTGATATTTTTCAGGAGCATCAAGACCATCTTCATTTGTAAATATGTGATAAAAGGGGGTGTGA<br>TAAATTTTAGTATTTTGTTATTTTAATAAAATAGGAAGTGAAGATTATGTAAATATTATTTTCTAAATAAAAGGATATG<br>AGAGAATAGTTTAGGAAAAAGAATTGGGATAGAATTTCTATGTTTTTTCAATTAAAATTAGGATAAGAATGGAGAATAAA<br>GCTTCACGCTTTAAATCATTATGTAAAACGGAAAAAGCCTGCTTTTGTAAAAGATAAGGTCGAGAAGACCTATCCCTTA<br>TGTATGTATCCGTTATTATTATAAATAAAGAGGTAGCTAATCTCTCAAGGGAGAGAGAGGAGCGAGCGCTCGGAAAAAG<br>ATGGATGATGTCTTTGTTAATATTGTTAATATGGATGCGCGTAGTTAATAGTTTATTTGGACTGTGTATTAAGCATTGAAT<br>GGTTAGCTGTATATGTTATCAAAATGACAGCTCCCTTGCCAGGGACCTTCGCTTGAATGATGAGATCCCGCCTGTAAGGC<br>AACTTGCAGCATGGTTATTTTACATTTGCTTGACCAATTATCTAACGATATACGTGGTGTCGTTATTGGGTTAAACAATA<br>GTGAAACTTCCTCGTGTTGTCCCTGCAGTTACGTATGTCTTGTTCTTTTTTTGTTTAATATCATACAGCAGAGCAAGTG<br>TTGGGTGAATAAATATTGGGAAGAAGCTGCAGCGTTCACGTTCATTCATTCACCCATCGTGAGCAGCAGTAGATCAACAG<br>TTCTTGAAGAACATTGATAGGTTGGCTATTTCAATCCTCTCATGGGGAATATTTAAGTCGGATCCGAGC |
| 59 | E. grandis Laccase | ATCAATTCAAGTAAAAAATTTTAATCCTAACTTAGTCATAAACTTTTATGCAATATTCCAATATAATCCGTCAGTCAATA<br>TTAATCGGAATTGTTGACGTAGCGATGCGCCACGTAGAATGACTAACGATGGCTAAACCGCTATAGTAGCGATTTCTGAC<br>AAATATTAACTGAATGACTATATTTTCCTCATTATTCAGGTTATATTGTTTTGTTTTCATGCTATTTCCCCAATAGCAAA<br>TTTGTTCACCTGCTCCTGGAAATTCCTTACGACGACTCACCACTTATTCTAACGAATCTGATGGGTGATTCTTGATATTA<br>TTTGACCATGACATAATAAATGTCAAGGGAAAAGAGAAAAAAATAAGAAAAGCGAAGAAATCCACCGGTCATCATTAGG<br>ACAGACACATTATACGCCGTCATAAGGGAAAATGAAATTTAACTAAACATCACTAACGTCAACCAAACTCGAAAACAAAA<br>CTTGAACTGCAGTAGCTAGATGTAGCTCTTGGTTCAGCCCCCAGAACCATCGCCTATCGGGTTGATGGTTGAAGATGTGA<br>TCTTGGTCCTAATCACCTAATCAACGAACCACCGTTTCTCATTCGCTCCCTCCGTATAAAAACCTCGAGGCTTGTCCTAT<br>CTTGGAGCATCGCATCCAAGAAACACCATCTCATCCGTCTCAGTCCCCATCATCACTTG |
| 60 | E. grandis Tubulin alpha chain | GTCGTTTTTATATTGTCTAGCCACATTAGCATGAAAAACAATGTTGTTTTGCATTTCCTTTGTCGGAAAATTGCCGCGTT<br>GGCATTTTGGTTGGAATGACACTTAAATGATCCATTTTGTTTTGATTTTGACACTTAAGTATTACTTTCCAAAGTTTTGA<br>CACTTAAGTGTCCATTCGCACTAAGTTTTGGCATTTGAGTGTTCCTCCGTATCAAGTTTTGACATTTGTAATGTACTTTT<br>GCTCATAATGCTAATGTGATAATGAGACTAAATTAAACATATATTAAAATTTCAGAATCTACATTAAATAATTTAAAAAT<br>TTATGACTATATTACATATTACGATAAAGTTCAAGAACTATATTAAAAAATTAAATATTTATGGGTCACATTACATAC<br>GAGTGAAAATTTAAGGACTATTTATTTTGTTATTTCTTTTTCCATTAACAAAAATCTTCCCCACCTCATTTTAAATTCGA<br>GAAAAGAAGAAAGCAAAGAAAAATAATAGAGAGGAAGGGACCCAACTCGAGATTGGGCTCCATTGATGGAAACTCGCGA<br>TCTACTCCATCTCGACTCGACAGCCCATCCTCTGAAGATAACATCATCGTCCGCACCGCATTGCACCCTACCTTCTGGGC<br>TGAATGACCACATTGCCCCTCCACCAAATCTATCCGTTGCCTGAATGCCGGATGGCAAAGCAGCAATTCCCGCAAAAGT<br>CCGAGCCCATTTCCCTCCGGCCAAATCGAGAAAGGACTCTTGATTTTTGAAAACTGGGCGGGCAACTAACCTTGGTTAGG<br>CGCCTCCATCATTAACCCCACACCAAAGTTAACACCCCCGCTTTCGCTGGCACTTTCTAAATCGAACCGCGGTTAACGTA<br>ACCGCGGTTAACCAACCAGATATTTTTCAATTTTTTCCAGTGGCGCTCTATATATCTTTAAACTTCCCCTCTGCATTTCC<br>CATCAGCTCTGCAAGTCCTCCTCCATCTTCTTCTTCTTCATCGTCATCTTCTCGGAAGGCGTCTTGATAAAC |

TABLE 6-continued

| SEQ ID NO | Gene Homology | Sequence |
|---|---|---|
| 61 | *E. grandis* Coniferyl Alcohol glycosyltransferase | ATCAAAGTTAGTCGCACTTTTACATACCCAACTGTACCTCCAAAGTGCACCATTGAACTTGTGACAACGTTTAGATTTAG<br>GTAATTATTCAGAAAACGAAAGCGACCACAGGTTTATGAATTGTCACGCATGACGTCATTAATTAAGCGACAAGACGTGC<br>GCCAAGGCCATGCATTCCTCTGCGGCTATCCTTCTTCCTGGCAACAGTTCAATTCCTCAGACGGTCTGGTCAAACCCGAA<br>GCTCGACTAGGCCTTTCTCAACCAAACCCTCCAAGAAAGCCTAAGGACAGCATGCCCTCGCGCGGATCAACACGACCGAC<br>GAGCATCGAACTTGCGTAACTTACCCCACCAAACGGTCCCCTTCGAGGTCAAACCCCACGCGAACGACCGATGAATCGAA<br>CATCTAATCTGCCTCTCCTCCTCCACTGCTATATATTTCAGCTACTCTAACACACTCTCATCACCACCAACTTCAAA<br>CTCTCTCTCTCCCTCCCTCCCTCTCGCTCACACATACACACAT |
| 62 | *E. grandis* CONSTANS-like B-box Zinc finger protein | CTGGAGTTCACATTGAGCTGGTGCCGATCGATCCGTTTCTTACATTTTTTCATCCCGGTCCGTCTCCATTCTCTGCCTCC<br>GTCGGCATCTTGGGCGACGAGAGGAGGAGGAGATACGCGGTAGCTGACGAGTTCGAGGCGCAACTTTTCTTCGATTAACT<br>TTTAACTCGACACCGATCATGCTTTAAGCACTTACCCTTTTCGAGAAACAGGAGATGGACATGGAGTTCGACGTAAAGAT<br>CCCGTCTTTGATTACAGAAAAAGCATGCTCAGAGGAGGAGGAATGATATTTCCTGTTTCCATGGTGGTGATAAAAGCTTT<br>GATTTTTCCTTTTCAATGACGTAGCTCGAGTGGCCGATAATCGACAAGGAGGTCCAACTATTAGCACCAGAATGGAAAAG<br>AAGAGGGAGATAGATAGCGACTACCACAAGCTACATTACAAGGATTAATATAAGCAAAATTACTGCAATACGATATTGAC<br>CCGATTGGCTTTGGATGATAAAAAAACAATTCTATATTCAATCACACGTCTTCGTCCCCGGGAAAGCAATGATCCAAATC<br>ATGTCAAGGAGCTATACTCCTAAGCCCACGTTAGCCCACACTCTTCTCGAAAGACATATCAAATCAATACACTCACTCTC<br>TCTATTAATATTCAATTTCTGCATAATTTCTTCTGTCACTGCCCAAGACGTTCTGTAGCACTAAGGGGTG |
| 63 | *P. radiata* Alpha Expansin | AAATTCACATTCTTTTTCTTCGCACGAAGAAAGGTTAAAGATACAACTCGGATTGTATTAAAGGAAAGAGATTGGAACAA<br>ACAGAATCTGGAATATAAGAATACACCAGATCGCGGGCACGGCCACAGTTTAACGGCCAGCCGAAAGGCCGGTCCGTTGG<br>GTCTGCCGGTGACTTGGCTCGTGTGAGGGAATCTCTGGAGTCCGGATCCGGTCTTGCCTTGCCTTGAGACCTACCACAACCACAGC<br>AGTTAATGCAGTTTACATCCTATTAATATAAATACCAAATCGCCATTCCAAATTATTATCACAACAACAAATCTGATTTG<br>ATTTCGATGCAGTGAAGCTCTTCATTTTGCAGTGACAGTGACGTT |
| 64 | *P. radiata* Tubulin Beta Chain | GGACAAACGAGATTTTATTCTCATCCAGTTCCATCTATTCTCTGTCACTGTAACTTGTAGAGATTATATTAACGATGGGG<br>TTATGATCGCTTCACGTTTCCAGATAGAATGGAGAGAACAACAGCAAGGAAATCGACAGGCCATAACTTAATGGGGTCAC<br>TGTAAGGCCTTCCGGGGCGTAAACACGAAGCTTTGTACAGAGAGTCCACCCAAAACAAGCATCATCACAGTGACAATAA<br>TTGAAAAAGAAATGAAAAGCTCCACTGGGCTTCTCTTTCTGGAACCTTCTCTCCGAAGAAATCGACTTACAGAATTTAAA<br>AAATTTAAAATGATGTTCTGTAGCAACCTAGGCCCTCCACTGTCACATACCTGCCCCTCCATTGTCACATTCTATCTTC<br>TCATCTTAAACACCACGCATCTCGCTTTTCCACTGCATGCAGAGATCGACGATATCTTTGCTTGATATCTAAGTCGAATT<br>CTGACCGCAAACCTCCATCAGACTTGCGCACATCTTAATAGATGGCGCTTGTTTGTGCCCAAGGGGTTCTGGGTACTATT<br>TGAGGACTGAAGGTGTTATGCTTCAGAGATTTGGAGGCCTAGGGTTCGATTCACAGCCGTTGAGATTTCGACAGAATTTG<br>GATTTTTTTCTCTGGCTGTTTGAGGAGAATGAGAGAGATATTGCACATCCAGGGCGGCAGTGCGGGAACCAGATAGGA<br>GCCAAGTTCTGGGAAGTGATATGTGACGAGCATGGGATTGATACCACGGGCTCGTACTGTGGGGATCCGATCTGCAGCT<br>GGAGAGGATCAATGTCTATTATAACGAGGCAAGCGGCGGCCGCTATGTGCCTCGGGCAGTGCTGATGGATCTCGAACCCG<br>GGACCATGGACAGCGTTCGATCAGGTCCCTATGGTCAGATCTTCAGGCCAGATAACTTCGTCTTTGGGCAGACAGGCGCC<br>GGGAACAACTGGGCCAAAGGGCATTATACTGAGGGGGCAGAACTCATTGACTCCGTTCTTGATGTCGTGCGTAAGGAGGC<br>CGAGAGCTGCGATTGTCTTCAGGGATTTCAAGTATGTCATTCCCTGGGAGGAGGAACAGGATCGGGAATGGGGACTCTCT<br>TGATTTCCAAAATAAGGGAGGAGTACCCAGACAGAATGATGTTGACTTTCTCTGTTTTTCCATCACCTAAGGTATCGGAC<br>ACAGTGGTGGAACCTTATAATGCAACTCTTTCTGTACATCAATTGGTGGAGAATGCAGATGAATGCATGGTTCTTGACAA<br>TGAAGCACTTTACGACATTTGCTT |
| 65 | *P. radiata* Putative Beta 1,3-Glucanase | GTATCATTATTTCAGTCATTATCGATAATGATAAGCCTCAAATATGAATCAATAGTCTCTTAGTCATTTAATTTATGGTT<br>TTCAGTGTCGATGTGCTCTCCTGCCAGGGCTCCACCAATCTCCTTTAGGTTCAGTGTACATCGTCTGAAATAAGTTGAC<br>AAGGCCAGGTCAATGCAGAAGCCTCCTGGCTTGGGGACCCTAAGTGTGAAATCAATATATTTTCCTCGAGTTCTTGACCT<br>GTTAGCAACTTCGACACTGCAACTTGTCCTAATCTTTGCTGTGTATTATGTATTTTGTTCCAAGTATTGGAGTGTAGCAC<br>AGTGGATGGTAGAGGAGGATCTAGATCAGTCACTTTTACATAGAATGGAGATGATAGTAAAAGCAACTACAATTACGA<br>TCTTGCTACCAGTCATCCTATGTTGCATCCCATGTGGAGAAAGTGGAAGCGGAGGCAGGAGTTTGGCGCAGCGTTTACCA<br>GCCCTAGGCGTTGACTATGGACAAACTGCAGACAATCTTCCTCCACCATCTGCAGTAGCAAAGCTGGTTCAGAGTACAAG<br>TATTTCAAAGTTGAGACTATATGGAGCAGATCCTGCAATTCTTCAAGCATTTGCTAACACAGGAATTGGGTTAGTTGTAG<br>GCATTGGTAACGATCAAATCCCATCTCTGAACCAGCTGGCTGTTGCACAGAATTGGATTAAGAACAATATCGTTCCTTTT<br>GTTCCTGCCACTGATATCATTGGAATCTCGGTGGGAACGAGGTTCTGTTCAGTGGGGATGGGAGTCTGATTTCCCAGCT<br>CCTCCCTGCATTGCAGAACCTACACACTGCCCTTGTTGAGGTTTCACTTGACCAGCAAATTAAGGTCTCCACACCTCATT<br>CTCTGGCCATACTTTCTACATCTGTCCCCCATCTGCTGCGTTTCAATGAAAGTTTTGACATGAAATCCCTGCTTGAC<br>TTCTTGCAGAAGATAGGGGCCCCATTAATGATCAACCCATACCCCTACTTTGCTTACAAGAGTAATCCCACCGATCAAAC<br>CTGGCTTATGCACTCTTCGAGCCCAACCCGGGCTTCTATGACACAAACAGTGGGCTCACCTATACCAACATGTTTGATG<br>CTCAGCTTGATGCAGTGTACTCAGCCATGAAATATCTGGGTTACCCTGGTGTTGATATAGTGGTGGCTGAAACAGGATGG<br>CCAGCTGTGGGGGATCCTACAGAGACAGGGGTGAGCTTACAGAATGCAATTGCTTACAATGGCAACCTGATCAAGCATGT<br>GACGTCCATGACGGGGACCCCATTGAGGCCAAATAGGTACATTCAAACCTATATTTTTGCCCTCTTTAATGAGGATCTGA<br>AGCCAGGACCAACTTCGGAGCGCAATTATGGGCTGTTTAAAGTTGATATGACAATGGCTTATGATGTGGGTTTGTTGCAA<br>TCGCCAGTGCAGCTCCATCCTCCTGCTCCACGCACTGGGGGGCCTGTGACAACTCCTCCTACAGGTAAAGTTTGGTG<br>CATTGCCAAGCCGGGCGCCGAAGAGCAAACTTTGGAGGCAAATTTGAACTATGTTTGTGGACAGGGCATTGACTGTAGGC<br>CTATTCAACCAGGAGGTCCTTGCTATTCACCAAATACAGTGGCAGGCCATGCTGCTTATGCCATGAATGGCACATACTATCAG<br>ACTGCGGGTCGGAACAATTGGAATTGTGATTTTGCGCAGACGGGAACTCTTACCTCCACAGATCCAAGCTACGGGCCTG<br>CGTGTACCCGACCGTCTAAGATATGAATCAATCAATCAATCCTAGTGTTTTCTATTCCACTTGTTGTTCGGTATATATTT<br>TCCAACTTGTCTTTTCATATGAGTGAGATGTATGAGGTACCTATTTTCAAAGTTGTGATAGCATATACATCATAAGATGT<br>AATGTGTATGTTTGGGTTTATTCCCCCTTTAATGTCGTTACTCTGACCATATAAAAAAATTCACAGAATTTGTGAATGG<br>TAGTATTATTTTTATTTATGTATTAAGGAAATTTAAGTGGTGTTAAAAAAAGGAAAAAAA |
| 66 | *P. radiata* Cinnamoyl-COA Reductase | AAAAAAAATTATGATCTGTAAATAAATATAATTCCATATATAATAGATATATATAAATTTTACAACCCACAGATAAATAT<br>TAACTTTCCGCCAAATAATTTCCATAAATGAAATAAATGACCCAATATTACGATTTTACACCAAAATGATTTCCATATG<br>TATATATAAAGCCTGTGAGTCCAAACGAAGCATATGAATCTGAATCGCAGAGGGAGGCTGGCCAACCACCATTAGCTATT<br>CAATGAAGTTGGTAGCCACCCAAACAAGTCAATTCAAGAGTCAATCAAACCAAACTATGATTAAAACTACCAACGCACT<br>TTCTGAGCAACCCACTTTCCCTCCCTCGCTTTACTTTTTGGAGTCGTGGGGGATTTTTCCAGTGTCTCAATTTCTATAAA |

TABLE 6-continued

| SEQ ID NO | Gene Homology | Sequence |
|---|---|---|
| | | TTTGGCCTCACATTTCCTACCAACTCATTGTTAACGGGAGTCCTCTTGTCAGGCTCCGCTGCTTCTTGTGATCACACGAT ACCTAGTGATCCATAGATAACTAAAATGCTGTGAGCAGTCTGAATTCTTGCTTTCTTTCCCC |
| 67 | *P. radiata* Dirigent | GTCTGTATTATTATATTCTGGGTCACTACTCAACCCCACGGTAGTGGCGTGACTTGCGTCGGCGTGTTACAGAATCCATA ATCAGAAAACGAACGGAAGCTGCAAAGGTGTACGTCCAACGGTTGCGGTGAAAAGCCATTGGTTACGTCCAGCGGTGGAA TTCTGTAATACTGAAAGGATTTGGTTACAGATGGCTCGACCAAAGACAAAATAGTAATCAAATATTCAACCGAAAGGGAG AAAGTTGCTTATGGGCATCACGTTATAAAAGTGGAACTCGACTTTCATTACCACACATTTCTCATTTCTTTCTCTGTACT GAGCCATTCGTTCTCCTTTCTTTCAGAGA |
| 68 | *P. radiata* Caffeic Acid OMT | CTGGCAACTGGCTATTCCTCATTCGTCAGTGGGAATGGGGTGGGCAGACGATCTTCTAGAGCCTGTGTGGTGTGGGGCCC TTCGACTTTTCAATGGCCCGTTGGTCACCAGCTTGGACTAGTTTTGCTGTTTCCATGGTGACGGTTCGTGCTCTATAAAA TAATTTAACCGAGTGGGTATTTTGCATGGTGGCCGGATTTCCAACAATCTCAGGTATTAGCG |
| 69 | *P. radiata* High Mobility Group Transcription Factor | ATCTAACCCACGATCTATAATAATAGTCAAGGACCCTAAATAGAAATATGGCCACCACCCTACCACGAGAGCTTATCCTA ATACAACCACGAAAGCCCCTCCACTCGTGGAGGTTATAGATTTCCCCCGTGTAAACATATAAAAGGAACTTTTCTCTTTG GTGACCGGCAACAACCGGATACTCACCCGGTATCGCCGAAGAAGCTTGTTGCGAGGTTCGCATTGAAAACCTCCTCTCT TCACATTCTTTGCCGGTCATCCATCTTGCTCATTTCTACTTCCGCCTCCTCTTCTCTTCCCTCGTCTAGTGTTTTCTTTG CGTTGTGTAGTGTAATGTTTGCTGTTGCTTCATATCAATAGTGGTGGAATTTTCCTTCACTGCGAGCAGATTTTCTAAGG AGA |
| 70 | *E. grandis* Tubulin alpha chain | GTCGTTTTTATATTGTCTAGCCACATTAGCATGAAAAACAATGTTGTTTTGCATTTCCTTTGTCGGAAAATTGCCGCGTT GGCATTTTGGTTGGAATGACACTTAAATGATCCATTTTGTTTTGATTTTGACACTTAAGTATTACTTTCCAAAGTTTTGA CACTTAAGTGTCCATTCGCACTAAGTTTTGGCATTTGAGTGTTCCTCCGTATCAAGTTTTGACATTTGTAATGTACTTTT GCTCATAATGCTAATGTGATAATGAGACTAAATTAAACATATATTAAAATTTCAGAATCTACATTAAATAATTTAAAAT TTATGAATCATATTACATATTACGATAAAGTTCAAGAACTATATTAAAAAAATTAAATATTTATGGGTCACATTACATAC GAGTGAAAATTTAAGGACTATTTATTTTGTTATTTCTTTTTCCATTAACAAAAATCTTCCCCACCTCATTTTAAATTCGA GAAAAGAAGAAAAGCAAAGAAAAATAATAGAGAGGAAGGGACCCAACTCGAGATTGGGCTCCATTGATGGAAACTCGCGA TCTACTCCATCTCGACTCGACAGCCCATCCTCTGAAGATAACATCATCGTCCGCACCGCATTGCACCCTACCTTCTGGGC TGAATGACCACATTGCCCCTCCACCAAATCTATCCGTTGCCTCGAATGCCGGATGGCAAAGCAGCAATTCCCGCAAAGT CCGAGCCCATTTCCCTCCGGCCAAATCGAGAAAGGACTCTTGATTTTTGAAAACTGGGCGGGCAACTAACCTTGGTTAGG CGCCTCCATCATTAACCCCACACCAAAGTTAACACCCCCGCTTTCGCTGGCACTTTCTAAATCGAACCGCGGTTAACGTA ACCGCGGTTAACCAACCAGATATTTTTCAATTTTTTCCAGTGGCGCTCTATATATCTTTAAACTTCCCCTCTGCATTTCC CATCAGCTCTGCAAGTCCTCCTCCATCTTCTTCTTCTTCATCGTCATCTTCTCGGAAGGCGTCTTGATAAAC |
| 71 | *P. radiata* WD-40 Repeat Protein | AAATAGGCTAAATTAGAGAAATACTATGGGTTGTCAAAACCTAGAATACGATAATTTGACCGAAATATTTAGATAATGTA ACATAACATGACATGACATTACAACATCTCTTCCATAGAGAATCTCTCAATAAAATAAAATATTGCACAAACAAAACCAA CTCAAACTCAATTTATATTACACAATATAATAATAAACAATTTCAATTAAAAACATTTTACCTTTATTTATTAATAAAC CTCACACTAACACATTGTTAAAAAAGTAAAATAAAATAACAAACGCCATATAAACCCATAAAAATTTCCAAAACAATATT AATATCTTTATCATAGTTTTTAAGCTAAAGTTCGATGATCCTTTAACATTACTAGCCACAAGGATGCTTACTTCCTTGCA AAATAACAATGCAAAGACCCAACGCAGTGATATGTGATTTAACGGTAAGTATGGTTGGGTGAAACCAACAAGACTGCAGT TCAAATTCCATTGAGTATATGGCCTGCTATGATCTCAGCTTGGTGAAACCAACAAGACTGCAGTTCAAATCAAATCCCA TTAATTATGTGACCTACTATAATCTGGGCTTAAGGAGTAGGTTGCTCGCTATGTTTTGGTGTTATAAAGTAGCCATAAAG ATTAAACCTCAAGCTCCCCTAAATTAATCCAAGAAATTACCGATTCATTATAATTAAAAAAATGCAAATACCCACCTTA AAGAAAACAATGTAAAGAGCAATGAAATCAATTTAATTGTCTTCTTTTAACACCAATAAAAATTTATAAAAACCTCATA ATTAAAAACAAAGCGTTAGACTTTTGGAATAACCTTCCTTAATTGCTTCTCTAATTTATGATTTCTAAGTCATACCACGA TCGGTCGTTTTAGCAAAAGCCTGAAAGGCAAGTAGAAGATAAACGTATGCTTGAAATAAATATATGTCATTTTTCATTT TATATCCTTCGAATCCGTCATTCGTCTGAATGATCAGACAAACCCTCCCAGATCCTGCTCTGTTCTGAAGCATAAACCT |

What is claimed is:

1. An isolated nucleic acid molecule comprising the sequence of SEQ ID NO: 47.

2. The isolated nucleic acid molecule of claim 1, wherein said sequence is operably linked to a gene encoding an RNA interference molecule.

3. A vector comprising the isolated nucleic acid molecule of claim 1, wherein said sequence is operably linked to a gene encoding an RNA interference molecule.

4. A plant cell transformed with the vector of claim 3.

5. A transgenic plant comprising the plant cell of claim 4, wherein said transgenic plant expresses said gene encoding said RNA interference molecule.

6. The transgenic plant of claim 5, wherein said plant is selected from angiosperms and gymnosperms.

* * * * *

SEQUENCE LISTING

<160> NUMBER OF SEQ ID NOS: 86

<210> SEQ ID NO 1
<211> LENGTH: 168
<212> TYPE: DNA
<213> ORGANISM: Eucalyptus grandis

<400> SEQUENCE: 1
aaaaccacaa atggccgcgg gacgtcacaa tttttttttc cttctagaag ctctatagtc    60
aaagctgatc tataaatttt tgggaaccac aaccaccatg tctcgccacc ttcgctcgaa   120
ccttatcacc accaccgccc ttgagccctc ctccatcaac tcttcttc                168

<210> SEQ ID NO 2
<211> LENGTH: 934
<212> TYPE: DNA

<213> ORGANISM: Eucalyptus grandis

<400> SEQUENCE: 2

```
aaaacaatgt agcttctctg tgttatgaaa actaacaaaa gggcacatct atttctccat    60
gaccattata ttcggaggag catggtcaaa cttaaatcaa aatttattat ccataactta   120
caaatttcca atttagctaa actcaaatcc caaagtatag caattctgtt aaaattttat   180
catccgatag tatagagcaa tatttttataa tacttacatt gctcagctca attacaaatt   240
ctatttgtcc acaaattcaa acattttaat gatgcattcc acataaaacc aatggtttga   300
gacacctttt caaaaaaaag aaaaaaatac actagcattg cttagacaag ttaatcaatg   360
aaaaataact ttatcttgtt tttaattaag gatgaaaagg agttacaaac gcttgtttca   420
agataaatat ttttcaaatc tttaatatta caagaaataa acggaccttc ttatcaacca   480
aaaaaatgta acataaaagg aacttaccaa tttgattgga ctcatttatt gattttgga    540
aaaatgtcgc aaattttcgt tgagttttag ctccatgtac aatttagtca ttgaactttt   600
aatttattca atataattca tgaactttct atacatattt agtccatata aaaattaagg   660
gaccaaattg agtattcacc aaaatttag ggaaaatatt gaataaataa aagttcttg    720
gaccaaattt catattgaaa taaaattcat ggacaaatca ttattccttg attaaacttt   780
tttatgtaga cacccgtaaa tacaacctgc caaggtttgt ttgcaaggcg tttgcaaggc   840
gtttgcactt aagcgggacg gaggcgtcac cagtcaatgg gcatgtccag tggcttcccc   900
ggcttgcgaa taggatgctt cctgaatcat ctcc                               934
```

<210> SEQ ID NO 3
<211> LENGTH: 408
<212> TYPE: DNA
<213> ORGANISM: Eucalyptus grandis

<400> SEQUENCE: 3

```
aaagtttctc tgtagagaga gggagggaga tatatctgcg gtttgcgtct ctatttcgct    60
tgtgcagttt tactactccc caaacacaca cacactctct ctgtttctct cctttttccc   120
caaatcagaa gaagaaacga cagtgtagta gtgcagtttc actacaccgt ctatactaag   180
ggtaatcgtt tttttgaaag cacatgcata tagccgttgg aaaggggagg gcaccgagat   240
cgaatcggat ggctgatcct cactagccgt tagagagaga gagagagagg gagggataat   300
catgtgcgga catatatccg caatttgcgt ctctatttcg cttgtgcagt tcactactc    360
cccacacaca ctctctctct ctctctctcc ttttcccccca aatcagaa               408
```

<210> SEQ ID NO 4
<211> LENGTH: 847
<212> TYPE: DNA
<213> ORGANISM: Eucalyptus grandis

<400> SEQUENCE: 4

```
ccttgtattt ccccaacatt aaatgaaagc ctacatccaa aaacgtggac ccggcattaa    60
agaaaaaccc catcatctca tcccatcctt tatttcaacc ctaaagtgaa attaagatat   120
aagacgaaac caccccccaac ccccaaaaa aaaaatatta agggaattcg tttttttgaa   180
agcacatgcg gaggtagctg ttggaaaggg gcctctacgt tcggaaggaa tgcgaccatt   240
ccatcgagat caaatcgaac tactgatgct cactagctgt tgcgtttaaa ccttctttgt   300
aaagcgataa gggaattcgt tattttgaaa gcacatgcgg aggtagccat tggaaagggg   360
cctctacgtt cggaaggaac acgaccgttc caccgagatc gaatcggacc gttgatgctc   420
```

```
actagccatt gtgtttaaag tttctctgta gagagaggga gggagatata tctgcggttt      480
gcgtctctat ttcgcttgtg cagttttact actccccaaa cacacacaca ctctctctgt      540
ttctctcctt tttcccccaa atcagaagaa gaaacgacag tgtagtagtg cagtttcacc      600
acaccgtcta tactaagggt aatcgttttt ttgaaagcac atgcatatag ccgttggaaa      660
ggggagggca ccgagatcga atcggacggc tgatcctcac tagccgttag agagagagag      720
agagagggag ggataatcat gtgcggacat atatccgcaa tttgcgtctc tatttcgctt      780
gtgcagtttc actactcccc acacacactc tctctctctc tctctctcct tttcccccaa      840
atcagaa                                                                 847

<210> SEQ ID NO 5
<211> LENGTH: 286
<212> TYPE: DNA
<213> ORGANISM: Eucalyptus grandis

<400> SEQUENCE: 5
aaattatgca atttcttaat caggcctagc tagaaacaag ggcaaggaaa gcccccgacg       60
ggctcttatc tgctgacgtg gcacgccgtg ggtgggcccc ccgggtcttt ccttcgacga      120
aacctcatcg tagacaatca aatcctcctc tcgatcatta ttgcaaagcc aacacccagc      180
attgaatcga tccccacctt ctcctcctcc tcctcttgat cctttttgtc ccgatgatga      240
tgggtatctg atcagccgat tcaatcccat cgtctccttc cttctc                     286

<210> SEQ ID NO 6
<211> LENGTH: 216
<212> TYPE: DNA
<213> ORGANISM: Eucalyptus grandis

<400> SEQUENCE: 6
gtgcggacac gtgtcccctt atcccgccca agaccgcgca aaacctgaaa atcctcacta       60
ttccctcact ttcggcgaat tcgaaacagc gcataaagga acacggaaag aacattctct      120
accccaagac gacgacgacg acgacgacga cgacgccgcg ccttatataa accatcgcca      180
ctcctggcca ttcccttctt tctccccaga tccaat                                216

<210> SEQ ID NO 7
<211> LENGTH: 473
<212> TYPE: DNA
<213> ORGANISM: Eucalyptus grandis

<400> SEQUENCE: 7
aaagataaaa atagtgtgga aaatagattt gagaagtgtt catatatttc gatttatcat       60
agcaaagatt ttatcgacct attttaggct ttatagtgtg actatttaag ataacgaata      120
ttaatcgaga gatgcacaat taataagaga tattctcacg atcttgagat atatagaaac      180
cgacagaaaa tatattgatt atctctaata tagaataata ttctagagaa gtattgtaat      240
tgtgaccacc aactaaaatg gggcagacaa agtagagggc caggtatagt caaggccagt      300
gaaaaggaaa atgaaatgaa ataaaagaaa agaaagaaa aatcaaatcc tccaacttgt       360
gtacaggata cacccgaagc tttgtgtata taaaggccac ttaatatctc ctccaaccta      420
gcaacacatt cgaaagataa gttgcgctta aatcctctcc aaaagagcta atc             473

<210> SEQ ID NO 8
<211> LENGTH: 519
<212> TYPE: DNA
```

<213> ORGANISM: Eucalyptus grandis

<400> SEQUENCE: 8

```
ctgctgaaat tctcgaggaa gttgagaggt tccagattag atctttacca aacaaaaaaa      60
aactattgct tatgctaaat tggtcattat aataagattt ttagaatact cgttgagtat     120
actcaactca agatattata agttttctca attggttttt ctccatttct tatgatccgt     180
ccacgagctt ggagtcgctt tgaagatgt agccagccca acagaaccgt ttccttcatc      240
ttcccgcgaa agtttcatgt catctccctc ctctgcatca cgaaccaaac ctctgctctc     300
tctctctctc tctctctgct tcaacacaat gacaccaaca tcgcaccctc ctcaccttcc     360
caaccaccgc ataccatct cctttaagca ttccgatgag tccctgatcc accgccttct      420
cactgagcct tcccgctctc cctcttctcg tctcactttc tcatataaag aagtgaaaga     480
atacgaggat actccacttg ggtatcgcca agaactcat                            519
```

<210> SEQ ID NO 9
<211> LENGTH: 1607
<212> TYPE: DNA
<213> ORGANISM: Pinus radiata

<400> SEQUENCE: 9

```
cctttgggaa tgaactttga gaccacctcc aacccggatt ctgaaatcca tccagcaatt      60
ccaaagttcc aaaccgaaat aaacatccca ccataccatg gcattcggaa aaaagctagg     120
ctaagctgaa atcactgtc ataacccagt aagaccatgc cactaatagc aagagaacca      180
tacaccaaca tgcaaagcca tgcatgtcca aaccagctag gaaatcacac atgcaaaggg     240
ttacctgcaa gtattcctgt tgaagttgct tgatcctact ttcttttcct tgagccttgc     300
ttgccttcct ttcctttgct tgattttcct ttccttgctc caaactagag tgctctaaga     360
aaactctaag tgaccaagag agtgagagag agagagaata atgagagtcc aaacatgaac     420
ttgacaaaag ccatgaactg atcctcagaa gtcattttat gcacgaggct tctatttct      480
tcattttcca tcattttcct tcaatttcct catcacatgc aacgtgcgac ttttcacccc     540
gttttcctcc taatttcttt tattttcata ataaatgtg ccaaaaatgc ctcttgcctt      600
agccttgcc agtttcctta gccaaaaacac acatccaatg atgcccacta ggatatcttt     660
gcccaacatt aagcctggaa taaatgtctc ttaatcgtgg tcttatttg ctttattaa       720
cttttattac atgaactttt cactaaagct attacaaaga tatatttatt atggcaatta     780
tgtttgattt ttgaagagct agtaacttt agttattat ggccttttcc gtaaacttat      840
tttcttgaaa atctctataa atccaatgaa aaatttatag aatatatgtt gtgtttctt      900
cactacctct aataaatttt ttacttagta atctacaaag ccatttatta aaaaattcaa     960
gttaattaaa aattaatatc atttcaaaag tctttttaat atagtcaaag tttattaaat    1020
tctatgatgt atatttcttt taaataaatg aagaatcca ttttttactt aaaaccatat    1080
atttttata acgttgataa atagcatgca tttatataaa caatatata ttttttataac     1140
gttaagagat tgttaaaact tttaaataat taatatttta tttattgttt tgaaaatgtc    1200
atgatttcca cctacctcgc ccatcaaatc ttgctgcaaa ccaggcttac ccaaccccac    1260
acccacaata tattttgggg atctggtgcc cccacctttg atcacagtga acaccataaa    1320
gacaaattat aaaggcaagg ggacttggca ccatgaggc aaccgaaagc aacaaatcat     1380
ttttttccaa agagatgagt gtatgccaac gaagaaacac gatgaaccca cgtgtcattg    1440
gccaactccc actttcgaca aaagaagga aattagaatt aaaaaggcga ataaaaattg    1500
```

```
aaaggccatt taaaatagaa ggaagaatag cctatatggt agatttaaat gcttttttga    1560
aatccggtta ctcgcaagat tatcaatcgg gactgtagcc gaagctt                 1607

<210> SEQ ID NO 10
<211> LENGTH: 1163
<212> TYPE: DNA
<213> ORGANISM: Pinus radiata

<400> SEQUENCE: 10
aaacagagca gataacacta aaagaccaa ccctgttagg aggggagaaa caaaaaagat      60
cacactaaaa agaccaaccc tcttatctaa acttattttc tcttatctct accccttcta   120
ttttgaacct ttatcatttt gatagaaaat atatgttaat aaccattaaa cctacattgt   180
caagctagtg taacttatat gttaataacc attaaaccta cattgtcaag ttagtgtaac   240
tcctttggtg ggggtggttg tcttcctctt caatctcatg ctatgacaca cttgtttttt   300
aataacatag gccgacaagt tgagccatt atctatcttg attcctcgaa atgataaata    360
gatgttgtca gtggacttga aaaaaccaa gtagggaaca ccacgtaatc tttccaatgg    420
cattaaaagc tactttgaaa tatgtaacac ttagcaatcc ttccaaggca ttaaacctac   480
tctaacctat ggaacactta gcatccttcc cacggttgat aataaatgat tgattcctca   540
gaataacaaa taaaaaaaa ctataaaact tactctaaaa tataaaatga gtatggaaca    600
cgtggcaatc cttcccatgc tcggcggtag ctactctctc cagagatttg aataacacag   660
gcgccgcaat tatgagagag cagtggagtt aagacttagt agccatggtt attttgaacg   720
cgtggcaatt cttccaaagg ttggtagtta ctctatccag agatttgaat aacacaaatg   780
ctgcagttat gagagagtag tagagttaag tcttgtcagc aatgatagtt acgaacaacc   840
gtaatttctg gctatctctg tgtttattgg tcgtttactt gctacagtgc tctcaccccca  900 catggtaaca gtgttcgatg gccatgattt ctcccccaccc cgccaaacct ctacgttttt   960
attcttttaa taactcctaa tttaatatat aagaggggggc aaggtgttca tacagattcg  1020
tgcaaacgac ctgagttcag cacaagttta gtcattccat gcgaactcga ctggctcacg  1080
agatccctcg ctgcagttat agattgcagg aattagctta gcagcatttc tatctatgat  1140
cttctgccac ttcttccccct ctc                                          1163

<210> SEQ ID NO 11
<211> LENGTH: 881
<212> TYPE: DNA
<213> ORGANISM: Pinus radiata

<400> SEQUENCE: 11
aaattagtca atccaaagc agacaacttg ggctctcacc taaattaaca catatacccct    60 accagcttcc atagtttcca acttcctttc aataaatcta ttcaaaagca tgaaaagcat   120
gactaaggtt caattcccaa gttatggaca cccacctgct ctaggcatat aggaaatcac   180
aatccaacta acgaccaact acccaaaact ttgaagaaaa tgagtaaaga ctcccccagt   240
gatattataa ttatatggtc tctctagaac ccttttattgc cccttccagt gttatattta   300
gttccccatt tatatatccc ttgacttatg aaaccattta ggtgcattaa catagtcctt   360
gactaacaaa aaaattattt aggtgcagta gatacggaaa gtaaccaatg atgctaagaa   420
actgtgcacg tactttaatg gaggtattac tttttattatg gttggttggg atacattcat   480
aatggaagca tgtgctcttc atcgttaaag ttgtggtggg gcattcccca ttttccacga   540
```

```
gaaaccgaat cccggcgtgg agacgacgac gaaatcgatg gatattcggt ggaaaattca      600
cagtaaaatt cctggagaaa aaggttgccg aggtagttga atccaaacc gccgaaatga       660 gctggaaacc cgccttctgt cagttagttg agtcatgact gcagctgtct caggtcttac     720
actgtaaagg caccttaatg aggcattcat tctggcagtc tggctacgga acttaatagt     780
acttgttatt cctgccccaa tatctattta ataggcatcc ccctcacta cttcttgccc      840 acaatccctc catagtcctg agcttgagac cattttctg c                          881

<210> SEQ ID NO 12
<211> LENGTH: 638
<212> TYPE: DNA
<213> ORGANISM: Pinus radiata

<400> SEQUENCE: 12
aaggtttgct tggaccagcg acacagggaa aaacatggca tgcgggtttg gattaagatg      60
aggcccaatc ttaatttgat atgtttgcca aaccttaggt tgtttatcta atttttgatt     120
ggatctgatc tcttgatgat ttaagggttt ccatgttga cacgcaattg taggttcctg     180
ggcactaagg tctaccatgt ggcgaattta tcgagagttg acaattctgg tactgttagt     240
gatttgtcac cactctacgg tccctgcaga tctcagattt ttaatggctg ccttttgatta   300 tctaaaggct agcccctaat cgcggctatg aatgtataaa gaatgtgttc caatgcatta    360
gagtactcaa agacatgttg aaggaaaagg acaagtcaag ggacatgagt aataaccaaa    420
aaagcacttg gtcctgacca tctgtgtctg attcacactg ggattcacat gttatttaag    480
aaaagttgca tcagtgctgc aatcatcaag ccattcctaa tttaccacca tgattagatt    540
attttaatgc aagaaaacgc ctatataagg agagctgcag gccccaaggt aatgcagtaa    600
tcaaacttga ggagagattt gagagtgttt gtgaaggg                            638

<210> SEQ ID NO 13
<211> LENGTH: 900
<212> TYPE: DNA
<213> ORGANISM: Pinus radiata

<400> SEQUENCE: 13
aaatataaca taatctaact attgatgtac attattcgcc tataacaaaa tctaagtatt      60
gatgtcacat tattggcata taacaaaatc tttaggataa ccccttagtc aagctcttgt    120
actttcatgt ttattaacca ataaatcaag ctgatatgga atagcagacg tacgtggtaa    180
taataaatgg agtgtaagag ttcgaacatt ttaattcgga ggggcagctt atgtggaata    240
tcaggcaatc atacaagctt gcttttgggt aataaagacc cacatgtggt aataacaagt    300
ggattttaac aaaccaacat tttgatatagg aggataggtg gcctggtaag ttagaatgtg    360
ctagtcatgc ctttgaaaga agttagttgt ggaagtcaaa catgttcccc acacaacaca    420
cctcaccaca caaaatgctg gtaggtcatg tgattgatgg atgggcatgt gtatcctcca    480
aaaaaaatga atatacacac taaatattct attgacataa tatacaaaga agattaggtc    540
tatggaagaa gggaaggcga aggggaagat tgggtcgtgg ggaagattgg gtcgtgtcct    600
gctagcacgt tgaatacccta cacgccattt cacatctacc catcaacgtc aaatagagca    660
tccaaatcag ggcgtggtgg tgtgagggga gagtgaggag aagaagttga aaaattctgg    720
ctgaaaatcc acctaacaca cgctcaccag ccccctcaacg aggggcacca attatgaata    780
ataatagcta gaacagagca gcagaagcag agtttatatc tatccattgt cgtctgtaaa    840
ttactctgtg agtgtttagt gttttcttct cttattgatt tcagggaca agtaggtggg     900
```

<210> SEQ ID NO 14
<211> LENGTH: 603
<212> TYPE: DNA
<213> ORGANISM: Pinus radiata

<400> SEQUENCE: 14

| | | | | | |
|---|---|---|---|---|---|
| aaacaccaat | ttaatgggat | ttcagatttg | tatcccatgc | tattgactaa | gccatttttc | 60 |
| ctattgtaat | ctaaccaatt | ccaatttcca | ccctggtgtg | aactgactga | caaatgcggc | 120 |
| ccgaaaacag | cgaatgaaat | gtctgggtga | tcggtcaaac | aagcggtggg | cgagagaacg | 180 |
| cgggtgttgg | cctagccggg | atgggggtag | gtagacggcg | tattaccggc | gagttgtccg | 240 |
| aatggagttt | tcggggtagg | tagtaacgta | gacgtcaatg | gaaaaagtca | taatctccgt | 300 |
| caaaaatcca | accgctcctt | cacatcgcag | agttggtggc | cacgggaccc | tccacccact | 360 |
| cactcaatcg | atcgcctgcc | gtggttgccc | attattcaac | catacgccac | ttgactcttc | 420 |
| accaacaatt | ccaggccggc | tttcgagaca | atgtactgca | caggaaaatc | caatataaaa | 480 |
| ggccggcctc | cgcttccttc | tcagtagccc | ccagctcatt | caattcttcc | cactgcaggc | 540 |
| tacatttgtc | agacacgttt | tccgccattt | ttcgcctgtt | tctgcggaga | atttgatcag | 600 |
| gtt | | | | | | 603 |

<210> SEQ ID NO 15
<211> LENGTH: 1631
<212> TYPE: DNA
<213> ORGANISM: Pinus radiata

<400> SEQUENCE: 15

| | | | | | |
|---|---|---|---|---|---|
| atcttatgga | gtttttaaat | atatatatat | tttttgggtt | gagtttactt | aaaatttgga | 60 |
| aaaggttggt | aagaactata | aattgattga | gttgtgaatg | agtgttttat | ggattttta | 120 |
| agatgttaaa | tttatatatg | tagttgtgaa | ggagtgtttt | atggattttt | taagatgtta | 180 |
| aatgtgtata | tgtaattaaa | attttatttt | gaataacaaa | aaattataat | tggataaaaa | 240 |
| atgttttgtt | aaatttagag | taaaaatttt | aaaatctaaa | ataattaaac | actattattt | 300 |
| ttaaaaaatt | tgttggtaaa | ttttatctta | aatttagtta | aaatttagaa | aaaaaaataa | 360 |
| ttttaaatta | ttaaactttt | gaagtcaaat | attccaaatg | ttttccaaaa | tattaaattc | 420 |
| atttgacatt | caaaatacaa | tttaaataac | aaaacttcat | gaaatagatt | aaccaatttg | 480 |
| tatgaaaacc | aaaaatctca | aataaaattt | aaattacaaa | atattattaa | cattatgatt | 540 |
| tcaagaaaga | gaataaccag | tttccaataa | aataaaacct | catggctggt | aattaagatc | 600 |
| tcattaatta | attcttattt | tttaattttt | ttacatagaa | aatatcttta | tattatatac | 660 |
| gagaaatata | gaatgttcta | gtccaaggac | tattaatttc | caaataagtt | tcaaaatcat | 720 |
| tacattaaaa | ctcatcatgt | catttgtgga | ttggaaatta | gacaaaagag | aatcccaaat | 780 |
| atttctctca | atctcccaaa | ataaacctaa | ttaatatagt | tcgaactcca | tattttggg | 840 |
| aattgagaat | ttttctaccc | aataatatat | ttttttata | cattttagag | attttccaga | 900 |
| catatttgct | ctgggattta | ttggaatgaa | ggtttgagta | atgaaggttt | gagttataaa | 960 |
| ctttcagtaa | tccaagtatc | ttcggttttt | gaagatacta | aatccattat | ataataaaaa | 1020 |
| cacattttaa | acaccaattt | aatgggattt | cagatttgta | tcccatgcta | ttggctaagc | 1080 |
| cattttcctt | attgtaatct | aaccaattcc | aatttccgcc | ctggtgtgaa | ctgactgaca | 1140 |
| aatgcggccc | gaaaacagcg | aatgaaatgt | ctgggtgatc | ggtcaaacaa | gcggtgggcg | 1200 |

```
agagaacgcg ggtgttggcc tagccgggat gggggtaggt agacggcgta ttaccggcga    1260
gttgtccgaa tggagttttc ggggtaggta gtaacgtaga cgtcaatgga aaaagtcata    1320
atctccgtca aaaatccaac cgctccttca catcgcagag ttggtggcca cgggaccctc    1380
cacccactca ctcaatcgat cgcctgccgt ggttgcccat tattcaacca tacgccactt    1440
gactcttcac caacaattcc aggccggctt tcgagacaat gtactgcaca ggaaaatcca    1500
atataaaagg ccggcctccg cttccttctc agtagcccccc agctcattca gttcttccca    1560
ctgcaggcta catttgtcag acacgttttc cgccattttt cgcctgtttc tgcggagaat    1620
ttgatcaggt t                                                          1631

<210> SEQ ID NO 16
<211> LENGTH: 786
<212> TYPE: DNA
<213> ORGANISM: Pinus radiata

<400> SEQUENCE: 16
aaacgcttca tgccccagaa gccgcactcg atgctttaga ataaaatgga ccattaccag     60
actacgcgcc tccaaaataa caaaaacgtg tattagttaa accctacata gcacttaaag    120
cttgtcttac tattattttta cgtaattctg tcttttttgac agtggattga ttggaacttc    180
cattctcgat acagttgtat gcgttatgtg aactgaacca acctcggcca aaatatgggg    240
aagattcact tcagaaaaga caggacaacc atctctgatt gtcgacatta atatcggaaa    300
aaattcagtc aaatgatgtg gaaaggttca tctacggaaa ataaaatagc tctgagatga    360
cccgttacat ttagtgcata gcatctttgt caacaagaag aaatttccag ttgtaggact    420
ggtcatcaat ggccgtgcct gcaacgcttt ttcgcaacag gaaacacgga ctaaaaaacg    480
cggtctatct gtcatttgac ggtacgtttg gcactgagcc cgaaaaaatc ccattggtag    540
aatttagaag agggagcttt cactcgaaaa ttctgtacca aagcggtgg cctcacaata    600 acaaattatt atacccacat ggaaaatgtt aaatcggacg gtccgacggt cgaccaaaga    660
caaaattgat gagaaagttt tgagggtggg tgataaagta agcgcgtctt ttcacaggca    720
tctgcattat aaacctgcaa ctccaacttt catcacaaca aatttcattt tccccttctc    780
tgaggc                                                                786

<210> SEQ ID NO 17
<211> LENGTH: 898
<212> TYPE: DNA
<213> ORGANISM: Eucalyptus grandis

<400> SEQUENCE: 17
aaaaaattta taactaatat tggtacaatt agaaattctc ttgccttcct taatcttgct     60
gttaactcct ccatttttagg cgtagacaac tatttttttt ccacaaaaat gaaacagttc    120
ctaaatagac taacgccttt taagctggta gtagacagac cgacacaaaa tcctgaacag    180
gcatgtaccg acacaaagag attcatttca cgagtaaatt tgaatttcga caactaattc    240
tacacatcgg taatcacgca aatatatcag atcggcaaaa agttatattt tagacagtga    300
cgtgacatct caagcaccca atccctctca acaggtgaag agccatattt tcattacata    360
aaggcatttt ttttttttaa ttttttaatag gtggtccgac cgacaagata ttattatttt    420
tctatttgca tgaagaagaa aaagattggt tttgaccaca atggtttgtc ctctcgttac    480 ccatttttata tttggcaagt ttggtgattg attgtagaag aaacacgaaa cacgcgagca    540
aaagtaaagg actccaaacc caaatttttaa tccacaaacg aatttaccca cataaaaaaa    600
```

-continued

```
ggggagatta tgattaaatt cgttgaataa tgcgacccct taggagaagg cttattaagc    660
aagcatcgac ggaagctaca cactccttt gggagaggc tagtgggtgc aacaactacg      720
attcgggtag agctaagctt tgtccccagt ggcggtactg ccatgaccag ggctctaaat    780
caaaacctaa tctgccaacc tcaaaacaaa cgctgtctcg ccccccccgg ctgcgctata    840
taatgcagcc gatggcgtcc ttcctttctc gaaccctaag cagatcaaga gtttgagt     898
```

<210> SEQ ID NO 18
<211> LENGTH: 563
<212> TYPE: DNA
<213> ORGANISM: Eucalyptus grandis

<400> SEQUENCE: 18

```
gtgaagagcc atattttcat tacataaagg cattttttt tttaattttt aataggtggt     60
ccgaccgaca agatattatt attttttctat ttgcatgaag aagaaaaaga ttggttttga   120
ccacaatggt ttgtcctctc gttacccatt ttatatttgg caagtttggt gattgattgt   180
agaagaaaca cgaaacacac gagcaaaagt aaaggactcc aaacccaaat tttaatccac   240
aaatgaattt acccacataa aaaaggggga gattatgatt aaattcgttg aataatgcga   300
ccctttagga aaggcttat taagcaagca tcgacggaag ctacacactc cttttgggga   360
gaggctagtg ggtgcaacaa ctacgattcg ggtagagcta agctttgtcc ccagtggcgg   420
tactgccatg accagggctc taaatcaaaa cctaatctgc caacctcaaa acaaacgctg   480
tctcgccccc ccggctgcg ctatataatg cagccgatgg cgtccttcct ttctcgaacc   540
ctaagcagat caagagtttg agt                                          563
```

<210> SEQ ID NO 19
<211> LENGTH: 524
<212> TYPE: DNA
<213> ORGANISM: Eucalyptus grandis

<400> SEQUENCE: 19

```
aaatttttt ttttttttgg gtgggtagta ggatctgtca gagtaaagtg acttaacgcc     60
aattctcgac atttcagact aataaaatat ttacagatgc aacgtctcac tctctccttg   120
caaaaccaga aagggacagc aagcaagaag agggggaaga gaagacttgc gttttaagca   180
aggggagtgc tgacttttca agcgacttaa ttaatctgtt tagcacccac tttggttcgt   240
ttgatcttct cgtgatttat tatttaccta tgtacagctg cggttgaaat ggcctctctc   300
gcttaaatgg tagtttgtcc ttttcttggg gtggttgctt tggaaatatt cttttagaag   360 cagggggcaaa gaaatggagt ggcatctgat gcttcttcaa cactttgcag ccatatcgag   420
aatatatacc tagagagaga gagagagaga gagagagaga ggagcagtgg agaagaagga   480
gaagaagaaa agggtcagat cagatccagt tgttgggagc aagt                    524
```

<210> SEQ ID NO 20
<211> LENGTH: 638
<212> TYPE: DNA
<213> ORGANISM: Pinus radiata

<400> SEQUENCE: 20

```
ctgtattcat cactttacac ccatgattcc aaaccctaca catttacact gataaccaag    60
ggttcaggtt ctttccaatt cattttaatc caggatgata ataaatttga atagcacaat   120
agcatattcc aactgacata tccctacatt tgggatctct ttccacgtta taaatggctt   180
```

```
caatttaggg atcccttttcc acattatata actgggttca cagtggtttg aagatagctg      240
tggtttgaag atagctgtat atgttatcaa aatgacagct cccttgccag ggaccatcgc      300
ttgaatgatg agatcccgcc tgtaaggcaa cttgcagcat gattatttta catctgcttg      360
accaattatc taacaatata cgcggtgtcg tcgttcggtt aaataatagt gaaacttcct      420
cgtgttgtcc ctgcagttac gtatgtcttg ttcttttttt tgtttaataa catacagcag      480
agcaagtgtt gggtgaataa atattgggaa gaagctgcag cgttcacgtt cattcattca      540
ctcatcgtga gcagcagtac atcaacagtt cttgaagaac attgataggt tggctatttc      600 aatccttttca tggggaatat ttaagtctgg atccgagc                              638

<210> SEQ ID NO 21
<211> LENGTH: 862
<212> TYPE: DNA
<213> ORGANISM: Pinus radiata

<400> SEQUENCE: 21
aaatataaca taatctaact attgatgtac attattcgcc tataacaaaa tctttaggat       60
aaccccttag tcaagctctt gtactttcat gtttattaac caataaatca agctgatatg      120
gaatagcaga cgtacgtggt aataataaat ggagtgtaag agttcgaaca ttttaattcg      180 gagggggcagc ttatgtggaa tatcaggcaa tcatacaagc ttgcttttgg gtaataaaga      240
cccacatgtg gtaataacaa gtggatttta acaaaccaac attttgatag ggaggatagg      300
tggcctggta agttagaatg tgctagtcat gcctttgaaa gaagttagtt gtggaagtca      360
aacatgttcc ccacacaaca cacctcacca cacaaaatgc tggtaggtca tgtgattgat      420
ggatgggcat gtgtatcctc caaaaaaaat gaatatacac actaaatatt ctattgacat      480
aatatacaag gaagattagg tctatggaag aagggaaggc gaaggggaag attgggtcgt      540
ggggaagatt gggtcgtgtc ctgctagcac gttgaatacc tacacgccat ttcacgtcta      600
cccatcaacg tcaaatagag catccaaatc agggcgtggt ggtgtgaggg gagagtgagg      660
agaagaagtt gaaaaattct ggctgaaaat ccacctaaca cacgctcacc agcccctcaa      720 cgagggggcac caattatgaa taataatagc tagaacagag cagcagaagc aaagtttata      780
tctatccatt gtcgtctgta aattactctg tgagtgttta gtgttttctt ctcttattga      840
tttcagggga caagtaggtg gg                                                862

<210> SEQ ID NO 22
<211> LENGTH: 693
<212> TYPE: DNA
<213> ORGANISM: Eucalyptus grandis

<400> SEQUENCE: 22
aaacggacag gaaccaaact ggatcggatc caattcctag tcctaaaacc aaccaatccc       60
cactttctaa tttttggaat cggtcctata ggttccattt gaaatcgat cgcccttata      120 tgaatgaaag agcgctcaca tgtaccgtta gatggtatag acctaataat ctgataatct      180
gatggctcat tgcgttttga gctcacatgg agcgagatta tgtaataatg acgtcaggga      240
gaggagagga gagaagatga agagaaagct gtggagaaac aaaacacaag gctcgttgga      300
agcaacgtaa acaacagcaa acaacatcaa caacggcgac aaaagaagag agagagagag      360
agagagagag aggaaacaaa aacaaaagca aaagttgggg agtgaagagg ggaaaagaaa      420
gatgatgtga aaacaaacca aactctcctt ttcttccacc tctcattttc tgtctggtat      480
atgggggtct ctctctctct ccctctctct ctctctctct accttctctc tctacttttct     540
```

```
ctttcttagg ggggggcgtc cccagggtct ccgatcccaa tatcattccc ccccactctt      600
ttgctgccat atacatacaa aaaaccgaag cttgtgaaca acccatctct ctctctctct      660
ctccctctct ctttctgcct gcgaaactgt gtc                                   693

<210> SEQ ID NO 23
<211> LENGTH: 934
<212> TYPE: DNA
<213> ORGANISM: Eucalyptus grandis

<400> SEQUENCE: 23
aaaacaatgt agcttctctg tgttatgaaa actaacaaaa gggcacatct atttctccat       60
gaccattata ttcggaggag catggtcaaa cttaaatcaa aatttattat ccataactta      120
caaatttcca atttagctaa actcaaatcc caaagtatag caattctgtt aaaattttat      180
catccgatag tatagagcaa tattttataa tacttacatt gctcagctca attacaaatt      240
ctatttgtcc acaaattcaa acattttaat gatgcattcc acataaaacc aatggtttga      300 gacaccttt caaaaaaaag aaaaaaatac actagcattg cttagacaag ttaatcaatg       360
aaaaataact ttatcttgtt tttaattaag gatgaaaagg agttacaaac gcttgtttca      420
agataaatat ttttcaaatc tttaatatta caagaaataa acggaccttc ttatcaacca      480
aaaaaatgta acataaaagg aacttaccaa tttgattgga ctcatttatt gattttgga      540 aaaatgtcgc aaattttcgt tgagttttag ctccatgtac aatttagtca ttgaactttt      600
aatttattca atataattca tgaactttct atacatattt agtccatata aaattaagg      660 gaccaaattg agtattcacc aaatttttag ggaaatatt gaataaataa aagttcttg       720 gaccaaattt catattgaaa taaaattcat ggacaaatca ttattccttg attaaacttt      780
tttatgtaga cacccgtaaa tacaacctgc caaggtttgt ttgcaaggcg tttgcaaggc      840
gtttgcactt aagcgggacg gaggcgtcac cagtcaatgg gcatgtccag tggcttcccc      900
ggcttgcgaa taggatgctt cctgaatcat ctcc                                  934

<210> SEQ ID NO 24
<211> LENGTH: 408
<212> TYPE: DNA
<213> ORGANISM: Eucalyptus grandis

<400> SEQUENCE: 24
aaagtttctc tgtagagaga gggagggaga tatatctgcg gtttgcgtct ctatttcgct       60
tgtgcagttt tactactccc caaacacaca cacactctct ctgtttctct cctttttccc      120
caaatcagaa gaagaaacga cagtgtagta gtgcagtttc actacaccgt ctatactaag      180
ggtaatcgtt ttttttgaaag cacatgcata tagccgttgg aaaggggagg gcaccgagat      240
cgaatcggat ggctgatcct cactagccgt tagagagaga gagagagagg gagggataat      300
catgtgcgga catatatccg caatttgcgt ctctatttcg cttgtgcagt ttcactactc      360
cccacacaca ctctctctct ctctctctcc ttttcccccca aatcagaa                  408

<210> SEQ ID NO 25
<211> LENGTH: 847
<212> TYPE: DNA
<213> ORGANISM: Eucalyptus grandis

<400> SEQUENCE: 25
ccttgtattt ccccaacatt aaatgaaagc ctacatccaa aaacgtggac ccggcattaa       60
```

```
agaaaaaccc catcatctca tcccatcctt tatttcaacc ctaaagtgaa attaagatat        120
aagacgaaac cacccccaac cccccaaaaa aaaaatatta agggaattcg tttttttgaa        180
agcacatgcg gaggtagctg ttggaaaggg gcctctacgt tcggaaggaa tgcgaccatt        240
ccatcgagat caaatcgaac tactgatgct cactagctgt tgcgtttaaa ccttctttgt        300
aaagcgataa gggaattcgt tattttgaaa gcacatgcgg aggtagccat tggaaagggg        360
cctctacgtt cggaaggaac acgaccgttc caccgagatc gaatcggacc gttgatgctc        420
actagccatt gtgtttaaag tttctctgta gagagaggga gggagatata tctgcggttt        480
gcgtctctat ttcgcttgtg cagttttact actccccaaa cacacacaca ctctctctgt        540
ttctctcctt tttcccccaa atcagaagaa gaaacgacag tgtagtagtg cagtttcacc        600
acaccgtcta tactaagggt aatcgttttt ttgaaagcac atgcatatag ccgttggaaa        660
ggggagggca ccgagatcga atcggacggc tgatcctcac tagccgttag agagagagag        720
agagagggag ggataatcat gtgcggacat atatccgcaa tttgcgtctc tatttcgctt        780
gtgcagtttc actactcccc acacacactc tctctctctc tctctctcct tttcccccaa        840
atcagaa                                                                 847

<210> SEQ ID NO 26
<211> LENGTH: 473
<212> TYPE: DNA
<213> ORGANISM: Eucalyptus grandis

<400> SEQUENCE: 26
aaagataaaa atagtgtgga aaatagattt gagaagtgtt catatatttc gatttatcat         60
agcaaagatt ttatcgacct attttaggct ttatagtgtg actatttaag ataacgaata        120
ttaatcgaga gatgcacaat taataagaga tattctcacg atcttgagat atatagaaac        180
cgacagaaaa tatattgatt atctctaata tagaataata ttctagagaa gtattgtaat        240
tgtgaccacc aactaaaatg gggcagacaa agtagagggc caggtatagt caaggccagt        300
gaaaaggaaa atgaaatgaa ataaaagaaa agaaagaaa  atcaaatcc tccaacttgt        360 gtacaggata cacccgaagc tttgtgtata taaaggccac ttaatatctc ctccaaccta        420
gcaacacatt cgaaagataa gttgcgctta atcctctcc aaaagagcta atc               473

<210> SEQ ID NO 27
<211> LENGTH: 519
<212> TYPE: DNA
<213> ORGANISM: Eucalyptus grandis

<400> SEQUENCE: 27
ctgctgaaat tctcgaggaa gttgagaggt tccagattag atctttacca aacaaaaaaa         60
aactattgct tatgctaaat tggtcattat aataagattt ttagaatact cgttgagtat        120
actcaactca agatattata agttttctca attggttttt ctccatttct tatgatccgt        180
ccacgagctt ggagtcgctt ttgaagatgt agccagccca acagaaccgt tccttcatc        240 ttcccgcgaa agtttcatgt catctccctc tctgcatca cgaaccaaac ctctgctctc        300
tctctctctc tctctctgct tcaacacaat gacaccaaca tcgcaccctc ctcaccttcc        360
caaccaccgc cataccatct cctttaagca ttccgatgag tccctgatcc accgccttct        420
cactgagcct tcccgctctc cctcttctcg tctcactttc tcatataaag aagtgaaaga        480
atacgaggat actccacttg ggtatcgcca agaactcat                              519
```

<210> SEQ ID NO 28
<211> LENGTH: 216
<212> TYPE: DNA
<213> ORGANISM: Eucalyptus grandis

<400> SEQUENCE: 28

```
gtgcggacac gtgtccccct atcccgccca agaccgcgca aaacctgaaa atcctcacta      60
ttccctcact ttcggcgaat tcgaaacagc gcataaagga acacggaaag aacattctct     120
accccaagac gacgacgacg acgacgacga cgacgccgcg ccttatataa accatcgcca     180
ctcctggcca ttcccttctt tctccccaga tccaat                               216
```

<210> SEQ ID NO 29
<211> LENGTH: 286
<212> TYPE: DNA
<213> ORGANISM: Eucalyptus grandis

<400> SEQUENCE: 29

```
aaattatgca atttcttaat caggcctagc tagaaacaag gcaaggaaa gcccccgacg       60
ggctcttatc tgctgacgtg gcacgccgtg ggtgggcccc ccgggtctt ccttcgacga      120
aacctcatcg tagacaatca atcctcctc tcgatcatta ttgcaaagcc aacacccagc     180
attgaatcga tccccacctt ctcctcctcc tctcttgat ccttttttgtc ccgatgatga     240
tgggtatctg atcagccgat tcaatcccat cgtctccttc cttctc                    286
```

<210> SEQ ID NO 30
<211> LENGTH: 168
<212> TYPE: DNA
<213> ORGANISM: Eucalyptus grandis

<400> SEQUENCE: 30

```
aaaaccacaa atggccgcgg acgtcacaa tttttttttc cttctagaag ctctatagtc       60
aaagctgatc tataaatttt tgggaaccac aaccaccatg tctcgccacc ttcgctcgaa     120
ccttatcacc accaccgccc ttgagccctc ctccatcaac tcttcttc                  168
```

<210> SEQ ID NO 31
<211> LENGTH: 748
<212> TYPE: DNA
<213> ORGANISM: Eucalyptus grandis

<400> SEQUENCE: 31

```
ctgtcacctc tggctggtcg ccgaacctca gcgaccgact ggaggaagaa gaggaaaaga      60
aaaaaataaa aataaaattc taaaatatta aaatattatt aaaagttgtc cacgtcagcg     120
ttgaggccac gttaactagc cggtgtcgag tcagcaaaat tcggccaaaa ttggcacaaa     180
aaaaggttta ggactttttt gacgcttttc ccgtcatgag cctaaataag aaatttttaat    240
ttcttcatac cataccaatt atttgatatg agattttttct aactaattca cacatctatg    300
ctaacgctac tcgctcaaaa agcgctcaag ctgaagccaa gtttcaagca tcaagcttat    360
aagccgagcc aagctcgagc acggtgcttc ttttctcggc ctgacccgat tagactcttg    420
actgaacatg acatatgaaa ttgcagagca ttcaatttaa aagattgtga aatttctggg    480
catttattta cctccctgtt aatgatattg cagagcattc aatttaaaga ttgtgaaatt    540
tctgggcatt tatttacctc cctgttaatg atatttttat ggaatagcgt gcaagaatt    600
cgggtgcata gtgttgtcct ctcccaacg cccccttata taatctccga acggagcaag    660
catttgctct tccgtaccca cggcattttc cttctcgtga ccttttcccg agaaaacaag   720
```

<210> SEQ ID NO 32
<211> LENGTH: 1161
<212> TYPE: DNA
<213> ORGANISM: Eucalyptus grandis

<400> SEQUENCE: 32

| | | | | | |
|---|---|---|---|---|---|
| aagaagagaa | aatccttcca | ttgcatcg | | | 748 |

| | | | | | |
|---|---|---|---|---|---|
| ctgacgccta | acatgtacct | taactgtaat | gtagcagcgc | aggtcgtcat | agcagaggcc | 60 |
| ggtcatgctg | gtcaggtagt | tactttaaaa | atctggaaag | cttctttgtt | gttgtctttg | 120 |
| ctgcttttct | tcgctctttc | ggcgaacttc | ccagtcgatt | catcggtcta | aagaatagac | 180 |
| acggaggtta | tcgcaaactt | atgcagagat | tccttgcggt | acgcaaatgc | atgtttaata | 240 |
| gatcattatg | ttaaatagat | aatatagtga | ctttcaggat | ccgtttgttt | tgcaaatttt | 300 |
| ttttcctaaa | attggtaaca | tgcaacgctt | gaaattatca | attagcgaaa | atattatta | 360 |
| tcatagagaa | caatttatat | aaaccttctc | ccagcctaat | aagcatgcct | ggttctctaa | 420 |
| tatcaaagaa | aaagaggagc | tagatctcgc | ctttagaatg | atttgaagta | attgcagtta | 480 |
| gcttgaagac | attcgtagat | gtcgattgat | caatgctttt | ggaagtacta | gagatgcgca | 540 |
| cgcatacgtg | cgatatccaa | actatttccg | ttgaccctca | cgaaaatctc | cgtacagacc | 600 |
| gttgttgcta | attctttatt | tgccgtaaaa | tctgcatgaa | tccataaatt | caatgattcg | 660 |
| aacgtgacgc | agaggaagtt | atgcattcca | aaagatagca | tttattttaa | ataaagaagt | 720 |
| gaagattaca | atatcttagg | tgcctattta | tagagaggtc | gtcatctaga | aaataaccaa | 780 |
| gtaaccgaaa | ttgaataaca | aaattaaaaa | atatatattg | ataaaaaggg | aaagttatca | 840 |
| aaatacaact | agaaaatctc | caaaatgtgt | ttgaaatctg | tgatatctcg | gatttgtggg | 900 |
| atcgcttgct | ctcatgacgc | tctaatgttt | ccataaaggc | atttgcggag | attattgtgt | 960 |
| cggattattc | agcttgcaag | aaaagttata | gtgcgagcaa | accatataaa | ataacaataa | 1020 |
| ataatggcaa | aaactatcgc | cgaaaattct | ccaatgacga | caaggactcc | gatttagtgg | 1080 |
| aattttgtgc | tgtcaatttg | actataaata | cccgcccgtt | gtgctcccaa | atcgagtgca | 1140 |
| agaaatgaaa | ctcctgacca | a | | | 1161 |

<210> SEQ ID NO 33
<211> LENGTH: 563
<212> TYPE: DNA
<213> ORGANISM: Eucalyptus grandis

<400> SEQUENCE: 33

| | | | | | |
|---|---|---|---|---|---|
| gtgaagagcc | atattttcat | tacataaagg | catttttttt | tttaattttt | aataggtggt | 60 |
| ccgaccgaca | agatattatt | atttttctat | ttgcatgaag | aagaaaaaga | ttggttttga | 120 |
| ccacaatggt | ttgtcctctc | gttacccatt | ttatatttgg | caagtttggt | gattgattgt | 180 |
| agaagaaaca | cgaaacacac | gagcaaaagt | aaaggactcc | aaacccaaat | tttaatccac | 240 |
| aaatgaattt | acccacataa | aaaaagggga | gattatgatt | aaattcgttg | aataatgcga | 300 |
| ccctttagga | gaaggcttat | taagcaagca | tcgacggaag | ctacacactc | cttttgggga | 360 |
| gaggctagtg | ggtgcaacaa | ctacgattcg | ggtagagcta | agctttgtcc | ccagtggcgg | 420 |
| tactgccatg | accagggctc | taaatcaaaa | cctaatctgc | caacctcaaa | acaaacgctg | 480 |
| tctcgccccc | cccggctgcg | ctatataatg | cagccgatgg | cgtccttcct | ttctcgaacc | 540 |
| ctaagcagat | caagagtttg | agt | | | 563 |

<210> SEQ ID NO 34
<211> LENGTH: 524
<212> TYPE: DNA
<213> ORGANISM: Eucalyptus grandis

<400> SEQUENCE: 34

```
aaattttttt ttttttttgg gtgggtagta ggatctgtca gagtaaagtg acttaacgcc      60
aattctcgac atttcagact aataaaatat ttacagatgc aacgtctcac tctctccttg     120
caaaaccaga aagggacagc aagcaagaag agggggaaga aagacttgc gttttaagca      180
aggggagtgc tgacttttca agcgacttaa ttaatctgtt tagcacccac tttggttcgt     240
ttgatcttct cgtgatttat tatttaccta tgtacagctg cggttgaaat ggcctctctc     300
gcttaaatgg tagtttgtcc ttttcttggg gtggttgctt tggaaatatt cttttagaag    360
caggggcaaa gaaatggagt ggcatctgat gcttcttcaa cactttgcag ccatatcgag     420
aatatatacc tagagagaga gagagagaga gagagagaga ggagcagtgg agaagaagga     480
gaagaagaaa agggtcagat cagatccagt tgttgggagc aagt                      524
```

<210> SEQ ID NO 35
<211> LENGTH: 1795
<212> TYPE: DNA
<213> ORGANISM: Eucalyptus grandis

<400> SEQUENCE: 35

```
atcattaata tcattagaaa gatatattac attttaaaga tgaataaaca tttgaaatgt      60
tttctctaca actaaaaaaa aaatcattgc ctctacaact aaaaaaaaga tcattgccca     120
ttatgacatt tcattttttt tctaatcaca tcaaattact ttagaataac tatccagctg     180
ccaaaaaaaa atagtattgt atatctaaaa taaatatatt gacaaatgcc aactaaatta     240
ggtatcaacg aatacctctt actttcctac aatcgaagat gtaaagacta atgtacattt     300
cttcatgatt atgtactaat cgattacaaa accaacatt tttttttagt tcttgaattt      360
cttttattta ggaacagtat ccaccaaata tgttctttag ctaaagaatg atatatatta     420
tttttaaaat tgcgattgga ttcttcatat gttatatctt gttcaaatat tattattttg     480
atttgatttt caaaataaaa cagaaaaata atctcatct cgttccttt ttcaatagtg       540
aaaatcccac caaattcatt gacaaaaaat catgaaaaca gtaaagcttg tattttcatt     600
cccaactttta aaactggtgg gtgacattcc aaatgatcat atggtcatat actaattttc    660
ccaatttctg agcgtgctca acgtgattgt accctttat tttcggatca tgccaggtca      720
atagagaaaa tttatcaaag attagtttaa tgatgaattg ggaccaacct ctcaagtcca     780
tgaaactgcc gtatgcgcaa ccgtaagctc cgttccaatt tttctaatga ttcaaggaaa     840
aataaataaa taaaaaagtc catcgtcgat gtgacatttc gcctgcgctc tccagctact     900
taatcaatca atatatacga attatttagc acatgacagc attttcccct ttttcctggc     960
gtcctcctag ggtggatccg gaccgtggat cgaactacag gagtggcggg gctctccgcc    1020
accgacagca aagtcaatat caatcatcga tggcagtcgc tttccggacg attcatactc    1080
atccgagtcc atttcccact tcaacctcaa gtccctcctc gtccacaaat gtaaaaatga    1140
aaaaatggag ggcagattag actgaatttt agctgtacaa cacatgttgc ctgtgcttca    1200
cgttcaagat ccacggttgc tttgctgttg cactcgcacc aactgtactg aatctccctt    1260
tatttctctc ttttaatttt tttttttttg ggtgggtagt aggatctgtc agagtaaagt    1320
gacttaacgc caattctcga catttcagac taataaaata tttacagatg caacgtctca    1380
```

```
ctctctccctt gcaaaaccag aaagggacag caagcaagaa gagggggaag agaagacttg    1440
cgttttaagc aaggggagtg ctgacttttc aagcgactta attaatctgt ttagcaccca    1500
ctttgcttcg tttgatcttc tcgtgattta ttatttacct atgtacagct gcggttgaaa    1560
tggcctctct cgcttaaatg gtagtttgtc cttttcttgg ggtggttgct ttggaaatat    1620
tcttttagaa gcaggggcaa agaaatggag tggcgtctga tgcttcttca acactttgca    1680
gccatatcga gaatatatac ctagagagag agagagagag agagagagag aggagcagtg    1740
gagaagaagg agaagaagaa aagggtcaga tcagatccag ttgttgggag caagt          1795

<210> SEQ ID NO 36
<211> LENGTH: 542
<212> TYPE: DNA
<213> ORGANISM: Eucalyptus grandis

<400> SEQUENCE: 36
aaactcatac tcttgataag atgcagacat tgctggcgtt caacaaggaa agaaaaaga      60 aggaataaga caaagtgaaa gagaaaaagg aaaaaaaaag taaagtaaaa taaaatatca    120
ttaaaaattg tgtatgttag ggttgttagg catttatgtc cgcaccaatt gacgcattta    180
tgtccgcacc aatcgaacca tttatgttcg caccaatcga cgcatttatg tctgcaccac    240
tcatctgcac caattggcca aaattggcca gaatgattga attgacataa ttgcaaaata    300
tctaagactg aacaagcaaa aaaaaaagtt atgaccgaat tagaaaaatt acaatagatt    360
tatgactttt tttgtaattc cccccaccta actctgtcaa acctgctaat atagactaat    420
tcattcatat atttatatat acacactcat aggttgatat atgaatatgg gggtacgtat    480
aaccctatgt gctaaaatct tggagaactt cctattcata tcagaagaag aaccgatcct    540
gt                                                                   542

<210> SEQ ID NO 37
<211> LENGTH: 858
<212> TYPE: DNA
<213> ORGANISM: Eucalyptus grandis

<400> SEQUENCE: 37
aaaacagatt gttttagatt gataacgttt tcctatcatg ccggcatcat ctcaattttg     60
aattatatcg gagcattaaa tataaaagtt aggttacgga tgaatgataa cgcagaccta    120
gtgagaaaat tagtataatc acgataaaaa tatccatata gacatcacaa aaatgccgcc    180
cgatctgatg aaatccgaca aataacacaa acatatatat gtccaagact tggacttcaa    240
gtcgacatgc ttgtgcatgc acaattttgg gccataaaat tgggcatgtg agaacctcaa    300
accgttaaga gatcaggtat ttactttgtt tgtcgactga cgagacgtgc acgcatttca    360
caccctcttc tcattgatct tcaaagcttt tccgaactca cgatggttcc agaaaggcga    420
tgttttgctg acagagggag cgttcgatgg agcttctcca tcacttaatt tgtcccttca    480
agatgaaaaa agtaagaggt ccaccgtacc aaaacattct tccacccaga agaaaaccac    540
agtagctgga gggagtcaag catgtcagaa gcacagaaac tgggaatggc taaaaagcaa    600
gtcttgaccc ttaacccacc ccactggttc acctaccgca cctcgggtta ggtattgctt    660
gctgaggtgt cacttttcgc caaagtcatg tctctctttt ggaatcttct tattggtccg    720
tctcgtttcc tcgttgctgg atgctggtag cgttttgtc catatatata tgcagtccat    780
atgtatcccc gtcactcctc atctatgctc ctacccggca acttcccact acgataagca    840
gcaagttttc ggctctgt                                                  858
```

<210> SEQ ID NO 38
<211> LENGTH: 547
<212> TYPE: DNA
<213> ORGANISM: Eucalyptus grandis

<400> SEQUENCE: 38

```
atcaggtatt actttgtttt gtcgactgac gagacgtgca cgcatttcac accctcttct      60
cattgatctt caaagctttt ccgaactcac gatggttcca gaaaggcgat gttttgctga     120
cagagggagc gttcgatgga gcttctccat cacttaattt gtcccttcaa gatgaaaaaa     180
gtaagaggtc caccgtacca aaacattctt ccacccagaa gaaaaccaca gtagctggag     240
ggagtcaagc atgtcagaag cacagaaact gggaatggct aaaaagcaag tcttgaccct     300
taacccaccc cactggttca cctaccgcac ctcgggttag gtattgcttg ctgaggtgtc     360
acttttcgcc aaagtcatgt ctctcttttg gaatcttctt attggtccgt ctcgtttcct     420
cgttgctgga tgctggtagc gttttgtcc atatatatat gcagtccata tgtatccccg      480
tcactcctca tctatgctcc tacccggcaa cttcccacta cgataagcag caagttttcg     540
gctctgt                                                               547
```

<210> SEQ ID NO 39
<211> LENGTH: 862
<212> TYPE: DNA
<213> ORGANISM: Eucalyptus grandis

<400> SEQUENCE: 39

```
aaacactttc tgtaaactta tttttgcaaa caatccaaag ccaaaaaagt aaagaaacta      60
ttttcagata ggaaattttt ctcaaaacaa ggatcgtcga tgggactgga gctctcagcc     120
caaaaagaa aaaagaaag gtaatgtgat gtaagagaga ggaaagtaaa gttgaagaac       180
gtgtatgcaa agcgacatga tgggggagag catttgatgg acaatcattg gccaactca      240
catgaagtcc ttacaacaaa cagttggagg acgatgcagc tccagctcga ttcagcgact     300
ccaattatat ttccctctct ggtcctctcc tcctttccat gcgcaatcca gctaagtttc     360
tattccatgg ccccttgct actagggtca catctgccag atatttttct ggtatgcagc      420
taaaagcata gtagtgccct ttggaaaagt tgatcatagt aactgggctg gtccagttta     480
attagagcaa tctatgatga aattactaat gaattttgg gaagttcggt ttttggtttc      540
tcggaattc tcaccaatat cattgcttca atattagtta aaatagacga ctgaaaagat     600
catgatagat aaaaaaaagg gagtggccaa attattttc tctaattctt acttaactta      660
agcttcatgc atgctgccca tcttgtgttt ggtcattaac taacctagaa ggagggggg      720
aaaaggtaaa acatgtcata aaaggtttag ttagacccct cacccaaaat gattgcccaa     780
tgccaccact ttaatcatca actttccaac caacacttgt ttttttggct tcccttttctt    840
atcctccatt ctcctctctc ct                                              862
```

<210> SEQ ID NO 40
<211> LENGTH: 611
<212> TYPE: DNA
<213> ORGANISM: Eucalyptus grandis

<400> SEQUENCE: 40

```
atcaatgagt gaaggggggc ggcacaagag agatatactt acacatgctc cccctagact      60
agacgacaga cgcaatttac acatgtccga gacatacggt catgaaatgg gaattctgat     120
```

| | | |
|---|---|---|
| gtagaaatag catgaaccca tttagcaaag aattgagaac tgggccggaa ctctgctcgt | 180 | |
| gttaactaat ccaagcgtcg gtcaagctgt gcgcacgcat gggtgggaag ggggcggggg | 240 | |
| taggtgcaca gggaatttgg tttgggggtt agagttggtc aaaagccgaa acggtgttag | 300 | |
| gcattgggct ttttggcttt cggcttcaag acaatttgaa ggggagatgg ggcgtgccat | 360 | |
| ctgctctccc cctgccatat gacccatcat cccctctcca tctccatcta cctctaccta | 420 | |
| ccccgcccc cttcctcttc ttctcctttt ctctttcctt cttcgaaaaa ttttaattta | 480 | |
| ttaaatatt tattgcccct cccctcccc ctctccaaaa ccgaatttaa cccaaccctc | 540 | |
| tctctttccc tccacccaaa tctctacaca tcatcatcat catcatcatc atctcctccc | 600 | |
| ctccctttc t | 611 | |

<210> SEQ ID NO 41
<211> LENGTH: 498
<212> TYPE: DNA
<213> ORGANISM: Eucalyptus grandis

<400> SEQUENCE: 41

| | | |
|---|---|---|
| aaaatcactt aacggcttca cccaatatac tagttatctc ataagtggca atctaaaaaa | 60 | |
| aaaaacacta tagttacgtc gatgaaaggt ccgacttatc tgttcgaaat cagaacctga | 120 | |
| atttctatta ttgatctaaa caaatcacgt cgagtgtgat ctagtttatg aaaaatacta | 180 | |
| caaagaaatg aaaaaaaaaa tgttaaattg aatgcaattt attagcaatg ggtttgaaaa | 240 | |
| ttagtaatag tatatctatt gtcatgcaag atatgaatat tttagatcct tctagaagca | 300 | |
| cggataactt atgactcgat gttttcttaa atctttggac acttgtcatt ttttcataga | 360 | |
| gaagcgacga gaagatcttt cgcggctgtt tcacctaccc caacctttgt ccctatgcat | 420 | |
| cttggctgag atgtcaacct taggcttccg acacctttga ctctctctcc tccatcgtcc | 480 | |
| tcatctctct cctgtata | 498 | |

<210> SEQ ID NO 42
<211> LENGTH: 362
<212> TYPE: DNA
<213> ORGANISM: Pinus radiata

<400> SEQUENCE: 42

| | | |
|---|---|---|
| aaaaaagttt cccaatctct aagcaaccat aaagctcaac cactctctgt cctgtgcccc | 60 | |
| aacgtctacc agacgattag gtatgcactg cagttcttcg tctgtcatgc taccagacag | 120 | |
| ttaggtaacc actaatgtct taggtggtga ttgatattga tgtttcttct gcaaacatgt | 180 | |
| gaatcaatgt gtatcgctgg aatatgacac tgtggatcac tggatataca tagagagatc | 240 | |
| tgctctgtcc attttaaca gattcatctc aattttcttg ttccaatgtc aacattttct | 300 | |
| caactgctct gccccatctt tattaaaagg gaacatctac cctgcatttc cacactccaa | 360 | |
| tc | 362 | |

<210> SEQ ID NO 43
<211> LENGTH: 810
<212> TYPE: DNA
<213> ORGANISM: Pinus radiata

<400> SEQUENCE: 43

| | | |
|---|---|---|
| cctataaaaa aagatttat taagagcatt tggaaaacta tcatctttcc aggaccataa | 60 | |
| aactatttaa tagttcaata aagatgaagt agttactatt taatagttta ataaaaatta | 120 | |
| agtagtctaa cagttatata gttatatata tgtgtgtgtt ttgggtatgt tttcaggttg | 180 | |

```
aatgatgtat aattgagtaa ggattttttt tggaattagt gaattttttt ttttcagaat    240
aacaattcta tatatatcat aaaaataaat tttaaataaa aaaaatctaa ataaaaatta    300
tttaaaaaaa cactaaaacc attagtatac caacacttca atttaatgat ggataaaata    360
ataagctagc tctgcttaac attacactgt ggtgagtttg acatgaaaaa atagatctct    420
gctttcagaa gtacgcattt ttaaatttaa aaaagtttcc caatctctaa gcaaccataa    480
agctcaacca ctctctgtcc tgtgcccaa cgtctaccag acgattaggt atgcactgca    540
gttcttcgtc tgtcatgcta ccagacagtt aggtaaccac taatgtctta ggtggtgatt    600
gatattgatg tttcttctgc aaacatgtga atcaatgtgt atcgctggaa tatgacactg    660
tggatcactg gatatacata gagagatctg ctctgtccat ttttaacaga ttcatctcaa    720
ttttcttgtt ccaatgtcaa cattttctca actgctctgc cccatcttta ttaaaaggga    780
acatctaccc tgcatttcca cactccaatc                                     810

<210> SEQ ID NO 44
<211> LENGTH: 334
<212> TYPE: DNA
<213> ORGANISM: Pinus radiata

<400> SEQUENCE: 44
aaaactaatt ttcaaaatat gaggaaaaaa gcgagaccac gaaaaaatca ttgaaaaaga     60
ccttgcaaaa ttcaggactt gctctcacca acctcgccag gactttgacc gtgctcatgc    120
ttgtgtcatg cttgcatatc tatacgtgtc acatcgaccg tccgatctat catgaaaaga    180
acggtcatga tgaaatctca actaaaccca ctgcgttaaa ttttcgaaca gtgagaaagt    240
aatcgtataa ataccctaa gctcttagac cgagaacgca tgcagcattc ggctctcatt    300
ctgaggttca tctggctgaa gtttgaactg tgct                                334

<210> SEQ ID NO 45
<211> LENGTH: 476
<212> TYPE: DNA
<213> ORGANISM: Pinus radiata

<400> SEQUENCE: 45
atcatcacca gtgccaccta agaacgcgtt tgtattgaga taccatctat tttttcggat     60
gcaattacta gttaataatt tataacatta ttaggggtgg ggtccagaaa atgaaaaaa    120 gaaaagaaa attgaaattt taaaactaat tttcaaaata tgaggaaaaa agcgagacca    180
cgaaaaaatc attgaaaaag accttgcaaa attcaggact tgctctcacc aacctcgcca    240
ggactttgac cgtgctcatg cttgtgtcat gcttgcatat ctatacgtgt cacatcgacc    300
gtccgatcta tcatgaaaag aacggtcatg atgaaatctc aactaaaccc actgcgttaa    360
attttcgaac agtgagaaag taatcgtata aataccccta agctcttaga ccgagaacgc    420
atgcagcatt cggctctcat tctgaggttc atctggctga agtttgaact gtgctc         476

<210> SEQ ID NO 46
<211> LENGTH: 536
<212> TYPE: DNA
<213> ORGANISM: Pinus radiata

<400> SEQUENCE: 46
aaagatgcta caatttgatt tcttttagt taaatttaat cagaaatata gaaaaaggtt      60
aggaagatgt ttgcagtcgt aaatatgagc gcaatggcct ttagtccacg cgtagtggca    120
```

| | |
|---|---:|
| catcttacac ggatacttgg ttttcagccc cacacaactg caagggttgc ttcgaaggta | 180 |
| actcttacgt tggtttgagt gcccaaaaca tattagcttt ttattttgtg tcactgtcga | 240 |
| catcgttggc cctaatttta tcgtatgatc aggccctgat ctctctcgcc accatttcct | 300 |
| tataaggcgc cagcagacaa gcacagctct ggaaggaaca tgggtgagtg acattaaagc | 360 |
| aacgcgatga cctcatacca gcttcaacag cttacaccat aagacacgct ttcccatgga | 420 |
| catcctccta cgtatcactc acttgcctat atattcatgc aactccgtca cagtttttata | 480 |
| ataattcagg tgccttttat atcagtagta tcaacggata cacccagggt gattgt | 536 |

<210> SEQ ID NO 47
<211> LENGTH: 680
<212> TYPE: DNA
<213> ORGANISM: Pinus radiata

<400> SEQUENCE: 47

| | |
|---|---:|
| aaattcatgt tgtcataggg ttatggtatt ttgcacacat gaaacaaatt ttacaattga | 60 |
| ctttgattaa gatattaaat ctacaatagg ttatcaactc cacgtgataa tgaagtaaaa | 120 |
| agactggatg gctaagtcaa taaaacaacc aaataatcaa gcaatgatag cttctatcaa | 180 |
| ataaggatgg ttcagctaga tccaggcgaa atatgattca gccagatacg aaaaggcgag | 240 |
| cggttgaaat gtttgaatgt ttgcggggtc cctggttgct tcggaggtta ttctacgtaa | 300 |
| tttattcgtt ataccttgcc ttctaagcat cgcaaactgt gatttcttaa caaactcgat | 360 |
| gcatgcgcca taaccaacaa aaccatttag ttgagtttac ggtcttcaca attcatgctc | 420 |
| agtcaccttc aactattatg acagattagg tgctacttat tctctcgtta ccctttagag | 480 |
| tgaactttaa tccaaattgt caggtgattt gggcccccag gcgatggatc cagcgacagg | 540 |
| ggaacgcaag tttggtggtt gtggcagtgc agttggtatg ccccagagag ttttaagact | 600 |
| tcagatttgt gttcagtatc aggagctgct atggaaaaag caaccatata aaactattgc | 660 |
| cattcgcaca ggaacagaac | 680 |

<210> SEQ ID NO 48
<211> LENGTH: 1607
<212> TYPE: DNA
<213> ORGANISM: Pinus radiata

<400> SEQUENCE: 48

| | |
|---|---:|
| cctttgggaa tgaactttga gaccacctcc aacccggatt ctgaaatcca tccagcaatt | 60 |
| ccaaagttcc aaaccgaaat aaacatccca ccataccatg gcattcggaa aaaagctagg | 120 |
| ctaagctgaa aatcactgtc ataacccagt aagaccatgc cactaatagc aagagaacca | 180 |
| tacaccaaca tgcaaagcca tgcatgtcca aaccagctag gaaatcacac atgcaaaggg | 240 |
| ttacctgcaa gtattcctgt tgaagttgct tgatcctact ttcttttcct tgagccttgc | 300 |
| ttgccttcct ttcctttgct tgattttcct ttccttgctc caaactagag tgctctaaga | 360 |
| aaactctaag tgaccaagag agtgagagag agagagaata tgagagtcc aaacatgaac | 420 |
| ttgacaaaag ccatgaactg atcctcagaa gtcattttat gcacgaggct tctatttttct | 480 |
| tcatttttcca tcattttcct tcaatttcct catcacatgc aacgtgcgac ttttcacccc | 540 |
| gttttcctcc taatttcttt tattttcata aataaatgtg ccaaaaatgc ctcttgcctt | 600 |
| agcctttgcc agtttcctta gccaaaacac acatccaatg atgcccacta ggatatcttt | 660 |
| gcccaacatt aagcctggaa taaatgtctc ttaatcgtgg tcttatttg cttttattaa | 720 |
| cttttattac atgaactttt cactaaagct attacaaaga tatatttatt atggcaatta | 780 |

```
tgtttgattt ttgaagagct agtaactttt agtttattat ggccttttcc gtaaacttat      840
tttcttgaaa atctctataa atccaatgaa aaatttatag aatatatgtt gtgttttctt      900
cactacctct aataaatttt ttacttagta atctacaaag ccatttatta aaaaattcaa      960
gttaattaaa aattaatatc atttcaaaag tcttttaat atagtcaaag tttattaaat     1020
tctatgatgt atatttcttt taaataaatg aagaatccat tttttactt aaaaccatat     1080 attttttata acgttgataa atagcatgca tttatataaa caaatatata ttttttataac     1140 gttaagagat tgtaaaact tttaaataat taatatttta tttattgttt tgaaaatgtc     1200
atgatttcca cctacctcgc ccatcaaatc ttgctgcaaa ccaggcttac ccaaccccac     1260
acccacaata tattttgggg atctggtgcc cccacctttg atcacagtga acaccataaa     1320
gacaaattat aaaggcaagg ggacttggca cccatgaggc aaccgaaagc aacaaatcat     1380
ttttttccaa agagatgagt gtatgccaac gaagaaacac gatgaaccca cgtgtcattg     1440
gccaactccc actttcgaca aaagaagga aattagaatt aaaaaggcga ataaaaattg     1500
aaaggccatt taaatagaa ggaagaatag cctatatggt agatttaaat gcttttttga     1560
aatccggtta ctcgcaagat tatcaatcgg gactgtagcc gaagctt                  1607
```

<210> SEQ ID NO 49
<211> LENGTH: 881
<212> TYPE: DNA
<213> ORGANISM: Pinus radiata

<400> SEQUENCE: 49

```
aaattagtca aatccaaagc agacaacttg ggctctcacc taaattaaca catatacccct      60 accagcttcc atagttttcca acttcctttc aataaatcta ttcaaaagca tgaaaagcat     120
gactaaggtt caattcccaa gttatggaca ccccacctgct ctaggcatat aggaaatcac     180
aatccaacta acgaccaact acccaaaact ttgaagaaaa tgagtaaaga ctccccccagt     240 gatattataa ttatatggtc tctctagaac cctttattgc cccttccagt gttatattta     300
gttccccatt tatatatccc ttgacttatg aaaccattta ggtgcattaa catagtcctt     360
gactaacaaa aaaattattt aggtgcagta gatacggaaa gtaaccaatg atgctaagaa     420
actgtgcacg tactttaatg gaggtattac ttttattatg gttggtttgg atacattcat     480
aatggaagca tgtgctcttc atcgttaaag ttgtggtggg gcattcccca ttttccacga     540
gaaaccgaat cccggcgtgg agacgacgac gaaatcgatg gatattcggt ggaaaattca     600
cagtaaaatt cctggagaaa aaggttgccg aggtagttga aatccaaacc gccgaaatga     660
gctggaaacc cgccttctgt cagttagttg agtcatgact gcagctgtct caggtcttac     720
actgtaaagg cacctttaatg aggcattcat tctggcagtc tggctacgga acttaatagt     780
acttgttatt cctgccccaa tatctattta ataggcatcc cccctcacta cttcttgccc     840
acaatccctc catagtcctg agcttgagac cattttctg c                          881
```

<210> SEQ ID NO 50
<211> LENGTH: 900
<212> TYPE: DNA
<213> ORGANISM: Pinus radiata

<400> SEQUENCE: 50

```
aaatataaca taatctaact attgatgtac attattcgcc tataacaaaa tctaagtatt      60
gatgtcacat tattggcata taacaaaatc tttaggataa cccttagtc aagctcttgt      120
```

-continued

```
actttcatgt ttattaacca ataaatcaag ctgatatgga atagcagacg tacgtggtaa      180
taataaatgg agtgtaagag ttcgaacatt ttaattcgga ggggcagctt atgtggaata      240
tcaggcaatc atacaagctt gcttttgggt aataaagacc cacatgtggt aataacaagt      300
ggattttaac aaaccaacat tttgataggg aggataggtg gcctggtaag ttagaatgtg      360
ctagtcatgc ctttgaaaga agttagttgt ggaagtcaaa catgttcccc acacaacaca      420
cctcaccaca caaaatgctg gtaggtcatg tgattgatgg atgggcatgt gtatcctcca      480
aaaaaaatga atatacacac taaatattct attgacataa tatacaaaga agattaggtc      540
tatggaagaa gggaaggcga aggggaagat tgggtcgtgg ggaagattgg gtcgtgtcct      600
gctagcacgt tgaataccta cacgccattt cacatctacc catcaacgtc aaatagagca      660
tccaaatcag ggcgtggtgg tgtgagggga gagtgaggaa aagaagttga aaaattctgg      720
ctgaaaatcc acctaacaca cgctcaccag cccctcaacg aggggcacca attatgaata      780
ataatagcta aacagagca gcagaagcag agtttatatc tatccattgt cgtctgtaaa      840
ttactctgtg agtgtttagt gttttcttct cttattgatt tcaggggaca agtaggtggg      900
```

<210> SEQ ID NO 51
<211> LENGTH: 603
<212> TYPE: DNA
<213> ORGANISM: Pinus radiata

<400> SEQUENCE: 51

```
aaacaccaat ttaatgggat ttcagatttg tatcccatgc tattgactaa gccatttttc       60
ctattgtaat ctaaccaatt ccaatttcca ccctggtgtg aactgactga caaatgcggc      120
ccgaaaacag cgaatgaaat gtctgggtga tcggtcaaac aagcggtggg cgagagaacg      180
cgggtgttgg cctagccggg atgggggtag gtagacggcg tattaccggc gagttgtccg      240
aatggagttt tcggggtagg tagtaacgta gacgtcaatg gaaaaagtca taatctccgt      300
caaaaatcca accgctcctt cacatcgcag agttggtggc cacgggaccc tccacccact      360
cactcaatcg atcgcctgcc gtggttgccc attattcaac catacgccac ttgactcttc      420
accaacaatt ccaggccggc tttcgagaca atgtactgca caggaaaatc caatataaaa      480
ggccggcctc cgcttccttc tcagtagccc ccagctcatt caattcttcc cactgcaggc      540
tacatttgtc agacacgttt tccgccattt ttcgcctgtt tctgcggaga atttgatcag      600
gtt                                                                   603
```

<210> SEQ ID NO 52
<211> LENGTH: 1631
<212> TYPE: DNA
<213> ORGANISM: Pinus radiata

<400> SEQUENCE: 52

```
atcttatgga gttttttaaat atatatatat tttttgggtt gagtttactt aaaatttgga       60
aaaggttggt aagaactata aattgattga gttgtgaatg agtgttttat ggattttta      120 agatgttaaa tttatatatg tagttgtgaa ggagtgtttt atggattttt taagatgtta      180
aatgtgtata tgtaattaaa attttatttt gaataacaaa aaattataat tggataaaaa      240 atgtttgtt aaatttagag taaaaatttt aaaatctaaa ataattaaac actattattt      300
ttaaaaaatt tgttggtaaa ttttatctta aatttagtta aaatttagaa aaaaaaataa      360
ttttaaatta ttaaactttt gaagtcaaat attccaaatg ttttccaaaa tattaaattc      420
atttgacatt caaaatacaa tttaaataac aaaacttcat gaaatagatt aaccaatttg      480
```

-continued

```
tatgaaaacc aaaaatctca aataaaattt aaattacaaa atattattaa cattatgatt      540
tcaagaaaga gaataaccag tttccaataa aataaaacct catggctggt aattaagatc      600
tcattaatta attcttattt tttaattttt ttacatagaa aatatcttta tattatatac      660
gagaaatata gaatgttcta gtccaaggac tattaatttc caataagtt tcaaaatcat      720 tacattaaaa ctcatcatgt catttgtgga ttggaaatta dacaaaagag aatcccaaat      780
atttctctca atctcccaaa ataaacctaa ttaatatagt tcgaactcca tattttggg      840 aattgagaat ttttctaccc aataatatat tttttttata cattttagag attttccaga      900
catatttgct ctgggattta ttggaatgaa ggtttgagta atgaaggttt gagttataaa      960
ctttcagtaa tccaagtatc ttcggttttt gaagatacta aatccattat ataataaaaa     1020
cacattttaa acaccaattt aatgggattt cagatttgta tcccatgcta ttggctaagc     1080
catttttctt attgtaatct aaccaattcc aatttccgcc ctggtgtgaa ctgactgaca     1140
aatgcggccc gaaacagcg aatgaaatgt ctgggtgatc ggtcaaacaa gcggtgggcg      1200
agagaacgcg ggtgttggcc tagccgggat ggggtaggt agacggcgta ttaccggcga     1260
gttgtccgaa tggagttttc ggggtaggta gtaacgtaga cgtcaatgga aaaagtcata     1320
atctccgtca aaaatccaac cgctccttca catcgcagag ttggtggcca cgggaccctc     1380
cacccactca ctcaatcgat cgcctgccgt ggttgcccat tattcaacca tacgccactt     1440
gactcttcac caacaattcc aggccggctt tcgagacaat gtactgcaca ggaaaatcca     1500
atataaaagg ccggcctccg cttccttctc agtagcccccc agctcattca gttcttccca    1560
ctgcaggcta catttgtcag acacgttttc cgccattttt cgcctgtttc tgcggagaat     1620
ttgatcaggt t                                                         1631
```

<210> SEQ ID NO 53
<211> LENGTH: 1163
<212> TYPE: DNA
<213> ORGANISM: Pinus radiata

<400> SEQUENCE: 53

```
aaacagagca gataacacta aaaagaccaa ccctgttagg aggggagaaa caaaaaagat       60
cacactaaaa agaccaaccc tcttatctaa acttattttc tcttatctct accccttcta      120
ttttgaacct ttatcatttt gatagaaaat atatgttaat aaccattaaa cctacattgt      180
caagctagtg taacttatat gttaataacc attaaaccta cattgtcaag ttagtgtaac      240
tcctttggtg ggggtggttg tcttcctctt caatctcatg ctatgacaca cttgtttttt      300
aataacatag gccgacaagt ttgagccatt atctatcttg attcctcgaa atgataaata      360
gatgttgtca gtggacttga aaaaaaccaa gtagggaaca ccacgtaatc tttccaatgg      420
cattaaaagc tactttgaaa tatgtaacac ttagcaatcc ttccaaggca ttaaacctac      480
tctaacctat ggaacactta gcatccttcc cacggttgat aataaatgat tgattcctca     540
gaataacaaa taaaaaaaaa ctataaaact tactctaaaa tataaaatga gtatggaaca     600
cgtggcaatc cttcccatgc tcggcggtag ctactctctc cagagatttg aataacacag     660
gcgccgcaat tatgagagag cagtggagtt aagactagt agccatggtt attttgaacg      720
cgtggcaatt cttccaaagg ttggtagtta ctctatccag agatttgaat aacacaaatg     780
ctgcagttat gagagagtag tagagttaag tcttgtcagc aatgatagtt acgaacaacc     840
gtaatttctg gctatctctg tgtttattgg tcgtttactt gctacagtgc tctcacccca     900
```

```
catggtaaca gtgttcgatg gccatgattt ctccccaccc cgccaaacct ctacgttttt    960
attcttttaa taactcctaa tttaatatat aagaggggc aaggtgttca tacagattcg   1020
tgcaaacgac ctgagttcag cacaagttta gtcattccat gcgaactcga ctggctcacg   1080
agatccctcg ctgcagttat agattgcagg aattagctta gcagcatttc tatctatgat   1140
cttctgccac ttcttcccct ctc                                           1163
```

<210> SEQ ID NO 54
<211> LENGTH: 638
<212> TYPE: DNA
<213> ORGANISM: Pinus radiata

<400> SEQUENCE: 54

```
aaggtttgct tggaccagcg acacagggaa aaacatggca tgcgggtttg gattaagatg     60
aggcccaatc ttaatttgat atgtttgcca aaccttaggt tgtttatcta attttttgatt  120 ggatctgatc tcttgatgat ttaagggttt tccatgttga cacgcaattg taggttcctg   180
ggcactaagg tctaccatgt ggcgaattta tcgagagttg acaattctgg tactgttagt   240
gatttgtcac cactctacgg tccctgcaga tctcagattt ttaatggctg cctttgatta   300
tctaaaggct agcccctaat cgcggctatg aatgtataaa gaatgtgttc caatgcatta   360
gagtactcaa agacatgttg aaggaaaagg acaagtcaag ggacatgagt aataaccaaa   420
aaagcacttg gtcctgacca tctgtgtctg attcacactg ggattcacat gttatttaag   480
aaaagttgca tcagtgctgc aatcatcaag ccattcctaa tttaccacca tgattagatt   540
attttaatgc aagaaaacgc ctatataagg agagctgcag gccccaaggt aatgcagtaa   600
tcaaacttga ggagagattt gagagtgttt gtgaaggg                            638
```

<210> SEQ ID NO 55
<211> LENGTH: 786
<212> TYPE: DNA
<213> ORGANISM: Pinus radiata

<400> SEQUENCE: 55

```
aaacgcttca tgccccagaa gccgcactcg atgctttaga ataaaatgga ccattaccag     60
actacgcgcc tccaaaataa caaaaacgtg tattagttaa accctacata gcacttaaag   120
cttgtcttac tattatttta cgtaattctg tcttttttgac agtggattga ttggaacttc   180
cattctcgat acagttgtat gcgttatgtg aactgaacca acctcggcca aaatatgggg   240
aagattcact tcagaaaaga caggacaacc atctctgatt gtcgacatta atatcggaaa   300
aaattcagtc aaatgatgtg gaaaggttca tctacggaaa ataaaatagc tctgagatga   360
cccgttacat ttagtgcata gcatctttgt caacaagaag aaatttccag ttgtaggact   420
ggtcatcaat ggccgtgcct gcaacgcttt tcgcaacag gaaacacgga ctaaaaacg    480 cggtctatct gtcatttgac ggtacgtttg gcactgagcc cgaaaaatc ccattggtag    540 aatttagaag agggagcttt cactcgaaaa ttctgtacca aagcggtgg cctcacaata    600 acaaattatt atacccacat ggaaaatgtt aaatcggacg gtccgacggt cgaccaaaga   660
caaaattgat gagaaagttt tgagggtggg tgataaagta agcgcgtctt tcacaggca   720 tctgcattat aaacctgcaa ctccaacttt catcacaaca aatttcattt tcccccttctc  780 tgaggc                                                              786
```

<210> SEQ ID NO 56
<211> LENGTH: 1302

```
<212> TYPE: DNA
<213> ORGANISM: Pinus radiata

<400> SEQUENCE: 56
aaacaacaaa aaataacaat ctacctagaa attatattac caaatttcaa ttaaaaaacc    60
catttcttag attattaaac tacaccatta taattttcat aataactact aatacaccat   120
tataaatttc ataatactat tcatcccatt ataaatttca taataacttc aatacacca    180
ttataaattt cataatacta ttcatcccaa tatgtgctac catttagata tttttgagcc   240
aaaacccaac ccgaacaaaa atttgtaatc tcgagattaa tcacaaaatt tgactcgatt   300
catatgcaaa ttggaataat tactcgtcat ggatgagatc ttaccgttgg tgtgatcatg   360
atgacggcca actttggcac gcttcatatc acaaattgca acaactactc tgcttttaat   420
ggatgaccat tgatgacgac caagcttgac acgattcata tgagagaaag aactcaaaca   480
atctactgca atgtgaaaag ccatgggcac cgccaagata tttaattgtc caacgcgtaa   540
caattagtta cccccaatgg gcattggact tgcctttgtc ttgatgtcga aaacaagggg   600
ggatttcctc tctttaagaa aaatagaaaa acaaaacccc ctgcacagct gggttctcct   660
ttcttcaagc ctggtttggc ttcaacataa agaaacaaaa cccattccat ggtgttgtct   720
tattgtgggt ttgcctaatt caatgttatt agtggttgaa acttcattac agcaggatgg   780
gagagccaac ctcaagagag tgactctgta accatcaatc ttccgcattg ccctgctgcc   840
atggatgtac tggcgaaaat aaagggtcaa ctttgcttaa agatgcagtc agctagagtt   900
taactcaagg aggcaaccgg cttctatgta atacctgtgg aatgaaaacg aatcccatgt   960
accgaattaa gggaaaactg ggtgcagaga ttttgtttgg tttagactct agatatggta  1020
ttacagctcc gattgggtgg tcgaaatacg tcagagcacc ccacattgcg taattcttca  1080
ggtatcagat gcctgcctag tctacataca tgagttgcag tttctcttca gcagtggggt  1140
ttggcggctc tgacagtaca gttagtagag actatctatt ttccgtgtac acaacgcttg  1200
caatgcagat ctgggcgcta ttataaaaga tcaaacaaga gctaggcttt cagaattgcc  1260
tgaaagctgc tgccaattgc atagatctgc tcaaggcacc ac                     1302

<210> SEQ ID NO 57
<211> LENGTH: 638
<212> TYPE: DNA
<213> ORGANISM: Pinus radiata

<400> SEQUENCE: 57
ctgtattcat cactttacac ccatgattcc aaaccctaca catttacact gataaccaag    60
ggttcaggtt ctttccaatt cattttaatc caggatgata taaatttga atagcacaat   120
agcatattcc aactgacata tccctacatt tgggatctct ttccacgtta taaatggctt   180
caatttaggg atccctttcc acattatata actgggttca cagtggtttg aagatagctg   240
tggtttgaag atagctgtat atgttatcaa aatgacagct cccttgccag ggaccatcgc   300
ttgaatgatg agatcccgcc tgtaaggcaa cttgcagcat gattatttta catctgcttg   360
accaattatc taacaatata cgcggtgtcg tcgttcggtt aaataatagt gaaacttcct   420
cgtgttgtcc ctgcagttac gtatgtcttg ttcttttttt tgtttaataa catacagcag   480
agcaagtgtt gggtgaataa atattgggaa gaagctgcag cgttcacgtt cattcattca   540
ctcatcgtga gcagcagtac atcaacagtt cttgaagaac attgataggt tggctatttc   600
aatcctttca tggggaatat ttaagtctgg atccgagc                          638
```

<210> SEQ ID NO 58
<211> LENGTH: 1350
<212> TYPE: DNA
<213> ORGANISM: Pinus radiata

<400> SEQUENCE: 58

| | | | | | |
|---|---|---|---|---|---|
| atcttatcac | attttctcaa | gagaagggtt | gtgaccaact | ttaaatttt | ggtctctttg | 60 |
| atggtggtaa | attggggcaa | tgagactcaa | cattgttaga | acatttacct | ttctcatact | 120 |
| ttggaggatc | tattaagaca | aaagctctca | tgtatttcct | ttacatgcat | gcacatttat | 180 |
| agggaataga | atggagtagc | aaattgactt | tctaaggaag | gcctactctt | gactcggggg | 240 |
| ttgtggcagg | tagttgaaga | ctagggagcc | ggtcactacc | aatttacca | tcaaccattt | 300 |
| acagacgaga | tacaaaatga | tgattatgtt | taattttga | aactttcact | tattaatttt | 360 |
| tgtgacgcat | tcataacata | ttatgttagt | atatatgttc | gttcacaggt | tgttggcttt | 420 |
| ggtaacacta | tactagtatt | tctttgtgat | tatttttat | gtaatgcaat | atagccctaa | 480 |
| atgaatattg | tgaaagtgat | attttcagg | agcatcaaga | ccatcttcat | ttgtaaatat | 540 |
| gtgataaaag | ggggtgtga | taatttag | tattttgtta | tttaataa | aataggaagt | 600 |
| gaagattatg | taaatattat | tttctaaata | aaaggatatg | agagaatagt | ttaggaaaaa | 660 |
| gaattgggat | agaatttcta | tgttttttca | attaaaatta | ggataagaat | ggagaataaa | 720 |
| gcttcacgct | ttaaatcatt | atgtaaaacg | gaaaagcct | gcttttgtaa | aagataaggt | 780 |
| ctgagaagac | ctatcccta | tgtatgtatc | cgttattatt | ataaataaag | aggtagctaa | 840 |
| tctctcaagg | gagagagagg | agcgagcgct | ctggaaaaag | atggatgatg | tcttgttaat | 900 |
| attgttaata | tggatgcgcg | tagttaatag | tttatttgga | ctgtgtatta | agcattgaat | 960 |
| ggttagctgt | atatgttatc | aaaatgacag | ctcccttgcc | agggaccttc | gcttgaatga | 1020 |
| tgagatcccg | cctgtaaggc | aacttgcagc | atggttattt | tacatttgct | tgaccaatta | 1080 |
| tctaacgata | tacgtggtgt | cgttattggg | ttaaacaata | gtgaaacttc | ctcgtgttgt | 1140 |
| ccctgcagtt | acgtatgtct | tgttctttt | tttgtttaat | atcatacagc | agagcaagtg | 1200 |
| ttgggtgaat | aaatattggg | aagaagctgc | agcgttcacg | ttcattcatt | cacccatcgt | 1260 |
| gagcagcagt | agatcaacag | ttcttgaaga | acattgatag | gttggctatt | tcaatcctct | 1320 |
| catggggaat | atttaagtct | ggatccgagc | | | | 1350 |

<210> SEQ ID NO 59
<211> LENGTH: 700
<212> TYPE: DNA
<213> ORGANISM: Eucalyptus grandis

<400> SEQUENCE: 59

| | | | | | |
|---|---|---|---|---|---|
| atcaattcaa | gtaaaaaatt | ttaatcctaa | cttagtcata | aacttttatg | caatattcca | 60 |
| atataatccg | tcagtcaata | ttaatcggaa | ttgttgacgt | agcgatgcgc | cacgtagaat | 120 |
| gactaacgat | ggctaaaccg | ctatagtagc | gatttctgac | aaatattaac | tgaatgacta | 180 |
| tattttcctc | attattcagg | ttatattgtt | ttgttttcat | gctatttccc | caatagcaaa | 240 |
| tttgttcacc | tgctcctgga | aattccttac | gacgactcac | cacttattct | aacgaatctg | 300 |
| atgggtgatt | cttgatatta | tttgaccatg | acataataaa | tgtcaaggga | aaagagaaa | 360 |
| aaaataagaa | aagcgaagaa | atccaccggt | catcattagg | acagacacat | tatacgccgt | 420 |
| cataagggaa | aatgaaattt | aactaaacat | cactaacgtc | aaccaaactc | gaaaacaaaa | 480 |
| cttgaactgc | agtagctaga | tgtagctctt | ggttcagccc | ccagaaccat | cgcctatcgg | 540 |

```
gttgatggtt gaagatgtga tcttggtcct aatcacctaa tcaacgaacc accgtttctc      600
attcgctccc tccgtataaa aacctcgagg cttgtcctat cttggagcat cgcatccaag      660
aaacaccatc tcatcctgtc tcagtcccca tcatcacttg                            700
```

<210> SEQ ID NO 60
<211> LENGTH: 1032
<212> TYPE: DNA
<213> ORGANISM: Eucalyptus grandis

<400> SEQUENCE: 60

```
gtcgttttta tattgtctag ccacattagc atgaaaaaca atgttgtttt gcatttcctt       60
tgtcggaaaa ttgccgcgtt ggcattttgg ttggaatgac acttaaatga tccattttgt      120
tttgattttg acacttaagt attactttcc aaagttttga cacttaagtg tccattcgca      180
ctaagttttg gcatttgagt gttcctccgt atcaagtttt gacatttgta atgtacttt      240 gctcataatg ctaatgtgat aatgagacta aattaaacat atattaaaat ttcagaatct      300
acattaaata atttaaaaat ttatgaatca tattacatat tacgataaag ttcaagaact      360
atattaaaaa aattaaatat ttatgggtca cattacatac gagtgaaaat ttaaggacta      420
tttattttgt tatttctttt tccattaaca aaaatcttcc ccacctcatt ttaaattcga      480
gaaaagaaga aaagcaaaga aaataatag agaggaaggg acccaactcg agattgggct      540
ccattgatgg aaactcgcga tctactccat ctcgactcga cagcccatcc tctgaagata      600
acatcatcgt ccgcaccgca ttgcacccta ccttctgggc tgaatgacca cattgcccct      660
ccaccaaatc tatccgttgc ctcgaatgcc ggatggcaaa gcagcaattc ccgcaaaagt      720
ccgagcccat ttccctccgg ccaaatcgag aaaggactct tgattttttga aaactgggcg      780 ggcaactaac cttggttagg cgcctccatc attaacccca caccaaagtt aacacccccg      840
ctttcgctgg cactttctaa atcgaaccgc ggttaacgta accgcggtta accaaccaga      900 tattttcaa ttttttccag tggcgctcta tatatcttta aacttcccct ctgcatttcc      960
catcagctct gcaagtcctc ctccatcttc ttcttcttca tcgtcatctt ctcggaaggc     1020
gtcttgataa ac                                                         1032
```

<210> SEQ ID NO 61
<211> LENGTH: 529
<212> TYPE: DNA
<213> ORGANISM: Eucalyptus grandis

<400> SEQUENCE: 61

```
atcaaagtta gtcgcacttt tacataccca actgtacctc caaagtgcac cattgaactt       60
gtgacaacgt ttagatttag gtaattattc agaaaacgaa agcgaccaca ggtttatgaa      120
ttgtcacgca tgacgtcatt aattaagcga caagacgtgc gccaaggcca tgcattcctc      180
tgcggctatc cttcttcctg gcaacagttc aattcctcag acggtctggt caaacccgaa      240
gctcgactag gccttttctca accaaacect ccaagaaagc ctaaggacag catgccctcg      300
cgcggatcaa cacgaccgac gagcatcgaa cttgcgtaac ttaccccacc aaacggtccc      360
cttcgaggtc aaaccccacg cgaacgaccg atgaatcgaa catctaatct cgcctctcct      420
ctcctccact gctatatatt tcagctactc taacacactc tcatcaccac caacttcaaa      480
ctctctctct cccctccctcc ctccctctct cgctcacaca tacacacat               529
```

<210> SEQ ID NO 62

<211> LENGTH: 710
<212> TYPE: DNA
<213> ORGANISM: Eucalyptus grandis

<400> SEQUENCE: 62

| | | | | | |
|---|---|---|---|---|---|
| ctggagttca | cattgagctg | gtgccgatcg | atccgtttct | tacattttt | catcccggtc | 60 |
| cgtctccatt | ctctgcctcc | gtcggcatct | tgggcgacga | gaggaggagg | agatacgcgg | 120 |
| tagctgacga | gttcgaggcg | caacttttct | tcgattaact | tttaactcga | caccgatcat | 180 |
| gctttaagca | cttacccttt | tcgagaaaca | ggagatggac | atggagttcg | acgtaaagat | 240 |
| cccgtctttg | attacagaaa | aagcatgctc | agaggaggag | gaatgatatt | tcctgtttcc | 300 |
| atggtggtga | taaaagcttt | gattttcct | tttcaatgac | gtagctcgag | tggccgataa | 360 |
| tcgacaagga | ggtccaacta | ttagcaccag | aatggaaaag | aagagggaga | tagatagcga | 420 |
| ctaccacaag | ctacattaca | aggattaata | taagcaaaat | tactgcaata | cgatattgac | 480 |
| ccgattggct | ttggatgata | aaaaaacaat | tctatattca | atcacacgtc | ttcgtccccg | 540 |
| ggaaagcaat | gatccaaatc | atgtcaagga | gctatactcc | taagcccacg | ttagcccaca | 600 |
| ctcttctcga | aagacatatc | aaatcaatac | actcactctc | tctattaata | ttcaatttct | 660 |
| gcataatttc | ttctgtcact | gcccaagacg | ttctgtagca | ctaaggggtg | | 710 |

<210> SEQ ID NO 63
<211> LENGTH: 365
<212> TYPE: DNA
<213> ORGANISM: Pinus radiata

<400> SEQUENCE: 63

| | | | | | |
|---|---|---|---|---|---|
| aaattcacat | tcttttctt | cgcacgaaga | aaggttaaag | atacaactcg | gattgtatta | 60 |
| aaggaaagag | attggaacaa | acagaatctg | gaatataaga | atacaccaga | tcgcgggcac | 120 |
| ggccacagtt | taacggccag | ccgaaaggcc | ggtccgttgg | gtctgccggt | gacttggtcg | 180 |
| tgtgagggaa | tctctggagt | ccggatccgg | tcttgccttg | agacctacca | caaccacagc | 240 |
| agttaatgca | gtttacatcc | tattaatata | aataccaaat | cgccattcca | aattattatc | 300 |
| acaacaacaa | atctgatttg | atttcgatgc | agtgaagctc | ttcatttgc | agtgacagtg | 360 |
| acgtt | | | | | | 365 |

<210> SEQ ID NO 64
<211> LENGTH: 1304
<212> TYPE: DNA
<213> ORGANISM: Pinus radiata

<400> SEQUENCE: 64

| | | | | | |
|---|---|---|---|---|---|
| ggacaaacga | gatttattc | tcatccagtt | ccatctattc | tctgtcactg | taacttgtag | 60 |
| agattatatt | aacgatgggg | ttatgatcgc | ttcacgtttc | cagatagaat | ggagagaaca | 120 |
| acagcaagga | aatcgacagg | ccataactta | atggggtcac | tgtaaggcct | tccggggcgt | 180 |
| aaacacgaag | ctttgtacag | agagtccacc | caaaaacaag | catcatcaca | gtgacaataa | 240 |
| ttgaaaaaga | aatgaaaagc | tccactgggc | ttctcttct | ggaaccttct | ctccgaagaa | 300 |
| atcgacttac | agaatttaaa | aaatttaaaa | tgatgttctg | tagcaaccta | ggccctccac | 360 |
| tgtcaccata | cctgccctc | cattgtcaca | ttctatcttc | tcatcttaaa | caccacgcat | 420 |
| ctcgcttttc | cactgcatgc | agagatcgac | gatatctttg | cttgatatct | aagtcgaatt | 480 |
| ctgaccgcaa | acctccatca | gacttgcgca | catcttaata | gatggcgctt | gtttgtgccc | 540 |
| aaggggttct | gggtactatt | tgaggactga | aggtgttatg | cttcagagat | ttggaggcct | 600 |

```
agggttcgat tcacagccgt tgagatttcg acagaatttg gattttttt ctctggctgt      660 ttgaggagaa tgagagagat attgcacatc cagggcgggc agtgcgggaa ccagatagga      720
gccaagttct gggaagtgat atgtgacgag catgggattg ataccacggg ctcgtactgt      780
ggggactccg atctgcagct ggagaggatc aatgtctatt ataacgaggc aagcggcggc      840
cgctatgtgc ctcgggcagt gctgatggat ctcgaacccg ggaccatgga cagcgttcga      900
tcaggtccct atggtcagat cttcaggcca gataacttcg tctttgggca gacaggcgcc      960
gggaacaact gggccaaagg gcattatact gaggggcag aactcattga ctccgttctt     1020
gatgtcgtgc gtaaggaggc cgagagctgc gattgtcttc agggatttca agtatgtcat     1080
tccctgggag gaggaacagg atcgggaatg gggactctct tgatttccaa aataagggag     1140
gagtacccag acagaatgat gttgactttc tctgttttc catcacctaa ggtatcggac     1200
acagtggtgg aaccttataa tgcaactctt tctgtacatc aattggtgga gaatgcagat     1260
gaatgcatgg ttcttgacaa tgaagcactt tacgacattt gctt                     1304

<210> SEQ ID NO 65
<211> LENGTH: 2062
<212> TYPE: DNA
<213> ORGANISM: Pinus radiata

<400> SEQUENCE: 65
gtatcattat ttcagtcatt atcgataatg ataagcctca aatatgaatc aatagtctct       60
tagtcattta atttatggtt ttcagtgtcg atgtgctctc ctgccagggc tccaccaatc      120
tcctttaggt tcagtgtaca tcgtctgaaa ataagttgac aaggccaggt caatgcagaa      180
gcctcctggc ttggggaccc taagtgtgaa atcaatatat tttcctcgag ttcttgacct      240
gttagcaact tcgacactgc aacttgtcct aatctttgct gtgtattatg tattttgttc      300
caagtattgg agtgtagcac agtggatggt agagaggagg atctagatca gtcacttta       360 catagaatgg agatgatagt aaaagcaact acaattacga tcttgctacc agtcatccta      420
tgttgcatcc catgtggaga aagtggaagc ggaggcagga gtttggcgca gcgtttacca      480
gccctaggcg ttgactatgg acaaactgca gacaatcttc ctccaccatc tgcagtagca      540
aagctggttc agagtacaag tatttcaaag ttgagactat atggagcaga tcctgcaatt      600
cttcaagcat ttgctaacac aggaattggg ttagttgtag cattggtaa cgatcaaatc      660 ccatctctga accagctggc tgttgcacag aattggatta gaacaatat cgttcctttt      720 gttcctgcca ctgatatcat tggaatctcg gtggggaacg aggttctgtt cagtggggat      780
gggagtctga tttcccagct cctccctgca ttgcagaacc tacacactgc ccttgttgag      840
gtttcacttg accagcaaat taaggtctcc acacctcatt ctctggccat actttctaca      900
tctgtccccc catctgctgg ccgtttcaat gaaagtttg acatgaaatc cctgcttgac      960
ttcttgcaga agatagggc cccattaatg atcaacccat accctactt tgcttacaag     1020 agtaatccca ccgatcaaac cctggcttat gcactcttcg agcccaaccc gggcttctat     1080
gacacaaaca gtgggctcac ctataccaac atgtttgatg ctcagcttga tgcagtgtac     1140
tcagccatga atatctgggg ttaccctggt gttgatatag tggtggctga acaggatgg     1200 ccagctgtgg gggatcctac agagacaggg gtgagcttac agaatgcaat tgcttacaat     1260
ggcaacctga tcaagcatgt gacgtccatg acggggaccc cattgaggcc aaataggtac     1320
attcaaacct atattttgc cctctttaat gaggatctga agccaggacc aacttcggag     1380
```

```
cgcaattatg ggctgtttaa agttgatatg acaatggctt atgatgtggg tttgttgcaa      1440
tcgccgagtg cagctccatc tcctcctgct ccacgcactg gggggcctgt gacaactcct      1500
cctacaggta aagtttggtg cattgccaag ccgggcgccg aagagcaaac tttggaggca      1560
aatttgaact atgtttgtgg acagggcatt gactgtaggc ctattcaacc aggaggtcct      1620
tgctattcac caaatacagt ggcaggccat gctgcttatg ccatgaacgc atactatcag      1680
actgcgggtc ggaacaattg gaattgtgat tttgcgcaga cgggaactct tacctccaca      1740
gatccaagct acggggcctg cgtgtacccg accgtctaag atatgaatca atcaatcaat      1800
cctagtgttt tctattccac ttgttgttcg gtatatattt tccaacttgt cttttcatat      1860
gagtgagatg tatgaggtac ctattttcaa agttgtgata gcatatacat cataagatgt      1920
aatgtgtatg tttgggtttt attccccctt taatgtcgtt actctgacca tataaaaaaa      1980
ttcacagaat ttgtgaatgg tagtattatt ttttatttat gtattaagga aatttaagtg      2040
gtgttaaaaa aaggaaaaaa aa                                              2062

<210> SEQ ID NO 66
<211> LENGTH: 542
<212> TYPE: DNA
<213> ORGANISM: Pinus radiata

<400> SEQUENCE: 66
aaaaaaaatt atgatctgta aataaatata attccatata taatagatat atataaattt        60
tacaacccac agataaatat taactttccg ccaaaataat ttccataaat gaaataaatg       120
acccaatatt acgattttac accaaaatga tttccatatg tatatataaa gcctgtgagt       180
ccaaacgaag catatgaatc tgaatcgcag agggaggctg ccaaccacc attagctatt       240 caatgaagtt ggtagccacc caaacaagtc aattcaagag tcaatcaaac caaactatga       300
ttaaaactac caaccgcact ttctgagcaa cccactttcc ctccctcgct ttacttttg        360 gagtcgtggg ggattttttcc agtgtctcaa tttctataaa tttggcctca catttcctac       420
caactcattg ttaacgggag tcctcttgtc aggctccgct gcttcttgtg atcacacgat       480
acctagtgat ccatagataa ctaaaatgct gtgagcagtc tgaattcttg ctttctttcc       540
cc                                                                     542

<210> SEQ ID NO 67
<211> LENGTH: 349
<212> TYPE: DNA
<213> ORGANISM: Pinus radiata

<400> SEQUENCE: 67
gtctgtatta ttatattctg ggtcactact caaccccacg gtagtggcgt gacttgcgtc        60
ggcgtgttac agaatccata atcagaaaac gaacggaagc tgcaaaggtg tacgtccaac       120
ggttgcggtg aaaagccatt ggttacgtcc agcggtggaa ttctgtaata ctgaaaggat       180
ttggttacag atggctcgac caaagacaaa atagtaatca atattcaac cgaaagggag        240 aaagttgctt atgggcatca cgttataaaa gtggaactcg actttcatta ccacacattt       300
ctcatttctt tctctgtact gagccattcg ttctcctttc tttcagaga                   349

<210> SEQ ID NO 68
<211> LENGTH: 222
<212> TYPE: DNA
<213> ORGANISM: Pinus radiata

<400> SEQUENCE: 68
```

```
ctggcaactg gctattcctc attcgtcagt gggaatgggg tgggcagacg atcttctaga      60
gcctgtgtgg tgtggggccc ttcgactttt caatggcccg ttggtcacca gcttggacta     120
gttttgctgt ttccatggtg acggttcgtg ctctataaaa taatttaacc gagtgggtat     180
tttgcatggt ggccggattt ccaacaatct caggtattag cg                        222

<210> SEQ ID NO 69
<211> LENGTH: 403
<212> TYPE: DNA
<213> ORGANISM: Pinus radiata

<400> SEQUENCE: 69
atctaaccca cgatctataa taatagtcaa ggaccctaaa tagaaatatg gccaccaccc      60
taccacgaga gcttatccta atacaaccac gaaagcccct ccactcgtgg aggttataga    120 tttccccccgt gtaaacatat aaaaggaact tttctctttg gtgaccggca acaaccggat    180
actcacccgg tatcgccgaa gaagcttgtt gcgaggttcg cattgaaaac cctcctctct    240
tcacattctt tgccggtcat ccatcttgct catttctact tccgcctcct cttctcttcc    300
ctcgtctagt gttttctttg cgttgtgtag tgtaatgttt gctgttgctt catatcaata    360
gtggtggaat tttccttcac tgcgagcaga ttttctaagg aga                      403

<210> SEQ ID NO 70
<211> LENGTH: 1032
<212> TYPE: DNA
<213> ORGANISM: Eucalyptus grandis

<400> SEQUENCE: 70
gtcgttttta tattgtctag ccacattagc atgaaaaaca atgttgtttt gcatttcctt      60
tgtcggaaaa ttgccgcgtt ggcattttgg ttggaatgac acttaaatga tccatttttgt    120 tttgattttg acacttaagt attactttcc aaagttttga cacttaagtg tccattcgca    180
ctaagttttg gcatttgagt gttcctccgt atcaagtttt gacatttgta atgtactttt    240
gctcataatg ctaatgtgat aatgagacta aattaaacat atattaaaat ttcagaatct    300
acattaaata atttaaaaat ttatgaatca tattacatat tacgataaag ttcaagaact    360
atattaaaaa aattaaatat ttatgggtca cattacatac gagtgaaaat ttaaggacta    420
tttattttgt tatttctttt tccattaaca aaaatcttcc ccacctcatt ttaaattcga    480
gaaaagaaga aaagcaaaga aaataatag agaggaaggg acccaactcg agattgggct     540
ccattgatgg aaactcgcga tctactccat ctcgactcga cagcccatcc tctgaagata    600
acatcatcgt ccgcaccgca ttgcacccta ccttctgggc tgaatgacca cattgcccct    660
ccaccaaatc tatccgttgc ctcgaatgcc ggatggcaaa gcagcaattc ccgcaaaagt    720
ccgagcccat ttccctccgg ccaaatcgag aaaggactct tgattttga aaactgggcg      780 ggcaactaac cttggttagg cgcctccatc attaacccca ccaaagtt aacaccccccg      840 ctttcgctgg cactttctaa atcgaaccgc ggttaacgta accgcggtta accaaccaga    900 tattttttcaa tttttttccag tggcgctcta tatatcttta aacttcccct ctgcatttcc    960
catcagctct gcaagtcctc ctccatcttc ttcttcttca tcgtcatctt ctcggaaggc   1020
gtcttgataa ac                                                       1032

<210> SEQ ID NO 71
<211> LENGTH: 1039
<212> TYPE: DNA
```

<213> ORGANISM: Pinus radiata

<400> SEQUENCE: 71

| | | | | | |
|---|---|---|---|---|---|
| aaataggcta | aattagagaa | atactatggg | ttgtcaaaac | ctagaatacg | ataatttgac | 60 |
| cgaaatattt | agataatgta | acataacatg | acatgacatt | acaacatctc | ttccatagag | 120 |
| aatctctcaa | taaaataaaa | tattgcacaa | acaaaaccaa | ctcaaaactc | aatttatatt | 180 |
| acacaatata | ataataaaca | atttcaatta | aaaacatttt | acctttattt | attaataaac | 240 |
| ctcacactaa | cacattgtta | aaaagtaaa | ataaaataac | aaacgccata | taaacccata | 300 |
| aaaatttcca | aaacaatatt | aatatcttta | tcatagtttt | taagctaaag | ttcgatgatc | 360 |
| ctttaacatt | actagccaca | aggatgctta | cttccttgca | aaataacaat | gcaaagaccc | 420 |
| aacgcagtga | tatgtgattt | aacggtaagt | atggttgggt | gaaaccaaca | agactgcagt | 480 |
| tcaaattcca | ttgagtatat | ggcctgctat | gatctcagct | tggtgaaacc | aacaagactg | 540 |
| cagttcaaat | ctaaatccca | ttaattatgt | gacctactat | aatctgggct | taaggagtag | 600 |
| gttgctcgct | atgttttggt | gttataaagt | agccataaag | attaaacctc | aagctcccct | 660 |
| aaattaatcc | aagaaattac | cgattcatta | taattaaaaa | aaatgcaaat | acccaccttta | 720 |
| aagaaaaaca | atgtaaagag | caatgaaatc | aatttaattg | tcttcttttta | acaccaataa | 780 |
| aaatttataa | aaacctcata | attaaaaaca | aagcgttaga | cttttggaat | aaccttcctt | 840 |
| aattgcttct | ctaatttatg | atttctaagt | cataccacga | tcggtcgttt | tagcaaaagc | 900 |
| ctgaaaggca | agtagaagat | aaacgtatgc | ttggaaataa | atatatgtca | tttttcattt | 960 |
| tatatccttc | gaatccgtca | ttcgtctgaa | tgatcagaca | aaccctccca | gatcctgctc | 1020 |
| tgttctgaag | cataaacct | | | | | 1039 |

<210> SEQ ID NO 72
<211> LENGTH: 13
<212> TYPE: DNA
<213> ORGANISM: Artificial Sequence
<220> FEATURE:
<223> OTHER INFORMATION: Description of Artificial Sequence: Synthetic
   nucleotide motif sequence

<400> SEQUENCE: 72
aatcaaatcc tcc                                                          13

<210> SEQ ID NO 73
<211> LENGTH: 13
<212> TYPE: DNA
<213> ORGANISM: Artificial Sequence
<220> FEATURE:
<223> OTHER INFORMATION: Description of Artificial Sequence: Synthetic
   nucleotide motif sequence

<400> SEQUENCE: 73
aatcaaatcc tcc                                                          13

<210> SEQ ID NO 74
<211> LENGTH: 12
<212> TYPE: DNA
<213> ORGANISM: Artificial Sequence
<220> FEATURE:
<223> OTHER INFORMATION: Description of Artificial Sequence: Synthetic
   nucleotide motif sequence

<400> SEQUENCE: 74
tctccctcct ct                                                           12

```
<210> SEQ ID NO 75
<211> LENGTH: 13
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 75
ataaagaagt gaa                                                          13

<210> SEQ ID NO 76
<211> LENGTH: 14
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 76
taaacttatt ttct                                                         14

<210> SEQ ID NO 77
<211> LENGTH: 14
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 77
taaacttatt ttct                                                         14

<210> SEQ ID NO 78
<211> LENGTH: 12
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 78
ggagaaacaa aa                                                           12

<210> SEQ ID NO 79
<211> LENGTH: 16
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 79
aagtaaccaa tgatgc                                                       16

<210> SEQ ID NO 80
<211> LENGTH: 13
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 80
actttgaaga aaa                                                          13
```

```
<210> SEQ ID NO 81
<211> LENGTH: 11
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 81
tgaggagaag a                                                              11

<210> SEQ ID NO 82
<211> LENGTH: 11
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 82
atcaagctga t                                                              11

<210> SEQ ID NO 83
<211> LENGTH: 12
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 83
aatttcattt tc                                                             12

<210> SEQ ID NO 84
<211> LENGTH: 13
<212> TYPE: DNA
<213> ORGANISM: Artificial Sequence
<220> FEATURE:
<223> OTHER INFORMATION: Description of Artificial Sequence: Synthetic
      nucleotide motif sequence

<400> SEQUENCE: 84
taaatttgaa ttt                                                            13

<210> SEQ ID NO 85
<211> LENGTH: 40
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 85
aaatataaca taatctaact attgatgtac attattcgcc                               40

<210> SEQ ID NO 86
<211> LENGTH: 10
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 86
cccacctacc                                                                10
```